US008013120B2

(12) United States Patent
Du Clos et al.

(10) Patent No.: US 8,013,120 B2
(45) Date of Patent: Sep. 6, 2011

(54) C-REACTIVE PROTEIN AND ITS USE TO TREAT SYSTEMIC LUPUS ERYTHEMATOSUS AND RELATED CONDITIONS

(75) Inventors: Terry W. Du Clos, Albuquerque, NM (US); Carolyn Mold, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 433 days.

(21) Appl. No.: 12/083,055

(22) PCT Filed: Oct. 26, 2006

(86) PCT No.: PCT/US2006/041583
§ 371 (c)(1),
(2), (4) Date: Aug. 11, 2008

(87) PCT Pub. No.: WO2007/050661
PCT Pub. Date: May 3, 2007

(65) Prior Publication Data
US 2009/0298759 A1  Dec. 3, 2009

Related U.S. Application Data

(60) Provisional application No. 60/730,013, filed on Oct. 26, 2005.

(51) Int. Cl.
*C07K 14/00* (2006.01)
(52) U.S. Cl. ............................ 530/350; 530/380; 514/1.1
(58) Field of Classification Search ................ 514/2, 1.1; 530/324, 350, 380
See application file for complete search history.

(56) References Cited

U.S. PATENT DOCUMENTS

| 5,593,897 A | 1/1997 | Potempa et al. |
| 5,783,179 A | 7/1998 | Nestor, Jr. et al. |
| 6,239,099 B1 | 5/2001 | Potempa et al. |
| 2002/0081690 A1* | 6/2002 | Yamamoto et al. ............ 435/190 |

OTHER PUBLICATIONS

Zen (Journal of Cellular Biochem 64, 140-151, 1997).*
Mok Chi Chiu, Arthritis and Rheumatism 50(8), 2559-68 (2004).*
Barna BP et al., Activation of Human Monocyte Tumoricidal Activity by C-Reactive Protein, Cancer Research 1987, 47: 3959-3963.
Barna BP et al., Therapeutic effects of a synthetic peptide of C-reactive protein in pre-clinical tumor models, Cancer Immunol Immunother 1993, 36:171-176.
Barna BP et al., Combination therapy with a synthetic peptide of C-reactive protein and interleukin 2: augmented survival and eradication of pulmonary metastases, Cancer Immunol Immunother 1994, 38:38-42.
Barna BP et al., Activation of alveolar macrophage TNF and MCP-1 expression in vivo by a synthetic peptide of C-reactive protein, Journal of Leukocyte Biology 1996, 59:397-402.

Deodhar SD et al., Inhibition of Lung Metastases in Mice Bearing a Malignant Fibrosarcoma Treatment with Liposomes Containing Human C-reactive Protein, Cancer Research 1982, 42:5084-5088.
Thomassen MJ, et al., Activation of Human Monocytes and Alveolar Macrophages by a Synthetic Peptide of C-Reactive Protein, Journal of Immunotherapy 1993, 13:1-6.
Zhou P, et al., Human Monocytes Produce Monocyte Chemoattractant Protein 1 (MCP-1) in Response to a Synthetic Peptide Derived from C-Reactive Protein, Clinical Immunology and Immunopathology 1995, 74:84-88.
Du Clos TW. Function of C-reactive protein. *Ann Med* 2000;32:274-8.
Du Clos TW. The interaction of C-reactive protein and serum amyloid P component with nuclear antigens. *Mol Biol Rep* 1996;23:253-60.
Volanakis JE. Human C-reactive protein: expression, structure, and function. *Mol Immunol* 2001;38:189-197.
Gabay C, Roux-Lombard P, de Moerloose P, Dayer J-M, Vischer T, Guerne P-A. Absence of correlation between interleukin 6 and C-reactive protein blood levels in Systemic Lupus Erythematosus compared with Rheumatoid Arthritis. J Rheumatol1993;20:815-821.
Du Clos TW, Mold C. C-reactive protein: an activator of innate immunity and a modulator of adaptive immunity. *Immunol Res* 2004;30:261-78.
Heuertz RM, Dongyuan X, Samols D, Webster RO. Inhibition of C5a des Arg-induced neutrophil alveolitis in transgenic mice expressing C-reactive protein. *Am J Physiol* ;1994;266:L649-L654.
Heuertz RM, Piquette CA, Webster RO. Rabbits with elevated serum C-reactive protein exhibit diminished neutrophil infiltration and vascular permeability in C5a-induced alveolitis. *Am J Pathol* 1993;142:319-328.
Xia D, Samols D. Transgenic mice expressing rabbit C-reactive protein are resistant to endotoxemia. *Proc Natl Acad Sci USA* 1997 ;94:257 5-80.
Mold C, Rodriguez W, Rodic-Polic B, Du Clos TW. C-reactive protein mediates protection from lipopolysaccharide through interactions with Fc gamma R. *J Immunol* 2002;169:7019-25.

(Continued)

*Primary Examiner* — David Lukton
(74) *Attorney, Agent, or Firm* — Henry D. Coleman; R. Neil Sudol; William J. Sapone

(57) ABSTRACT

The present invention relates to the use of C-reactive protein, its mutants, metabolites and polypeptides and related compounds thereof for the treatment of various disease states and conditions associated with systemic lupus erythematosus (SLE), including lupus of the skin (discoid), systemic lupus of the joints, lungs and kidneys, hematological conditions including hemolytic anemia and low lymphocyte counts, lymphadenopathy and CNS effects including memory loss, seizures and psychosis, among numerous others as otherwise disclosed herein, hi another aspect of the invention, the reduction in the likelihood that a patient who is at risk for an outbreak of a disease state or condition with systemic lupus erythematosus will have an outbreak is an additional aspect of the present invention.

13 Claims, 22 Drawing Sheets

OTHER PUBLICATIONS

Szalai AJ, Nataf S, Hu X-Z, Barnum SR. Experimental allergic encephalomyelitis is inhibited in transgenic mice Expressing human C-reactive protein. *J Immunol* 2002;168;5792-5797.

Gershov D, Kim S, Brot N, Elkon KB. C-reactive protein binds to apoptotic cells, protects the cells from assembly of the terminal complement components, and sustains an antiinflammatory innate immune response: implications for systemic autoimmunity. *J Exp Med* 2000;192:1353-1363.

Mold C, Baca R, Du Clos TW. Serum amyloid P component and C-reactive protein opsonize apoptotic cells for phagocytosis through Fcγ receptors. *J Autoimmun* 2002;19:147-54.

Du Clos TW, Zlock LT, Hicks PS, Mold C. Decreased autoantibody levels and enhanced survival of (NZBxNZW) F1 mice treated with C-reactive protein. *Clin Immunol Immunopathol* 1994;70:22-7.

Szalai AJ, Weaver CT, McCrory MA, van Ginkel FW, Reiman RM, Kearney JF, Marion TN, Volanakis JE. Delayed lupus onset in (NZBxNZW)FI mice expressing a human C-reactive protein transgene. *Arthritis Rheum* 2003;48:1602-11.

Rodriguez W, Mold C, Kataranovski M, Hutt J, Marnell LL, Du Clos TV Reversal of ongoing proteinuria in autoimmune mice by treatment with C-reactive protein. *Arthritis Rheum* 2005;52:642650.

Theofilopoulos AN, Dixon FJ. Murine models of systemic lupus erythematosus *Adv Immunol* 1985;37:269-391.

Du Clos TW. C-reactive protein reacts with the U1 small nuclear ribonucleoprotein. *J Immunol* 1989;143:2553-9.

van Rooijen N, Sanders A. Liposome mediated depletion of macrophages: mechanism of action, preparation of liposomes and applications *J Immunol Methods* 1994;174:83-93.

Du Clos TW, Volzer MA, Hahn FF, Mao R, Mold C, Searles RP. Chromatin clearance in C57BU10 mice: interaction with heparan sulphate proteoglycans and receptors on Kupffer cells. *Clin Exp Immunol* 1999;117:403-11.

Oldenhove G, de Heusch M, Urbain-Vansanten G, Urbain J, Maliszewski C, Leo 0, Moser M. CD4+ CD25+ regulatory T cells control T helper cell type 1 responses to foreign antigens induced by mature dendritic cells in vivo. *J Exp Med* 2003;199:259-66.

Rubin RL. Enzyme-linked immunosorbent assay for anti-DNA and antihistone antibodies. In: Rose NR, Friedman H, Fahey JL, editors. Manual of Clinical Laboratory Immunology. Washington: ASM; 1986. p. 744-749.

Kikawada E, Lenda DM, Kelley VR. IL-12 deficiency in MRL-Faslpr) mice delays nephritis and intrarenal IFN-gamma expression, and diminishes systemic pathology. *J Immunol* 2003;170:3915-25.

Smeenk RJ, Brinkman K, van den Brink HG, Westgeest AA. Reaction patterns of monoclonal antibodies to DNA. *J Immunol* 1988;140:3786 92.

McHugh RS, Shevach EM. Cutting edge: depletion of CD4+CD25+ regulatory T cells is necessary, but not sufficient, for induction of organ-specific autoimmune disease. *J Immunol* 2002;168:597983.

Du Clos T V C-reactive protein as a regulator of autoimmunity and inflammation. *Arthritis Rheum* 2003;48:1475-7.

Christensen SR, Kashgarian M, Alexopoulou L, Flavell RA, Akira S, Shlomchik MJ. Toll-like receptor 9 controls anti-DNA autoantibody production in murine lupus. *J Exp Med* 2005;202:321-331.

Zhou T, Bluethmann H, Eldridge J, Berry K, Mountz JD. Origin of CD4-CD8-B220+ T cells in MRL-lpr/lpr mice. Clues from a T cell receptor beta transgenic mouse. *J Immunol* 1993;150:3651-67.

Tesch GH, Maifert S, Schwarting A, Rollins BJ, Kelley VR. Monocyte chemoattractant protein 1-dependent leukocytic infiltrates are responsible for autoimmune disease in MRL-*Faslpr*) mice. *J Exp Med* 1999;190:1813-24.

Walport MJ. Lupus, DNase and defective disposal of cellular debris. *Nat Genet* 2000;25:1356.

Kim SJ, Gershov D, Ma X, Brot N, Elkon KB. Opsonization of apoptotic cells and its effect on macrophage and T cell immune responses. *Ann NY Acad Sci* 2003;987;68-78.

Ehrenstein MR, Cook HT, Neuberger MS. Deficiency in serum immunoglobulin IgM predisposes to development of IgG autoantibodies. *J Exp Med* 2000;191:1253-8.

Boes M, Schmidt T, Linkemann K, Beaudette BC, Marshak-Rothstein A, Chen J. Accelerated development of IgG autoantibodies and autoimmune disease in the absence of secreted IgM. *Proc Natl Acad Sci USA* 2000;97:1184-9.

Botto M, Walport W. Clq, autoimmunity and apoptosis. *Immunobiology* 2002;205:395-406.

Clynes R, Dumitru C, Ravetch JV. Uncoupling of immune complex formation and kidney damage in autoimmune glomerulonephritis. *Science* 1998;279:1052-1054.

Balomenos D, Rumold R, Theofilopoulos AN. Interferon-gamma is required for lupus-like disease and lymphoaccumulation in MRL-lpr mice. *J Clin Invest* 1998;101:364-71.

Heuertz RM, Xia D, Samols D, Webster RD. Inhibition of C5a des Arg-induced neutrophil alveolitis in transgenic mice expressing C-reactive protein. *Am J Physiol* 1994;266:L649-L654.

Baltz ML, Rowe IF, Pepys MB. In vivo turnover studies of C-reactive protein. *Clin Exp Immunol* 1985;59:243-50.

Hutchinson WL, Noble GE, Hawkins PN, Pepys MB. The pentraxins, C-reactive protein and serum amyloid P component, are cleared and catabolized by hepatocytes in vivo. *J Clin Invest* 1994;94:1390-1396.

Carvalho-Pinto CE, Garcia MI, Mellado M, Rodriguez-Frade JM, Martin-Caballero J, Flores J, Martinez AC, Balomenos D. Autocrine production of IFN-gamma by macrophages controls their recruitment to kidney and the development of glomerulonephritis in MRL11pr mice. *J Immunol* 2002;169:1058-67.

Groux H, O'Garra A, Bigler M, Rouleau M, Antonenko S, de Vries JE, Roncarolo MG. A CD4+ T-cell subset inhibits antigen-specific T-cell responses and prevents colitis. *Nature* 1997;389:737-42.

Hahn, B. H. 2002. An overview of the pathogenesis of systemic lupus erythematosus. In *Dubois' Lupus Erythematosus*. D. J. Wallace, and B. H. Hahn, eds. Lippincott Williams and Wilkins, Philadelphia, PA. 87-96.

Gescuk, B. D., and J. C. Davis, Jr. 2002. Novel therapeutic agents for systemic lupus erythematosus. *Current Opinion in Rheumatology* 14:515-521.

Karpouzas, G. A., and B. H. Hahn. 2003. Systemic lupus erythematosus. In *Targeted Therapies in Rheumatology*. J. S. Smolen, and P. E. Lipsky, eds. Martin Dunitz, London. 563-581.

Bisoendial, R. J., J. J. Kastelein, J. H. Levels, J. J. Zwaginga, B. van den Bogaard, P. H. Reitsma, J. C. Meijers, D. Hartman, M. Levi, and E. S. Stroes. 2005. Activation of Inflammation and Coagulation After Infusion of C-Reactive Protein in Humans. *Circ Res* 96:714-716.

Du Clos, T. W. 2000. Function of C-reactive protein. *Annals of Medicine* 32:274-278.

Volanakis, J. E. 2001. Human C-reactive protein: expression, structure, and function. *Molecular Immunology* 38:189-197.

Du Clos, T. W., and C. Mold. 2004. C-reactive protein: an activator of innate immunity and a modulator of adaptive immunity. *Immunol Res* 30:261-278.

Du Clos, T. W. 1996. The interaction of C-reactive protein and serum amyloid P component with nuclear antigens. *Molecular Biology Reports* 23:253-260.

Du Clos, T. W., L. T. Zlock, P. S. Hicks, and C. Mold. 1994. Decreased autoantibody levels and enhanced survival of (NZBxNZW) F1 mice treated with C-reactive protein. *Clinical Immunology and Immunopathology* 70:22-27.

Szalai, A. J., C. T. Weaver, M. A. McCrory, F. W. van Ginkel, R. M. Reiman, J. F. Kearney, T. N. Marion, and J. E. Volanakis. 2003. Delayed lupus onset in (NZBxNZW)F1 mice expressing a human C-reactive protein transgene. *Arthritis & Rheumatism* 48:1602-1611.

Rodriguez, W., C. Mold, M. Kataranovski, J. Hutt, L. L. Marnell, and T. W. Du Clos. 2005. Reversal of ongoing proteinuria in autoimmune mice by treatment with C-reactive protein. *Arthritis & Rheumatism* 52:642-650.

Rodriguez, W., C. Mold, L. L. Marnell, J. Hutt, G. J. Silverman, D. Tran, and T. W. Du Clos. 2006. Prevention and reversal of nephritis in MRL/lpr mice with a single injection of C-reactive protein. *Arthritis Rheum* 54:325-335.

Kono, D. H., and A. N. Theofilopoulos. 2000. Genetics of systemic autoimmunity in mouse models of lupus. *International Reviews of Immunology*. 19:367-387.

Daikh, D. I., and D. Wofsy. 2001. Cutting edge: reversal of murine lupus nephritis with CTLA4Ig and cyclophosphamide. *Journal of Immunology.* 166:2913-2916.

Lawson, B. R., G. J. Prud'homme, Y. Chang, H. A. Gardner, J. Kuan, D. H. Kono, and A. N. Theofilopoulos. 2000. Treatment of murine lupus with cDNA encoding IFN-gammaR/Fc. *Journal of Clinical Investigation* 106:207-215.

Foell, J., S. Strahotin, S. P. O'Neil, M. M. McCausland, C. Suwyn, M. Haber, P. N. Chander, A. S. Bapat, X. J. Yan, N. Chiorazzi, M. K. Hoffmann, and R. S. Mittler. 2003. CD137 costimulatory T cell receptor engagement reverses acute disease in lupus-prone NZBxNZW F1 mice. *J Clin Invest* 111:1505-1518.

Tesch, G. H., S. Maifert, A. Schwarting, B. J. Rollins, and V. R. Kelley. 1999. Monocyte chemoattractant protein 1-dependent leukocytic infiltrates are responsible for autoimmune disease in MRL-Fas(lpr) mice. *Journal of Experimental Medicine* 190:1813-1824.

Du Clos, T. W. 2003. C-reactive protein as a regulator of autoimmunity and inflammation. *Arthritis Rheum* 48:1475-1477.

Ogden, C. A., and K. B. Elkon. 2005. Single-dose therapy for lupus nephritis: C-reactive protein, nature's own dual scavenger and immunosuppressant. *Arthritis Rheum* 52:378-381.

Walport, M. J. 2000. Lupus, DNase and defective disposal of cellular debris. *Nature Genetics* 25:135-136.

Burlingame, R. W., R. L. Rubin, R. S. Balderas, and A. N. Theofilopoulos. 1993. Genesis and evolution of antichromatin autoantibodies in murine lupus implicates T-dependent immunization with self antigen. *Journal of Clinical Investigation* 91:1687-1696.

Burlingame, R. W., M. L. Boey, G. Starkebaum, and R. L. Rubin. 1994. The central role of chromatin in autoimmune responses to histones and DNA in systemic lupus erythematosus. *Journal of Clinical Investigation* 94:184-192.

Casciola-Rosen, L. A., G. Anhalt, and A. Rosen. 1994. Autoantigens targeted in systemic lupus erythematosus are clustered in two populations of surface structures on apoptotic keratinocytes. *Journal of Experimental Medicine* 179:1317-1330.

Carroll, M. C. 2000. A protective role for innate immunity in autoimmune disease. *Clinical Immunology* 95:S30-38.

Burlingame, R. W., M. A. Volzer, J. Harris, and T. W. Du Clos. 1996. The effect of acute phase proteins on clearance of chromatin from the circulation of normal mice. *Journal of Immunology* 156:4783-4788.

Bickerstaff, M. C., M. Botto, W. L. Hutchinson, J. Herbert, G. A. Tennent, A. Bybee, D. A. Mitchell, H. T. Cook, P. J. Butler, M. J. Walport, and M. B. Pepys. 1999. Serum amyloid P component controls chromatin degradation and prevents antinuclear autoimmunity. *Nat Med* 5:694-697.

Familian, A., B. Zwart, H. G. Huisman, I. Rensink, D. Roem, P. L. Hordijk, L. A. Aarden, and C. E. Hack. 2001. Chromatin-independent binding of serum amyloid P component to apoptotic cells. *Journal of Immunology* 167:647-654.

Gershov, D., S. Kim, N. Brot, and K. B. Elkon. 2000. C-reactive protein binds to apoptotic cells, protects the cells from assembly of the terminal complement components, and sustains an antiinflammatory innate immune response: implications for systemic autoimmunity. *Journal of Experimental Medicine* 192:1353-1363.

Mold, C., R. Baca, and T. W. Du Clos. 2002. Serum amyloid P component and C-reactive protein opsonize apoptotic cells for phagocytosis through Fcg receptors. *Journal of Autoimmunity* 19:147-154.

Taylor, P. R., A. Carugati, V. A. Fadok, H. T. Cook, M. Andrews, M. C. Carroll, J. S. Savill, P. M. Henson, M. Botto, and M. J. Walport. 2000. A hierarchical role for classical pathway complement proteins in the clearance of apoptotic cells in vivo. *J Exp Med* 192:359-366.

Crow, M. K., K. A. Kirou, and J. Wohlgemuth. 2003. Microarray analysis of interferon-regulated genes in SLE. *Autoimmunity* 36:481-490.

Baechler, E. C., P. K. Gregersen, and T. W. Behrens. 2004. The emerging role of interferon in human systemic lupus erythematosus. *Curr. Opin. Immunol.* 16:801-807.

Ronnblom, L., M. L. Eloranta, and G. V. Alm. 2006. The type I interferon system in systemic lupus erythematosus. *Arthritis Rheum* 54:408-420.

Bave, U., M. Magnusson, M. L. Eloranta, A. Perers, G. V. Alm, and L. Ronnblom. 2003. Fc gamma RIIa is expressed on natural IFN-alpha-producing cells (plasmacytoid dendritic cells) and is required for the IFN-alpha production induced by apoptotic cells combined with lupus IgG. *J Immunol* 171:3296-3302.

Martin, D. A., and K. B. Elkon. 2005. Autoantibodies make a U-turn: the toll hypothesis for autoantibody specificity. *J. Exp. Med.* 202:1465-1469.

Boule, M. W., C. Broughton, F. Mackay, S. Akira, A. Marshak-Rothstein, and I. R. Rifkin. 2004. Toll-like receptor 9-dependent and -independent dendritic cell activation by chromatin-immunoglobulin G complexes. *J. Exp. Med.* 199:1631-1640.

Xia, D., and D. Samols. 1997. Transgenic mice expressing rabbit C-reactive protein are resistant to endotoxemia. *Proc Natl Acad Sci U S A* 94:2575-2580.

Mold, C., W. Rodriguez, B. Rodic-Polic, and T. W. Du Clos. 2002. C-reactive protein mediates protection from lipopolysaccharide through interactions with Fc gamma R. *J. Immunol.* 169:7019-7025.

Ahmed, N., R. Thorley, D. Xia, D. Samols, and R. O. Webster. 1996. Transgenic mice expressing rabbit C-reactive protein exhibit diminished chemotactic factor-induced alveolitis. *American Journal of Respiratory and Critical Care Medicine* 153:1141-1147.

Stein, M. P., C. Mold, and T. W. Du Clos. 2000. C-reactive protein binding to murine leukocytes requires Fc gamma receptors. *J Immunol* 164:1514-1520.

Bharadwaj, D., M. P. Stein, M. Volzer, C. Mold, and T. W. Du Clos. 1999. The major receptor for C-reactive protein on leukocytes is Fcg receptor II. *Journal of Experimental Medicine* 190:585-590.

Sutterwala, F. S., G. J. Noel, P. Salgame, and D. M. Mosser. 1998. Reversal of proinflammatory responses by ligating the macrophage Fcg receptor type I. *Journal of Experimental Medicine* 188:217-222.

Anderson, C. F., and D. M. Mosser. 2002. Biasing immune responses by directing antigen to macrophage Fcg receptors. *J. Immunol.* 168:3697-3701.

Park, S. Y., S. Ueda, H. Ohno, Y. Hamano, M. Tanaka, T. Shiratori, T. Yamazaki, H. Arase, N. Arase, A. Karasawa, S. Sato, B. Ledermann, Y. Kondo, K. Okumura, C. Ra, and T. Saito. 1998. Resistance of Fc receptor-deficient mice to fatal glomerulonephritis. *J. Clin. Invest.* 102:1229-1238.

Tarzi, R. M., K. A. Davies, M. G. Robson, L. Fossati-Jimack, T. Saito, M. J. Walport, and H. T. Cook. 2002. Nephrotoxic nephritis is mediated by Fcg receptors on circulating leukocytes and not intrinsic renal cells. *Kidney International* 62:2087-2096.

Kaneko, Y., F. Nimmerjahn, M. P. Madaio, and J. V. Ravetch. 2006. Pathology and protection in nephrotoxic nephritis is determined by selective engagement of specific Fc receptors. *J Exp Med.* 203:789-797.

van Rooijen, N., and A. Sanders. 1994. Liposome mediated depletion of macrophages: mechanism of action, preparation of liposomes and applications. *J. Immunol. Meth.* 174:83-93.

Du Clos, T. W., M. A. Volzer, F. F. Hahn, R. Xiao, C. Mold, and R. P. Searles. 1999. Chromatin clearance in C57B1/10 mice: interaction with heparan sulphate proteoglycans and receptors on Kupffer cells. *Clin Exp Immunol* 117:403-411.

Kikawada, E., D. M. Lenda, and V. R. Kelley. 2003. IL-12 deficiency in MRL-Fas(lpr) mice delays nephritis and intrarenal IFN-gamma expression, and diminishes systemic pathology. *J Immunol* 170:3915-3925.

Lenda, D. M., E. Kikawada, E. R. Stanley, and V. R. Kelley. 2003. Reduced macrophage recruitment, proliferation, and activation in colony-stimulating factor-1-deficient mice results in decreased tubular apoptosis during renal inflammation. *J Immunol* 170:3254-3262.

Timoshanko, J. R., A. R. Kitching, Y. Iwakura, S. R. Holdsworth, and P. G. Tipping. 2004. Leukocyte-derived interleukin-1beta interacts with the renal interleukin-1 receptor I to promote renal tumor necrosis factor and glomerular injury in murine crescentic glomerulonephritis. *Am J Pathol* 164:1967-1977.

Hasegawa, H., M. Kohno, M. Sasaki, A. Inoue, M. R. Ito, M. Terada, K. Hieshima, H. Maruyama, J. Miyazaki, O. Yoshie, M. Nose, and S. Fujita. 2003. Antagonist of monocyte chemoattractant protein 1 ameliorates the initiation and progression of lupus nephritis and renal vasculitis in MRL/lpr mice. *Arthritis Rheum.* 48:2555-2566.

Shimizu, S., H. Nakashima, K. Masutani, Y. Inoue, K. Miyake, M. Akahoshi, Y. Tanaka, K. Egashira, H. Hirakata, T. Otsuka, and M. Harada. 2004. Anti-monocyte chemoattractant protein-1 gene therapy attenuates nephritis in MRL/lpr mice. *Rheumatology (Oxford)* 43:1121-1128.

Noris, M., S. Bernasconi, F. Casiraghi, S. Sozzani, E. Gotti, G. Remuzzi, and A. Mantovani. 1995. Monocyte chemoattractant protein-1 is excreted in excessive amounts in the urine of patients with lupus nephritis. *Lab. Invest.* 73:804-809.

Chan, R. W., F. M. Lai, E. K. Li, L. S. Tam, T. Y. Wong, C. Y. Szeto, P. K. Li, and C. C. Szeto. 2004. Expression of chemokine and fibrosing factor messenger RNA in the urinary sediment of patients with lupus nephritis. *Arthritis Rheum* 50:2882-2890.

Du Clos, T. W. 1989. C-reactive protein reacts with the U1 small nuclear ribonucleoprotein. *Journal of Immunology* 143:2553-2559.

Kilpatrick, J. M., and J. E. Volanakis. 1991. Molecular genetics, structure, and function of C-reactive protein. *Immunol Res* 10:43-53.

Russell, A. I., D. S. Cunninghame Graham, C. Shepherd, C. A. Roberton, J. Whittaker, J. Meeks, R. J. Powell, D. A. Isenberg, M. J. Walport, and T. J. Vyse. 2004. Polymorphism at the C-reactive protein locus influences gene expression and predisposes to systemic lupus erythematosus. *Human Molecular Genetics* 13:137-147.

Ku, N. O., and R. F. Mortensen. 1993. Cloning and tissue-specific expression of the gene for mouse C-reactive protein. *Biochem. J.* 295 (Pt 2):379-386.

Marnell, L., C. Mold, M. A. Volzer, R. W. Burlingame, and T. W. Du Clos. 1995. Expression and radiolabeling of human C-reactive protein in baculovirus-infected cell lines and Trichoplusia ni larvae. *Protein Expr Purif* 6:439-446.

Siboo, R., and E. Kulisek. 1978. A fluorescent immunoassay for quantification of C-reactive protein. *J.Immunol.Meth.* 23:59-67.

Hutchinson, W. L., G. E. Noble, P. N. Hawkins, and M. B. Pepys. 1994. The pentraxins, C-reactive protein and serum amyloid P component, are cleared and catabolized by hepatocytes in vivo. *J.Clin. Invest.* 94:1390-1396.

Vigushin, D. M., M. B. Pepys, and P. N. Hawkins. 1993. Metabolic and scintigraphic studies of radioiodinated human C-reactive protein in health and disease. *J. Clin. Invest.* 91:1351-1357.

Katre, N. V. 1990. Immunogenicity of recombinant IL-2 modified by covalent attachment of polyethylene glycol. *J. Immunol.* 144:209-213.

Daro, E., B. Pulendran, K. Brasel, M. Teepe, D. Pettit, D. H. Lynch, D. Vremec, L. Robb, K. Shortman, H. J. McKenna, C. R. Maliszewski, and E. Maraskovsky. 2000. Polyethylene glycol-modified GM-CSF expands CD11b(high)CD11c(high) but notCD11b(low)CD11c(high) murine dendritic cells in vivo: a comparative analysis with Flt3 ligand. *J. Immunol.* 165:49-58.

Cunnane, G., O. T. Chan, G. Cassafer, S. Brindis, E. Kaufman, T. S. Yen, and D. I. Daikh. 2004. Prevention of renal damage in murine lupus nephritis by CTLA-4Ig and cyclophosphamide. *Arthritis Rheum* 50:1539-1548.

Qiao, J. H., L. W. Castellani, M. C. Fishbein, and A. J. Lusis. 1993. Immune-complex-mediated vasculitis increases coronary artery lipid accumulation in autoimmune-prone MRL mice. *Arterioscler. Thromb.* 13:932-943.

Ridker, P. M. 2003. Clinical application of C-reactive protein for cardiovascular disease detection and prevention. *Circulation* 107:363-369.

Albert, M. A., R. J. Glynn, and P. M. Ridker. 2003. Plasma concentration of C-reactive protein and the calculated Framingham Coronary heart disease risk score. *Circulation* 108:161-165.

Hirschfield, G. M., J. R. Gallimore, M. C. Kahan, W. L. Hutchinson, C. A. Sabin, G. M. Benson, A. P. Dhillon, G. A. Tennent, and M. B. Pepys. 2005. Transgenic human C-reactive protein is not proatherogenic in apolipoprotein E-deficient mice. *Proc. Natl. Acad. Sci. U. S. A.* 102:8309-8314.

Paul, A., K. W. Ko, L. Li, V. Yechoor, M. A. McCrory, A. J. Szalai, and L. Chan. 2004. C-reactive protein accelerates the progression of atherosclerosis in apolipoprotein E-deficient mice. *Circulation* 109:647-655.

Reifenberg, K., H. A. Lehr, D. Baskal, E. Wiese, S. C. Schaefer, S. Black, D. Samols, M. Torzewski, K. J. Lackner, M. Husmann, M. Blettner, and S. Bhakdi. 2005. Role of C-reactive protein in atherogenesis: can the apolipoprotein E knockout mouse provide the answer? *Arterioscler. Thromb. Vasc. Biol.* 25:1641-1646.

Pepys, M. B., P. N. Hawkins, M. C. Kahan, G. A. Tennent, J. R. Gallimore, D. Graham, C. A. Sabin, A. Zychlinsky, and J. de Diego. 2005. Proinflammatory effects of bacterial recombinant human C-reactive protein are caused by contamination with bacterial products, not by C-reactive protein itself. *Circ Res* 97:e97-103.

Taylor, K. E., J. C. Giddings, and C. W. van den Berg. 2005. C-Reactive Protein-Induced In Vitro Endothelial Cell Activation Is an Artefact Caused by Azide and Lipopolysaccharide. *Arterioscler Thromb Vasc Biol.* 25:1225-1230.

Pepys, M. B., G. M. Hirschfield, G. A. Tennent, J. R. Gallimore, M. C. Kahan, V. Bellotti, P. N. Hawkins, R. M. Myers, M. D. Smith, A. Polara, A. J. Cobb, S. V. Ley, J. A. Aquilina, C. V. Robinson, I. Sharif, G. A. Gray, C. A. Sabin, M. C. Jenvey, S. E. Kolstoe, D. Thompson, and S. P. Wood. 2006. Targeting C-reactive protein for the treatment of cardiovascular disease. *Nature* 440:1217-1221.

Griselli, M., J. Herbert, W. L. Hutchinson, K. M. Taylor, M. Sahail, T. Drausz, and M. B. Pepys. 1999. C-reactive protein and complement are important mediators of tissue damage in acute myocardial infarction. *Journal of Experimental Medicine* 190:1733-1739.

Mold, C., S. Nakayama, T. J. Holzer, H. Gewurz, and T. W. Du Clos. 1981. C-reactive protein is protective against *Streptococcus pneumoniae* infection in mice. *Journal of Experimental Medicine* 154:1703-1708.

Mold, C., B. Rodic-Polic, and T. W. Du Clos. 2002. Protection from *Streptococcus pneumoniae* infection by C-reactive protein and natural antibody requires complement but not Fc gamma receptors. *J Immunol* 168:6375-6381.

Bang, R., L. Marnell, C. Mold, M. P. Stein, K. T. Du Clos, C. Chivington-Buck, and T. W. Du Clos. 2005. Analysis of binding sites in human C-reactive protein for Fcgamma RI, Fcgamma RIIa and C1q by site-directed mutagenesis. *J Biol Chem*. 280:25095-25102.

Agrawal, A., M. J. Simpson, S. Black, M. P. Carey, and D. Samols. 2002. A C-reactive protein mutant that does not bind to phosphocholine and pneumococcal C-polysaccharide. *J Immunol* 169:3217-3222.

Agrawal, A., A. K. Shrive, T. J. Greenhough, and J. E. Volanakis. 2001. Topology and structure of the C1q-binding site on C-reactive protein. *Journal of Immunology* 166:3998-4004.

Agrawal, A., Y. Xu, D. Ansardi, K. J. Macon, and J. E. Volanakis. 1992. Probing the phosphocholine-binding site of human C-reactive protein by site-directed mutagenesis. *J.Biol.Chem.* 267:25352-25358.

Du Clos, T. W., L. T. Zlock, and R. L. Rubin. 1988. Analysis of the binding of C-reactive protein to histones and chromatin. *J Immunol* 141:4266-4270.

Chang, M.-K., C. J. Binder, M. Torzewski, and J. L. Witztum. 2002. C-reactive aprotein binds to both oxidized LDL and apoptotic cells through recognition of a common ligand: Phosphorylcholine of oxidized phospholipids. *PNAS* 99:13043-13048.

Du Clos, T. W., L. T. Zlock, and L. Marnell. 1991. Definition of a C-reactive protein binding determinant on histones. *J Biol Chem* 266:2167-2171.

Bolland, S., and J. V. Ravetch. 2000. Spontaneous autoimmune disease in Fc(gamma)RIIB-deficient mice results from strain-specific epistasis. *Immunity*. 13:277-285.

Lagrand, W. K., H. W. M. Niessen, G.-J. Wolbink, L. H. Jaspars, C. A. Visser, F. W. A. Verheugt, C. J. L. M. Meijer, and C. E. Hack. 1997. C-reactive protein colocalizes with complement in human hearts during acute myocardial infarction. *Circ.* 95:97-103.

Ehrenstein, M. R., H. T. Cook, and M. S. Neuberger. 2000. Deficiency in serum immunoglobulin (Ig)M predisposes to development of IgG autoantibodies. *J Exp Med* 191:1253-1258.

Peng, Y., R. Kowalewski, S. Kim, and K. B. Elkon. 2005. The role of IgM antibodies in the recognition and clearance of apoptotic cells. *Mol Immunol* 42:781-787.

Nimmerjahn, F., and J. V. Ravetch. 2006. Fcgamma receptors: old friends and new family members. *Immunity* 24:19-28.

Nimmerjahn, F., P. Bruhns, K. Horiuchi, and J. V. Ravetch. 2005. FcgammaRIV: a novel FcR with distinct IgG subclass specificity. *Immunity* 23:41-51.

Ravetch.J.V., and Lanier.L.L. 2000. Immune inhibitory receptors. *Science* 290:84-89.

Fadok, V. A., D. L. Bratton, and P. M. Henson. 2001. Phagocyte receptors for apoptotic cells: recognition, uptake, and consequences. *Journal of Clinical Investigation* 108:957-962.

Mold, C., H. Gewurz, and T. W. Du Clos. 1999. Regulation of complement activation by C-reactive protein. *Immunopharmacology* 42:23-30.

Jewell, W. S., L. L. Marnell, L. A. Rokeach, and T. W. Du Clos. 1993. C-reactive protein (CRP) binding to the Sm-D protein of smRNPS. Identification of a short polypeptide binding region. *Molecular Immunology* 30:701-708.

Riemekasten, M., K. Trebeljahr, H. Hausdorf, and H. Burmester. 1998. A novel epitope on the C-terminus of SmD1 is recognized by the majority of sera from patients with systemic lupus erythematosus. *Journal of Clinical Investigation* 102:754-763.

Riemekasten, G., A. Kawald, C. Weiss, A. Meine, J. Marell, R. Klein, B. Hocher, C. Meisel, G. Hausdorf, R. Manz, T. Kamradt, G.-R. Burmester, and F. Hiepe. 2001. Strong acceleration of murine lupus by injection of the SmD183-119 peptide. *Arthritis & Rheumatism* 44:2435-2445.

Reuter, R., and R. Lührmann. 1986. Immunization of mice with purified U1 small nuclear ribonucleoprotein (RNP) induces a pattern of antibody specificities characteristic of the anti-Sm and anti-RNP autoimmune response of patients with lupus erythematosus, as measured by monoclonal antibodies. *Proc. Natl. Acad. Sci. USA* 83:8689-8693.

Nakayama, S., T. W. Du Clos, H. Gewurz, and C. Mold. 1984. Inhibition of antibody responses to phosphocholine by C-reactive protein. *J Immunol* 132:1336-1340.

Mevorach, D., J. L. Zhou, X. Song, and K. B. Elkon. 1998. Systemic exposure to irradiated apoptotic cells induces autoantibody production. *J Exp Med* 188:387-392.

Chang, M. K., C. J. Binder, Y. I. Miller, G. Subbanagounder, G. J. Silverman, J. A. Berliner, and J. L. Witztum. 2004. Apoptotic cells with oxidation-specific epitopes are immunogenic and proinflammatory. *J Exp Med* 200:1359-1370.

Fadok, V. A., D. L. Bratton, A. Konowal, P. W. Freed, J. Y. Westcott, and P. M. Henson. 1998. Macrophages that have ingested apoptotic cells in vitro inhibit proinflammatory cytokine production through autocrine/paracrine mechanisms involving TGFb, PGE2, and PAF. *Journal of Clinical Investigation* 101:890-898.

Du Clos, T. W., R. L. Rubin, and E. M. Tan. 1986. Monoclonal antibody for DNA measurement in biological fluids. *J Immunol Methods* 88:185-192.

Duramad, O., K. L. Fearon, J. H. Chan, H. Kanzler, J. D. Marshall, R. L. Coffman, and F. J. Barrat. 2003. IL-10 regulates plasmacytoid dendritic cell response to CpG-containing immunostimulatory sequences. *Blood* 102:4487-4492.

Bave, U., H. Vallin, G. V. Alm, and L. Ronnblom. 2001. Activation of natural interferon-alpha producing cells by apoptotic U937 cells combined with lupus IgG and its regulation by cytokines. *J Autoimmun* 17:71-80.

Means, T. K., E. Latz, F. Hayashi, M. R. Murali, D. T. Golenbock, and A. D. Luster. 2005. Human lupus autoantibody-DNA complexes activate DCs through cooperation of CD32 and TLR9. *J Clin Invest* 115:407-417.

Szalai, A. J., S. Nataf, X.-Z. Hu, and S. R. Barnum. 2002. Experimental allergic encephalomyelitis is inhibited in transgenic mice expressing human C-reactive protein. *Journal of Immunology* 168:5792-5797.

Izui, S., P.J. McConahey and F. J. Dixon. 1978. Increased spontaneous polyclonal activation of B lymphocytes in mice with spontaneous autoimmune disease. *Journal of Immunology* 121:2213-2219.

Du Clos, T. W., E. M. Tan, and F. J. Dixon. 1986. Ultraviolet light irradiation of NZB/W mice produces a dramatic fall in levels of autoantibodies. *Arthritis and Rheumatism* 29:S59.

Lenda, D. M., E. R. Stanley, and V. R. Kelley. 2004. Negative role of colony-stimulating factor-1 in macrophage, T cell, and B cell mediated autoimmune disease in MRL-Fas(lpr) mice. *J Immunol* 173:4744-4754.

Carvalho-Pinto, C. E., M. I. Garcia, M. Mellado, J. M. Rodriguez-Frade, J. Martin-Caballero, J. Flores, A. C. Martinez, and D. Balomenos. 2002. Autocrine production of IFN-gamma by macrophages controls their recruitment to kidney and the development of glomerulonephritis in MRL/lpr mice. *Journal of Immunology* 169:1058-1067.

Geissmann, F., S. Jung, and D. R. Littman. 2003. Blood monocytes consist of two principal subsets with distinct migratory properties. *Immunity* 19:71-82.

Serbina, N. V., and E. G. Pamer. 2006. Monocyte emigration from bone marrow during bacterial infection requires signals mediated by chemokine receptor CCR2. *Nat Immunol* 7:311-317.

Goodyear, C. S., and G. J. Silverman. 2003. Death by a B cell superantigen: In vivo VH-targeted apoptotic supraclonal B cell deletion by a Staphylococcal Toxin. *J Exp Med* 197:1125-1139.

Feral, C. C., D. M. Rose, J. Han, N. Fox, G. J. Silverman, K. Kaushansky, and M. H. Ginsberg. 2006. Blocking the {alpha}4 integrin{alpha}paxillin interaction selectively impairs mononuclear leukocyte recruitment to an inflammatory site. *J. Clin. Invest.* 116:715-723.

Foussat, A., F. Cottrez, V. Brun, N. Fournier, J. P. Breittmayer, and H. Groux. 2003. A comparative study between T regulatory Type 1 and CD4+CD25+ T cells in the control of inflammation. The complex role of interleukin-10 in autoimmunity. *Journal of Immunology* 171:5018-5026.

Ruprecht, C. R., M. Gattorno, F. Ferlito, A. Gregorio, A. Martini, A. Lanzavecchia, and F. Sallusto. 2005. Coexpression of CD25 and CD27 identifies FoxP3+ regulatory T cells in inflamed synovia. *J Exp Med* 201:1793-1803.

American College of Rheumatology Ad Hoc Committtee on Systemic Lupus Erythematosus Guidelines, Guidelines for Referral and Management of Systemic Lupus Erythematosus in Adults. Arthritis & Rheumatism 1999, 42(9):1785-1796.

American College of Rheumatology Ad Hoc Committtee on Systemic Lupus Erythematosus Guidelines, The American College of Rheumatology Response Criteria for Proliferative and Membranous Renal Disease in Systemic Lupus Erythematosus Clinical Trials. Arthritis & Rheumatism 2006, 54(2):421-432.

Balow JE et al., Maintenance Therapy for Lupus Nephritis—Something Old, Something New. The New England Journal of Medicine 2004, 350(10):1044-1046.

Croker JA et al., SLE: challenges and candidates in human disease. Trends in Immunology 2005, 26(11):580-586.

Ginzler EM et al., Mycophenolate Mofetil or Intravenous Cyclophosphamide for Lupus Nephritis. The New England Journal of Medicine 2005, 353(21):2219-2284.

Mok CC et al. Predictors and Outcome of Renal Flares After Successful Cyclophosphamide Treatment for Diffuse Proliferative Lupus Glomerulonephritis. Arthritis & Rheumatism 2994, 50(8):2559-2568.

Mok CC, Cyclophosphamide for Severe Lupus Nephritis: Where Are We Now? Arthritis & Rheumatism 2004, 50 (12):3748-3750.

McCune WJ, Mycophenolate Mofetil for Lupus Nephritis. The New England Journal of Medicine 2005, 353 (21):2282-2284.

Pisoni CN et al., Mycophenolate mofetil in systemic lupus erythematosus: efficacy and tolerability in 86 patients. The Journal of Rheumatology 2005, 32(6):1047-1052. (Abstract only).

* cited by examiner

FIGURE 1

Complete CRP sequence (SEQ ID No: 1)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

D112N (SEQ ID No: 2)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asn | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 1 (Cont'd)

D112A (SEQ ID No: 3)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Ala | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

H38R (SEQ ID No: 4)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | Arg | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 1 (Cont'd)

D169A (SEQ ID No: 5)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Ala | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Y175L (SEQ ID No: 6)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Leu | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 1 (Cont'd)

L176Q (SEQ ID No: 7)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Gln | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

F66A/E81A (Seq ID No: 8)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Ala | Trp | Ser | Lys | Asp | Ile | Gly |
| Tyr | Ser | Phe | Thr | Val | Gly | Gly | Ser | Ala | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 2 A and B
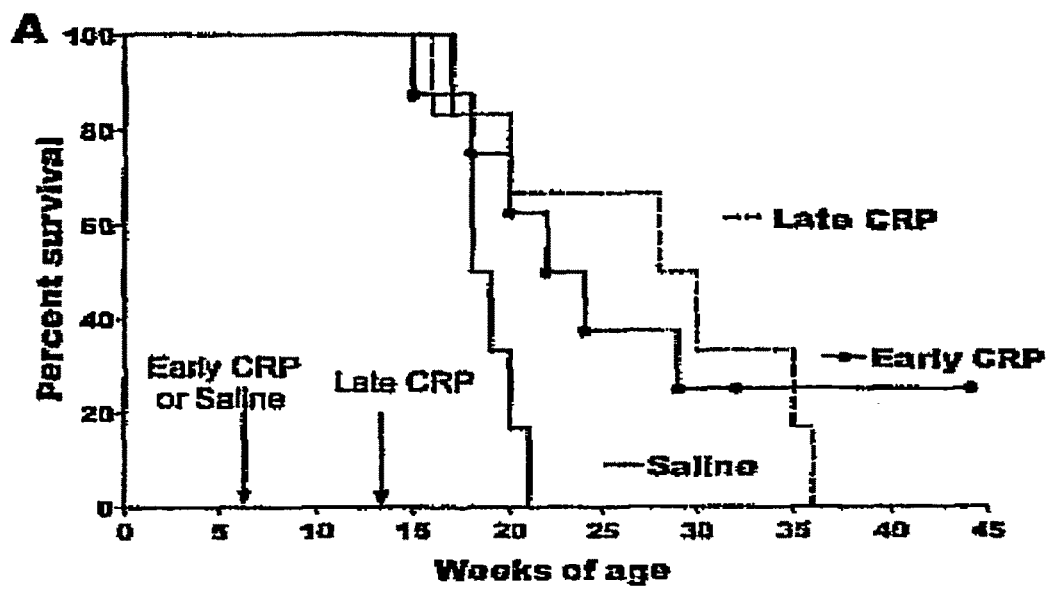
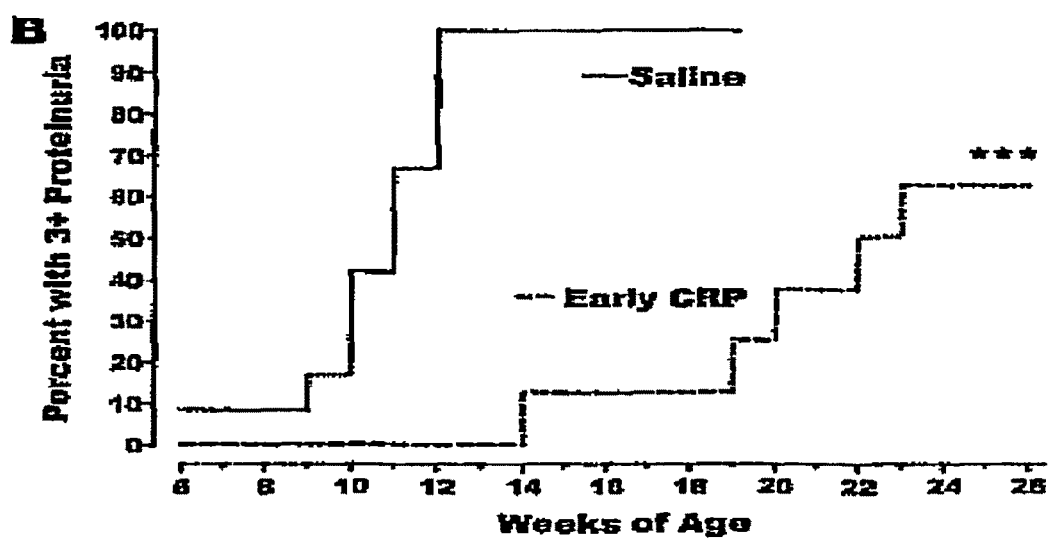

Figure 2 C and D
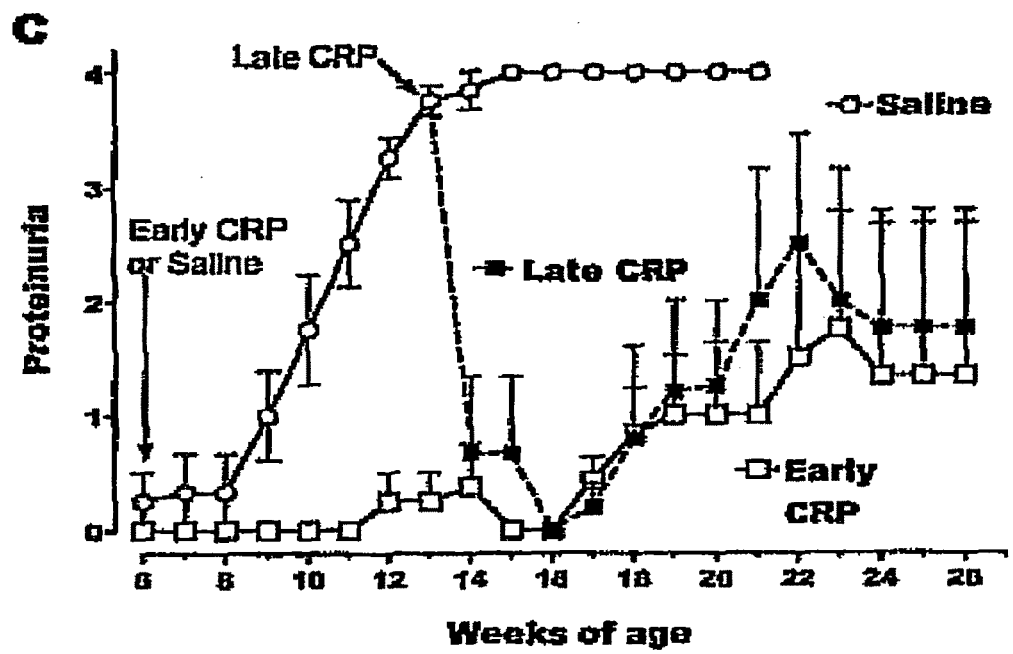
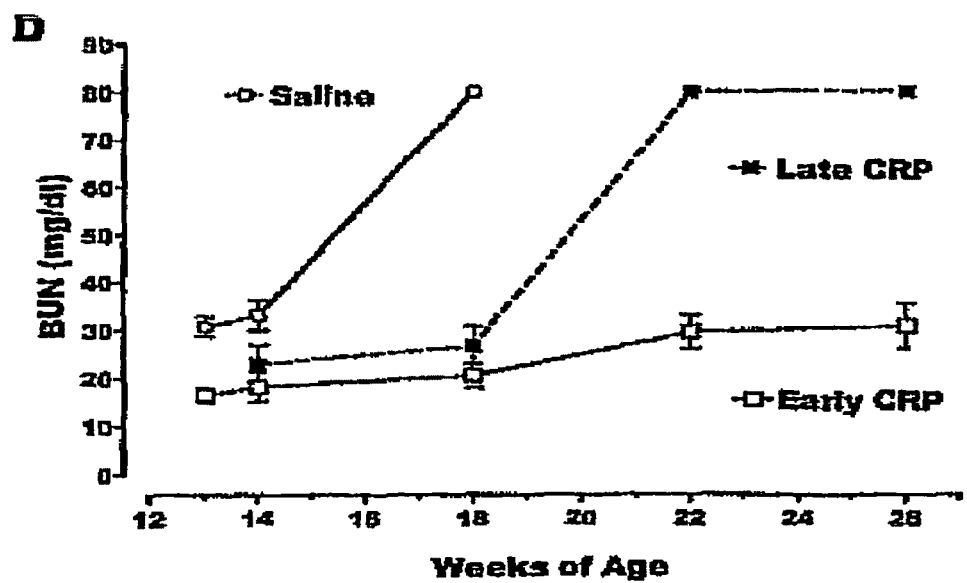

Figure 3 A and B
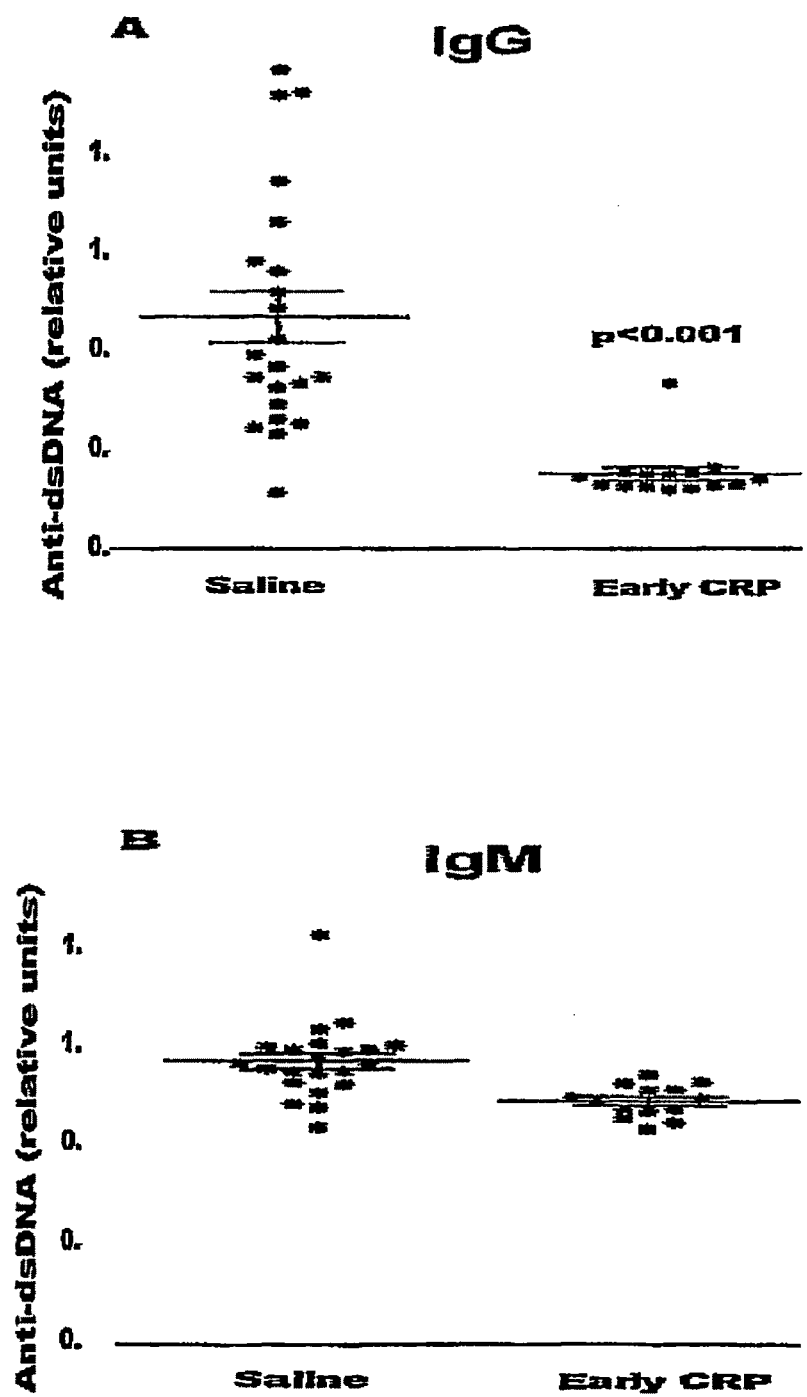

Figure 3 C and D
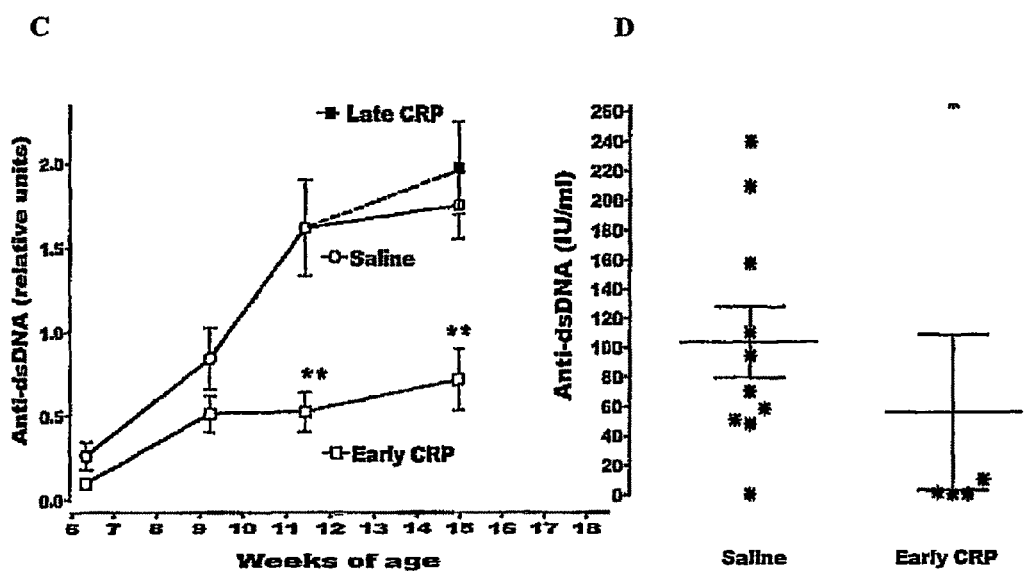

Figure 5 A and B
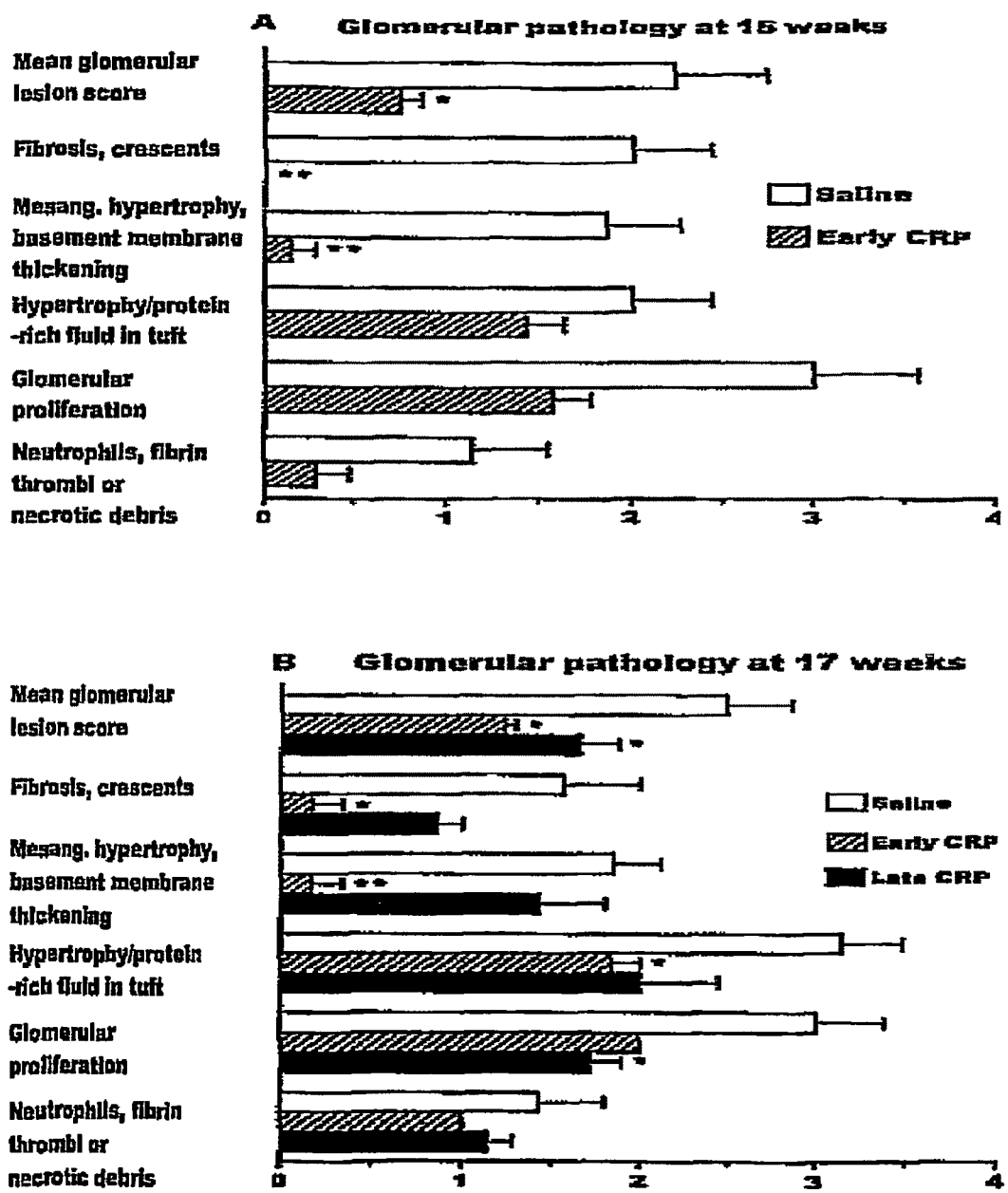

Figure 5 C and D
C
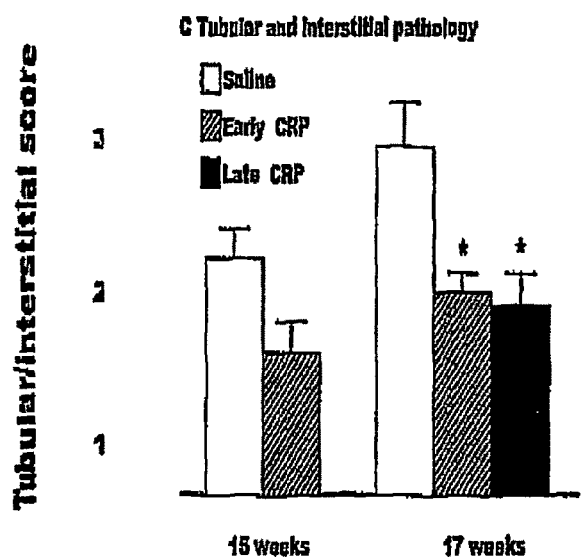
D
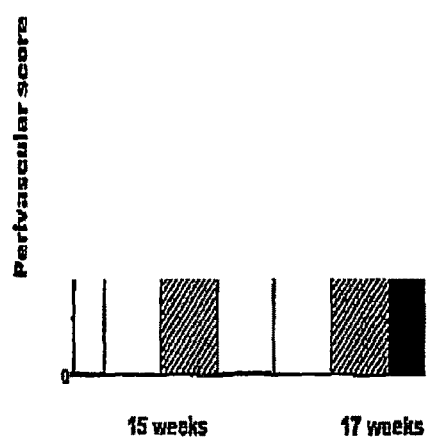

Figure 7 A and B

Figure 8
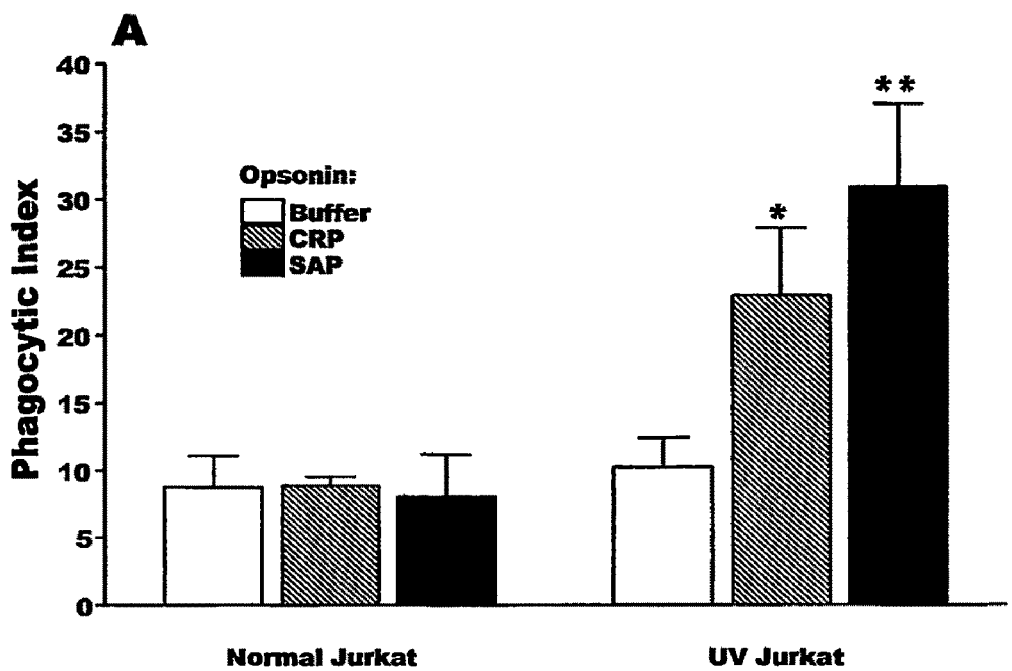
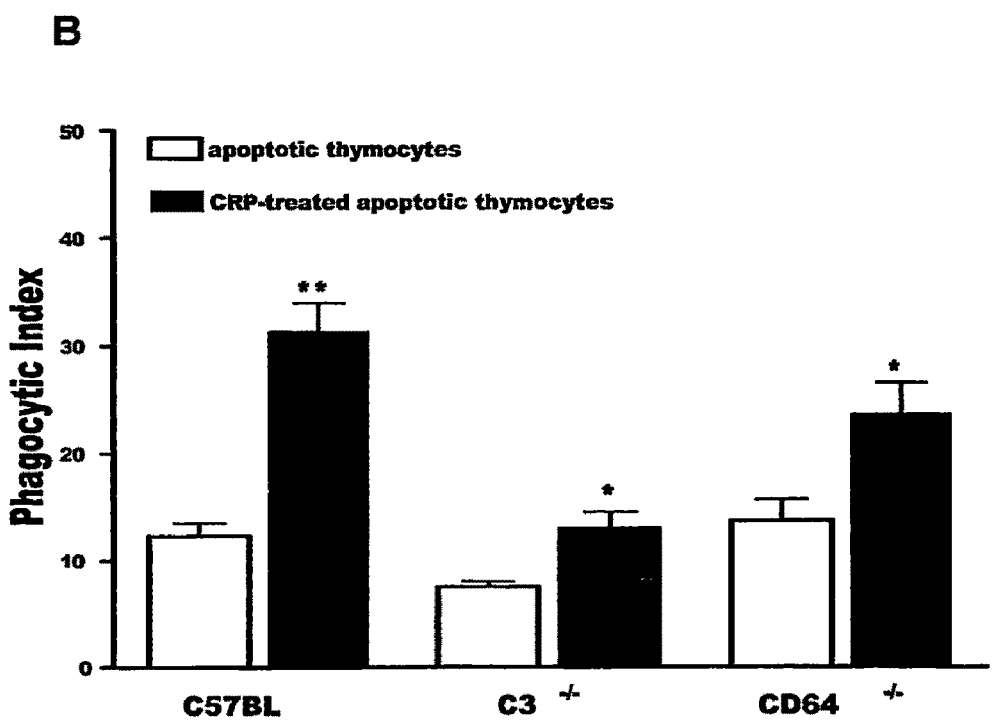

Figure 9
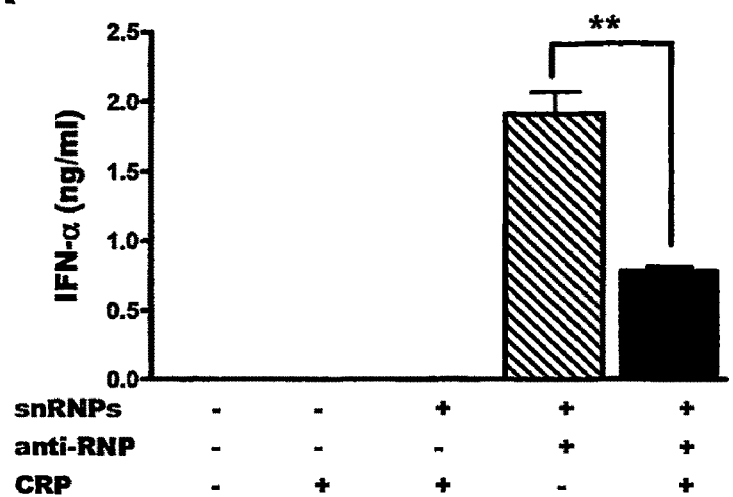
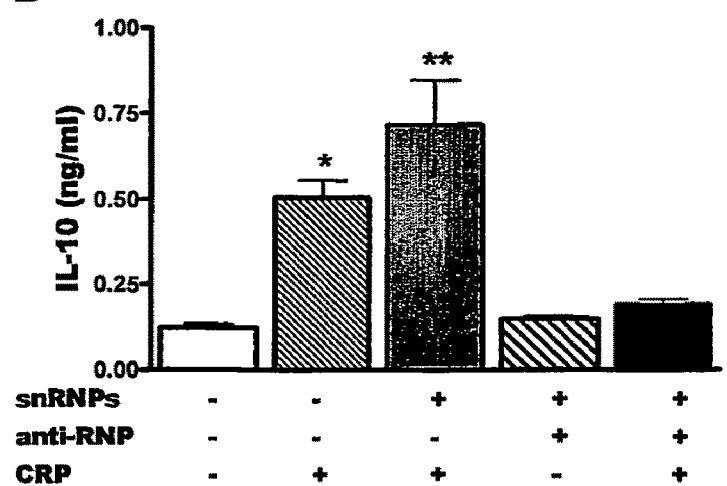

Figure 16
A
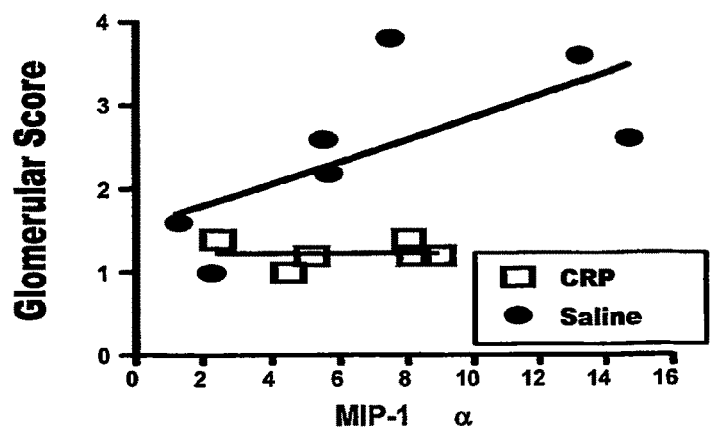
B
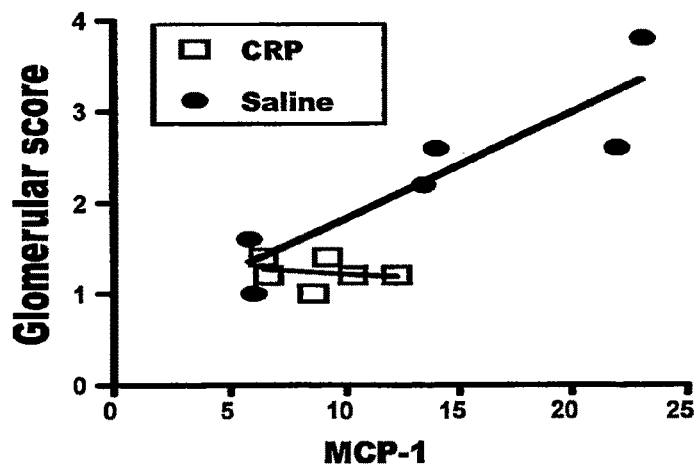
C
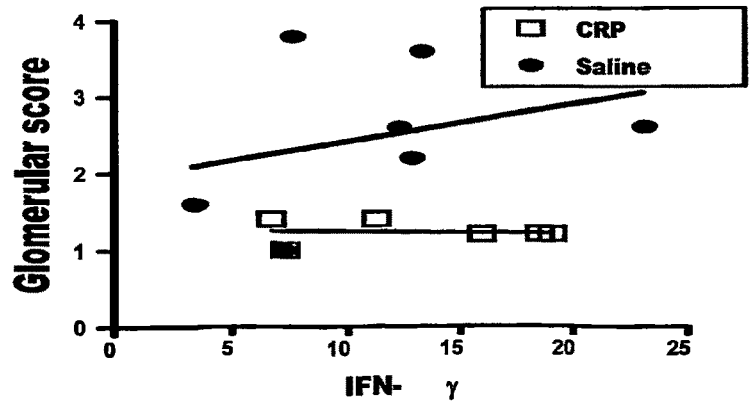

C-REACTIVE PROTEIN AND ITS USE TO TREAT SYSTEMIC LUPUS ERYTHEMATOSUS AND RELATED CONDITIONS

RELATED APPLICATIONS

This application is a national stage entry of PCT/US2006/041583, filed Oct. 26, 2006, which claims priority from provisional application 60/730,013, filed Oct. 26, 2005.

GOVERNMENT SUPPORT

The research related to this invention was supported by the Department of Veterans Affairs and NIH grant AI-28358.

FIELD OF THE INVENTION

The present invention relates to the use of C-reactive protein, its mutants, metabolites and polypeptides and related compounds thereof for the treatment of various disease states and conditions associated with systemic lupus erythematosus (SLE), including lupus of the skin (discoid), systemic lupus of the joints, lungs and kidneys, hematological conditions including hemolytic anemia and low lymphocyte counts, lymphadenopathy and CNS effects, including memory loss, seizures and psychosis, among numerous others as otherwise disclosed herein. In another aspect of the invention, the reduction in the likelihood that a patient who is at risk for an outbreak of a disease state or condition associated with systemic lupus erythematosus will have an outbreak is an additional aspect of the present invention.

BACKGROUND OF THE INVENTION

C-reactive protein (CRP) is a major acute phase reactant, which is produced primarily in the liver in response to infection, inflammation and trauma (1). CRP has been shown to bind to nuclear autoantigens (2). The primary stimulus for CRP production is IL-6 (3). Serum levels of CRP in disease usually correlate with levels of IL-6 in the blood. In SLE, CRP levels do not correlate with serum IL-6 suggesting an abnormal CRP response in patients with SLE (4).

Extensive efforts to discover the single "function" of CRP have instead demonstrated that CRP exhibits different biological activities under different conditions (1, 3). These activities depend on ligand recognition, activation of complement and interactions with receptors (FcγR) I and II. Although CRP may enhance inflammation and ligand clearance through complement activation, one its most important functions appears to be the direct modulation of inflammation through interaction with FcγR (5). Depending on the level and type of FcγR expressed on cells at the site of CRP interaction, the outcome of CRP binding may be either pro- or anti-inflammatory. Under most conditions it is likely that CRP plays an anti-inflammatory and immunomodulatory role in acute inflammation and helps to clear damaged self and foreign materials from the circulation in a non-inflammatory and non-immunogenic manner.

CRP modulates inflammation in a variety of animal models. Heuertz et al first demonstrated that CRP protects rabbits and mice from C5a induced alveolitis (6, 7). CRP also protects mice from lethatity due to lipopolysaccharide (LPS) (8). The ability of CRP to protect mice from LPS was subsequently determined to require FcγR (9). These are acute inflammatory models associated with complement activation and neutrophilic infiltration. However, CRP was also protective in a mouse model of experimental allergic encephalitis (10), a T cell-mediated autoimmune disease.

CRP interacts with nuclear antigens including chromatin and small nuclear ribonuclear protein particles (snRNPs) (reviewed in (2)). In addition, CRP binds to apoptotic cells leading to enhanced phagocytosis and an increase in anti-inflammatory cytokines (11, 12). CRP also influences the course of autoimmune disease in (NZB×NZW)$F_1$ female mice (NZB/W) (13). This effect was attributed to decreased antigenic stimulation and enhanced clearance of nuclear antigens. The protection from nephritis in NZB/W mice was recently confirmed in a transgenic mouse expressing human CRP (14). More recently, we determined that a single injection of CRP provides long-lasting protection from lupus nephritis and reverses ongoing nephritis in NZB/W mice (15). Interestingly, there was no reduction of autoantibodies to nuclear antigens in CRP-treated mice in either of these studies. CRP was also protective in nephrotoxic nephritis (NTN), an immune complex (IC) nephritis model that does not involve autoantibodies (15). As renal disease was markedly decreased in CRP-treated mice without a corresponding decrease in glomerular IgG or C3 deposition, it appears that CRP can reduce the inflammatory response to IC.

Systemic lupus erythematosus (SLE) is a systemic immune complex disease of humans that affects multiple organ systems. The disease is characterized by rashes, arthritis, lung disease, and kidney disease. It occurs mostly in women and usually strikes during young adulthood. Perhaps the most severely affected organ is the kidney, and glomerulonephritis is the major cause of morbidity and mortality in patients with SLE. The current standard treatment for lupus nephritis is the alkylating agent cyclophosphamide, a strong immunosuppressive drug. Although treatment is generally effective, the drug has many side effects including infections, sterility, hair loss, and malignancy.

A wide variety of agents have been used to treat SLE. These agents may act either by interfering with collaborations between B and T lymphocytes, directly eliminating effector cells, or by blocking individual cytokines. Biological agents have had various levels of success in treating animal models of SLE. However, most agents require repeated treatment with high concentrations of monoclonal antibody or protein antagonists.

The most commonly studied animal model of human SLE is the NZB/W female mouse. This mouse shares many features with the human disease including severe proliferative glomerulonephritis, which is the major cause of death in the mice. The mice have high levels of circulating immune complexes (IC), which interact with FcγR in the kidney to induce nephritis. A second mouse model of human SLE is the MRL-$Fas^{lpr}$ mouse (MRL/lpr), which exhibits a more rapid progression of disease than the NZB/W mouse.

The innate immune system plays an important role in autoimmunity. One way in which the innate immune system molecules may affect autoimmunity is through the recognition and clearance of autoantigens released from apoptotic or necrotic cells. Other possible mechanisms for protecting against autoimmune-mediated inflammation include altering the cytokine response to inflammatory stimuli and by redirecting the adaptive immune system.

CRP is the prototypic acute phase reactant in man and a component of the innate immune system. CRP binds to nuclear antigens that are the target of the autoantibodies of patients with SLE as well as to damaged membranes and microbial antigens. CRP activates the classical complement pathway and interacts with phagocytic cells through FcγR. CRP is protective against various inflammatory states including endotoxin shock and inflammatory alveolitis. CRP protection against endotoxin shock requires FcγR and is associated with FcγR-dependent induction of interlukin-10 (IL-10) synthesis by macrophages.

It has been reported that CRP was protective against the accelerated disease in NZB/W mice injected with chromatin. It has also been demonstrated that NZB/W mice transgenic for human CRP had a delayed onset of proteinuria and enhanced survival. The ability of CRP to prolong survival in NZB/W mice has been attributed to increased binding and clearance of autoantigens or immune complexes. However, the ability of CRP to regulate acute inflammation suggests an alternative mechanism for its beneficial effects in SLE.

BRIEF DESCRIPTION OF THE FIGURES

FIG. 1 shows the polypeptide sequences of C-reactive protein and seven mutants (D112N, D112A, H38R, D169A, Y175L, L176O and F66A/E81A) that are useful in the present invention.

FIG. 2 shows that CRP improves the clinical features of disease in MRL11pr mice. Six week old MRU11pr mice were injected with 200 μg of CRP (n=8, early CRP treatment) or saline (n=12). Saline-treated mice with 4+ proteinuria were injected with 200 pg of CRP (n=6, late CRP treatment) at 13 weeks. A. Survival of mice is shown. Mice that exhibited 4+ proteinuria and weight loss of >20% were killed for humanitarian reasons. Median survival times were: saline, 18.5 weeks; early CRP treatment, 23 weeks and late CRP treatment 29 weeks (both p<0.05 vs. saline). B & C. Proteinuria was measured weekly using Chemstrips (scale: 0=none, 1+=trace, 2+=30 mg/dl, 3+=100 mg/dl, 4+=>500 mg/dl) B. Onset of severe proteinuria (>3+) in early CRP treatment vs. saline treatment C. Weekly proteinuria scores. Mean scores t SEM are shown. D. BUN was measured monthly using Azostix with a range from 0 to >80 mg/di. Mean scores±SEM are shown.

FIG. 3 shows that CRP delays the development of anti-dsDNA antibodies in MRLI11pr mice. A & B. Mice were treated with CRP or saline at 6 weeks. Results for 14 weeks using serum diluted 114,000. Mean absorbance values for individual mice±SEM. A. ELISA of IgG antidsDNA. B. ELISA of IgM anti-dsDNA. C. ELISA of IgG anti-dsDNA for mice shown in FIG. 1. Mean absorbance values for serum diluted 11400 t SEM. **, p<0.01 compared to saline. D. Farr assay of week 13 samples from C. Results are expressed as IU/ml.

FIG. 5 shows that early and late CRP treatment reduces glomerular and tubular lesions in MRT, IIpr mice. A. and B. Glomerular pathology is shown for 15 and 17 week old mice treated with saline or with CRP at 6 weeks (early CRP) or 15 weeks [late CRP). There were 7 mice in each group. One mouse that failed to respond to treatment was excluded from the early CRP group at 17 weeks. Glomerular changes were scored on a 4 point scale based on the number of glomeruli involved and the severity of the lesions (1, <10%, minimal; 2, 1025%, mild; 3, 50%, moderate; 4, >50%, marked). The average glomerular lesion scores are the combined individual scores. C. Tubular and interstitial renal pathology scores for the same mice, also scored on a 4 point scale by the extent of involvement and severity of the lesions. D. Perivascular renal lesion scores for the same mice, also scored on a 4 point scale by the extent of involvement and severity of the lesions. In all panels significant differences between either CRP treatment group and the saline group are indicated by *, p<0.05; **, p<0.01.

FIG. 8A shows that CRP and SAP increase pharocytosies of apoptotic cells in vitro. Normal and UV-treated apoptotic Jurkat T cells were labeled with calcein, opsonized with CRP or SAP and incubated with mouse macrophases (J774 cells). Phagocytosis was determined by fluorescent microscopy and expressed as the phagocytic index (Jurkat cells ingested by 100 macrophases). CRP and SAP increased the ingestion of apoptotic cells. (n==6)** p<0.01; * p<0.05 (compared to buffer). FIG. 8B shows that CRP increases phagocytosis of apoptotic cells in vivo. Dexcamethasone-treated mouse thymocytes were treated with CRP and injected i.p. into thioglycollate-treated mice. After 30 min., peritoneal cells were fixed on slides and stained with DiffQuik. Phagocytosis was determined by microscopy and expressed as the phagocytic index (thymocytes ingested by 100 macrophases). CRP increased the phagocytic index in normal, FcγRI (CD64) and C3 mice. (n=3)** p<0.01; * p<0.05 (compared to buffer).

FIG. 9 shows that CRP stimulates IL-10 rather than IFN-a production by PBMC in response to snRNPs. Human PBMCs were incubated with 20 μg/ml snRNP in the presence of 2% anti-RNP and/or 100 μg/ml CRP for 24 h. Supernatants were tested by ELISA for A. IFN-a (n=3; **p<0.01 compared to snRNP, anti-RNP) or B. IL-10. n=3; * p<0.05, ** p<0.01 compared to control).

FIG. 16 shows the effect of Effect of early CRP treatment on MIP-1a, MCP-1 and IFN-g expression in renal tissue. RNA was extracted from kidneys of 17 week old MRL/lpr mice treated with saline or CRP at 6 weeks of age. mRNA expression was quantitated by qRT-PCR relative to 6 week old, pre-diseased mice and correlated with GLS from FIG. 4. Glomerular score is directly correlated with MIP-1a, MCP-1 and IFN-g mRNA in kidneys of saline-treated mice but not in CRP-treated mice.

BRIEF DESCRIPTION OF THE INVENTION

Figure 4:
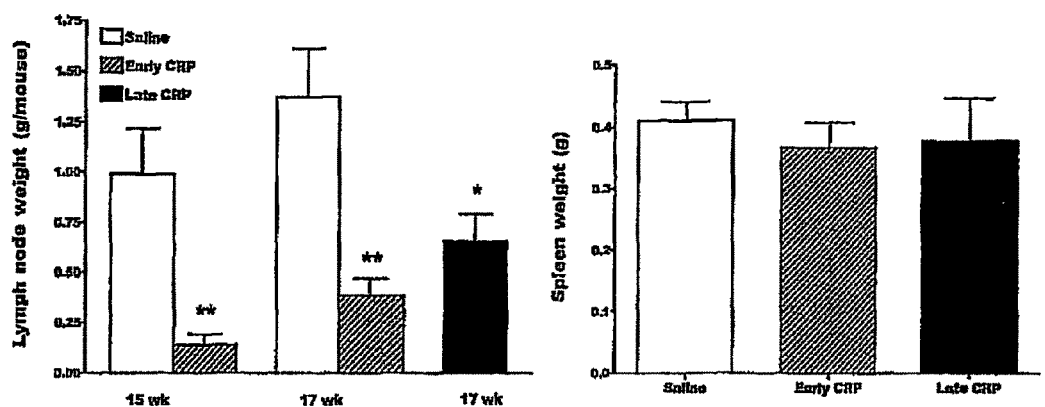
FIG. 4 shows that early or late CRP treatment decreases lymphadenopathy but not splenomegaly in MRL11pr mice. A. Lymph node weights of MRL11pr mice treated with CRP at 6 weeks or at 15 weeks and killed at 15 or 17 weeks. Mean weights±SEM are shown (n=7 per group). B. Spleen weights of mice killed at 17 weeks. Significant differences between either CRP treatment group and the saline group are indicated by *, p<0.05; **, p<0.01.

The present invention relates to the use of C-reactive protein (CRP) and derivatives thereof in the treatment of a number of disease states or conditions that occur secondary to systemic lupus erythematosus (SLE). The present invention relates to the use of CRP, a mutant polypeptide thereof; a metabolite thereof, or a 6-20 unit amino acid polypeptide or multimer thereof alone, or in combination with a natural or synthetic carrier, such as human serum albumin or a dendrimer, in the treatment of SLE. In particular aspects of the invention, any one or more of secondary conditions, disease states or manifestations of SLE including serositis, malar rash (rash over the cheeks and bridge of the nose), discoid rash (scaly, disk-shaped sores on the face, neck and chest), sores or ulcers (on the tongue, in the mouth or nose), arthritis, hemolytic anemia, lymphadenopathy, low lymphocytic count, low platelet count, the presence of antinuclear antibodies in the blood, skin lesions, CNS effects (including loss of memory, seizures, strokes and psychosis), lung symptoms/effects including inflammation (pleuritis), chronic pneumonitis, chronic diffuse interstitial lung disease and scarring of the lungs, hair loss, Raynaud's syndrome, lupus nephritis and sensitivity to light, fatigue, fever, nausea, vomiting, diarrhea, swollen glands, lack of appetite, sensitivity to cold (Raynaud's phenomenon) and weight loss is treated using compounds and pharmaceutical compositions according to the present invention.

The method of the present invention comprises administering to a patient suffering from SLE an effective amount of CRP, a mutant thereof, a metabolite of CRP or a reactive amino acid polypeptide unit or multimer thereof, alone or in combination with a natural or synthetic carrier such as human serum albumin or a dendrimer as otherwise described herein, optionally in the presence of a pharmaceutically acceptable additive, carrier or excipient in an amount effective to treat SLE, and in particular, any one or more of its secondary disease states, conditions or symptoms of said patient. In optional embodiments of the present invention, CRP, or one of the other compounds disclosed herein, is administered to patients suffering from systemic lupus erythematosus (SLE) wherein the SLE does not produce or express itself in a kidney associated disease or condition, including lupus nephritis. Pharmaceutical compositions comprising an effective amount of a C-reactive protein mutant polypeptide, a reactive amino acid polypeptide of CRP as otherwise disclosed herein or a multimer thereof, alone or in combination with a natural or synthetic carrier and optionally, a pharmaceutically acceptable additive, carrier or excipient are additional aspects of the present invention.

In alternative embodiments of the invention, a compound according to the present invention (CRP, metabolite or mutant thereof, polypeptide or multimer derived therefrom alone or in combination with an active carrier may be coadministered with an effective amount of at least one additional agent which is traditionally used in the treatment of system lupus erythematosus. These agents include, for example, non-steroidal anti-inflammatory drugs (NSAIDs) including traditional NSAIDs, COX-2 inhibitors and salicylates (such as aspirin), anti-malarials such as hydroxychloraquine, quinacrine, corticosteroids such as prenisone (Deltasone), betamethasone (Celestone), methylprednisolone acetate (Medrol, Depo-Medrol), hydrocortisone Cortef, Hydrocortone) and dexamethasone (Decadron, Hexadrol), among others and immunosuppressants such as methotrexate (Rhematrex), cyclophosphamide (cytoxan), Azathioprine (Imuran) and mycophenolate mofetil (MMF, also Cellsept),

DETAILED DESCRIPTION OF THE INVENTION

The following terms shall be used to describe the present invention.

The term "patient" refers to an animal, preferably a mammal, even more preferably a human, in need of treatment or therapy to which compounds according to the present invention are administered in order to treat a condition or disease state associated with systemic lupus erythematosus treatable using compounds according to the present invention.

The term "compound" is used herein to refer to any specific chemical compound disclosed herein. Within its use in context, the term generally refers to a single compound, generally a polypeptide of varying length.

The term "systemic lupus erythematosus", "SLE" or "lupus" is used to describe a chronic potentially debilitating or fatal autoimmune disease in which the immune system attacks the body's cells and tissue, resulting in inflammation and tissue damage. LSE refers to several forms of an immunologic disease that affects the joints, skin, muscles, face and mouth, kidneys, central nervous system and other parts of the body. SLE is a chronic and inflammatory disease that can potentially be fatal. SLE can either be classified as an autoimmune or a rheumatic disease. Changes in symptoms are called flares and remissions. Flares are periods when SLE becomes more active with increased symptoms, and remissions are periods when few or no symptoms of lupus are present. In the United States alone, an estimated 270,000 to 1.5 million or more people have SLE, with an estimated 5 million worldwide, having the disease. It is more common than cystic fibrosis or cerebral palsy.

The specific cause of SLE is unknown. It is considered to be a multifactoral condition with both genetic and environmental factors involved. In a multifactoral condition, a combination of genes from both parents, in addition to unknown environmental factors, produce the trait, condition, or disease. It is known that a group of genes on chromosome 6 that code for the human leukocyte antigens play a major role in a person's susceptibility or resistance to the disease. The specific HLA antigens associated with SLE are DR2 and DR3. When the immune system does not function properly, it loses its ability to distinguish between its own body cells and foreign cells. Antinuclear antibodies are autoantibodies (antibodies that fight the body's own cells) that are produced in people with SLE. They often appear in the blood of a patient with SLE.

Studies suggest that some people may inherit the tendency to get SLE, and new research suggests that new cases of SLE appear to be more common in families in which one member already has the disease. However, there is no evidence that supports that SLE is directly passed from parent to child. Females in their childbearing years (18-45) are eight to ten times more likely to acquire SLE than men, and children and the elderly can also acquire the disease.

SLE is unpredictable, and no two people have exactly the same manifestations of the disease. There are 11 criteria that help doctors tell the difference between people who have SLE and people who have other connective tissue diseases. If a person displays 4 or more of the following 11 criteria, the person fulfills the requirement for the diagnosis of SLE.

1. Malar rash—a butterfly shaped rash over the cheeks and across the bridge of the nose;
2. Discoid rash—scaly, disk-shaped sores on the face, neck, and chest;
3. Serositis—inflammation of the lining around the heart, lungs, abdomen, causing pain and shortness of breath;
4. Photosensitivity—skin rash as an unusual reaction to sunlight;
5. Sores or ulcers on the tongue, mouth, or in the nose;
6. Arthritis;
7. Kidney disorder—persistent protein or cellular casts in the urine;
8. Central nervous system problems including seizures and psychosis;
9. Blood problems such as low white blood cell count, low lymphocyte count, low platelet count, or hemolytic anemia;
10. Immune system problems (immune dysfunction/dysregulation)—presence of abnormal autoantibodies to double stranded DNA, Sm antigen or phospholipid in the blood; and
11. Presence of abnormal antinuclear antibodies in the blood.

Other symptoms/manifestations of SLE include inflammatory lung problems lymphadenopathy, fever, nausea, vomiting, diarrhea, swollen glands, lack of appetite, sensitivity to cold (Raynaud's phenomenon), weight loss, and hair loss.

Notwithstanding the numerous disease states, conditions and/or manifestations associated with SLE, it is difficult to diagnose because there is no single set of signs and symptoms to determine if a person has the disease. There is no single test that can diagnose SLE. Some tests used to diagnose SLE include urinalysis to detect kidney problems, tests to measure the amount of complement proteins in the blood, complete blood cell counts to detect hematological disorders, and an ANA test to detect antinuclear antibodies in the blood. Additionally, X-rays may be ordered to check for lung and heart problems.

The term "effective" shall mean, within context, an amount of a compound, composition or component and for a duration of time (which may vary greatly depending upon the disease state, condition or manifestation to be treated or to have a reduced likelihood of occurring) which produces an intended effect. In instances where more than one compound is administered (coadministration) or a component is used, that compound or component is used in an effective amount to produce a desired or intended effect, very often, a favorable therapeutic outcome.

The term "treatment" or "treating" is used to describe an approach for obtaining beneficial or desired results including and preferably clinical results. For purposes of this invention, beneficial or desired clinical results include, but are not limited to, one or more of the following: alleviation of one or more symptoms, diminishment of extent of disease, stabilized (i.e., not worsening) state of disease, preventing or reducing the likelihood of the spread of disease, reducing the likelihood of occurrence or recurrence of disease, decreasing, delaying or reducing the likelihood of the occurrence of "flares," amelioration of the disease state, remission (whether partial or total), reduction of incidence of disease and/or symptoms, stabilizing (i.e., not worsening) of immune or renal function or improvement of immune or renal function. "Flares" refer to an increase in activity, generally inflammatory activity in a particular tissue. The "treatment" of SLE may be administered when no symptoms of SLE are present, and such treatment (as the definition of "treatment" indicates) reduces the incidence or likelihood of flares. Also encompassed by "treatment" is a reduction of pathological consequences of any aspect of SLE or any associated disease states or conditions, including skin rashes (malar and discoid), arthritis, serositis (inflammation of the lining around the heart, lungs, abdomen), sores (mouth, nose and tongue), immune dysfunction/dysregulation, central nervous system problems (including psychosis, seizures and strokes), blood problems (including low white blood cell count, low platelet count, or anemia), the presence of antinuclear antibodies in the blood and kidney disease/dysfunction (especially SLE-related nephritis).

"SLE flares" are used herein to refer to flares (i.e. acute clinical events) which occur in patients with SLE. The SLE flares may be in various major organs, including but not limited to, kidney, brain, lung, heart, liver, connective tissues and skin. Flares can include activity in all tissues that may be affected by SLE. Remission is a term used to refer to periods of little or no lupus symptoms.

"Reducing incidence" of renal flares in an individual with SLE means any of reducing severity (which can include reducing need for and/or amount of (e.g., exposure to) other drugs generally used for this conditions, including, for example, high dose corticosteroid and/or cyclophosphamide), duration, and/or frequency (including, for example, delaying or increasing time to renal flare as compared to not receiving treatment) of renal flare(s) in an individual. As is understood by those skilled in the art, individuals may vary in terms of their response to treatment, and, as such, for example, a "method of reducing incidence of renal flares in an individual" reflects administering the conjugate(s) described herein based on a reasonable expectation that such administration may likely cause such a reduction in incidence in that particular individual.

The term "C-reactive protein" or "CRP" is used herein to describe a 206 amino acid protein, which is a member of the class of acute phase reactants as its levels rise dramatically during inflammatory processes occurring in the body. It is thought to assist in removal of damaged cells and affect the humoral response to disease. It is also believed to play an important role in innate immunity, as an early defense system against infections. CRP is used mainly as a marker of inflammation. CRP is the prototypic acute phase reactant in humans and is a component of the innate immune system. CRP binds to nuclear antigens that are the target of the autoantibodies of patients with SLE as well as to damaged membranes and microbial antigens. CRP activates the classical complement pathway and interacts with phagocytic cells through FcγR CRP is protective against various inflammatory states including endotoxin shock and inflammatory alveolitis. CRP protection against endotoxin shock requires FcγR and is associated with FcγR-dependent induction of interleukin-10 (IL-10) synthesis by macrophages.

CRP is an acute phase serum protein that provides innate immune recognition, opsonization, and regulation of autoimmunity and inflammation. CRP may bind several autoantigens in SLE, for example SmD1 and 70K proteins of Sm and RNP, histones, and chromatin. CRP may activate complement and may bind to Fc RI and Fc RII in man and mouse. CRP is a natural product found in the serum of people, and it is believed to be nontoxic.

CRP has 206 amino acid units. The entire sequence of C-reactive protein appears in FIG. 1 (SEQ ID NO:1). The polypeptide sequence of CRP also has the following Accession numbers: BC125135, NM_000567, BC070257, BC020766, M11880, M11725, X56214 and X56692, all of which sequences are incorporated by reference herein. SEQ ID NO:1 is also represented as follows:

(SEQ ID No: 1)
MEKLLCFLVLTSLSHAFGQTDMSRKAFVFPKESDTSYVSLKAPLTKPLKA

FTVCLHFYTELSSTRGYSIFSYATKRQDNEILIFWSKDIGYSFTVGGSEI

LFEVPEVTVAPVHICTSWESASGIVEFWVDGKPRVRKSLKKGYTVGAEAS

IILGQEQDSFGGNFEGSQSLVGDIGNVNMWDFVLSPDEINTIYLGGPFSP

NVLNWRALKYEVQGEVFTKPQLWP

In one aspect of the invention, C-reactive protein is prepared as a dosage formulation for delivery to a human patient and administered in order to treat systemic lupus erythematosus (SLE) or any one or more of the secondary disease states, conditions or symptoms which occur in a patient with SLE.

Human CRP may be purified from human pleural effusion fluid. T. W. Du Clos, "C-reactive protein reacts with the U1 small nuclear ribonucleoprotein," *J. Immunol.* 143:2553-2559 (1989). For example, human pleural fluids may be obtained from discarded drains of patients undergoing surgery. The fluids may be clarified by high speed centrifugation. The CRP may be partially purified by affinity chromatography and then may be further purified by gel filtration chromatography. The CRP may then be further purified by affinity chromatography on PC-Sepharose. For final purification, the protein may be purified by mono Q based FPLC. A major band should be seen at about 25 kDa on SDS-PAGE. The final preparation may then be filter-sterilized and an endotoxin contamination may be measured by a limulus-based assay from Cambrex (East Rutherford, N.J.). Endotoxin may be removed using Acticlean Etox (Sterogene Bioseparations Inc., Carlsbad, Calif.) to reduce preparations to less than 0.3 ng of endotoxin/mg of protein.

Alternatively, CRP may be produced as a recombinant protein following general procedures well known in the art. U.S. Pat. No. 5,702,921 to Tanaka describes the production of human C-reactive protein using *Escherichia coli* vectors described therein. Recombinant CRP may also be produced using a baculovirus expression system as described in Marnell et al. *Protein Expression and Purification* 6:439, 1995.

Other polypeptides useful in the present invention may be readily synthesized using well-known genetic engineering techniques or polypeptide synthetic methods, especially for the polypeptides, multimers based upon same or compounds comprising a polypeptide that is complexed to a carrier for therapeutic delivery. Polypeptides according to the present invention may be useful as therapies for SLE and in particular, one or more of the disease states, conditions or symptoms associated with SLE, as standards or as research tools for assisting in further research to determine the structure of optimal polypeptides useful in treating SLE, or to provide three dimensional structural features for developing small molecule mimetics and agents useful in treating SLE or any one or more of the disease states, conditions or symptoms associated with SLE.

The term "mutant", "C-reactive protein mutant" or "CRP mutant" is used to describe a mutant C-reactive protein according to the present invention where the naturally occurring sequence of CRP (SEQ ID No: 1) has been altered at one or more amino acids in the naturally occurring sequence. Mutants for use in the present invention have altered amino acids (non-naturally occurring amino acids) at amino acid residue 112 of the naturally occurring (wild-type) C-reactive protein (Asn, Gln, Arg, Ala, Leu, Ile or Val for the naturally occurring asp), at amino acid residue 38 (Arg, Asn or Gln for naturally occurring his), at amino acid residue 169 (Ala, Leu, Ile or Val for the naturally occurring Asp), at amino acid 175 (Ala, Leu, Ile or Val for the naturally occurring Tyr), at amino acid 176 (Gln, Asn, Arg, Ala, Ile or Val for the naturally occurring Leu) and in a double mutant at amino acids 66 and 81, at amino acid residue 66 (Ala, Leu, Ile or Val for the naturally occurring Phe at 66) and at amino acid residue 81 (Ala, Leu, Ile or Val for the naturally occurring Glu at 81. Preferred mutant polypeptides for use in the present invention include D112N (Asn substituted for Asp at amino acid 112), D112A (Ala substituted for Asp at amino acid 112), H38R (Arg substituted for His at amino acid 38), D169A (Ala substituted for Asp at amino acid 169), Y175L (Leu substituted for Tyr at amino acid 175), L1760 (Gln substituted for Leu at amino acid residue 176) and the double mutant F66A/E81A (Ala substituted for Phe at amino acid residue 66 and Ala substituted for Glu at amino acid residue 81). The amino acid sequences of the naturally occurring C-reactive protein (SEQ ID. No:1), and mutants D112N (SEQ ID No:2), D112A (SEQ ID No: 3), H38R (SEQ ID No:4), D169A (SEQ ID No:5), Y175L (SEQ ID No:6), L1760 (SEQ ID No:7) and the double mutant F66A/E881A (SEQ ID No:8) are presented in attached FIG. 1.

The term "carrier" or "active carrier" shall be used in context to describe a complex molecule, including a polymer which can be used in combination with a C-reactive protein polypeptide, smaller chain polypeptides such as the 6-15 amino acid polypeptides of C-reactive protein as otherwise disclosed here) or multimers according to the present. A carrier may be an oligomeric polypeptide, such as oligo- or polylysine, oligo- or polyarginine, or a mixture thereof (generally from about 5-1000 mer or greater, but also ranging from about 10 to about 100 mer), polyglutamic acid, polyaspartic acid, polyhistidine, polyasparagine, polyglutamine, etc. or a dendrimer as otherwise disclosed in US patent publication 2003/0232968 to Chun Li, et al. Additional dendrimers are available from Sigma-Aldrich, USA or Dendritic Nano Technologies, Inc., Mount Please, Mich., USA. Dendrimers may include PAMAM dendrimers, phosphorous dendrimers, polypropyleneimine dendrimers, lysine dendrimers, among numerous others. Also called a cascade molecule, a dendrimer is a polymer that has many branches that move out from a core, generally a carbon core. Many of these dendrimers are available commercially from Sigma-Aldrich or from Dendritic Nano Technologies.

Other ways of attaching the protein or polypeptide include modification of a particle surface by adsorption or covalent attachment of suitable linking group(s) to which the protein may be subsequently attached. Examples of additional carriers include polyethylene glycol (with an average molecular weight ranging from about 100 to about 2000), polyethylene glycol co-polypropylene glycol copolymer (random or block copolymers) of similar molecular weight as the polyethylene glycol, albumin (preferably human serum albumin for human therapies), collagen (preferably human recombinant collagen), gelatin, dextran (including cyclodextrin), alginate, polylactide/glycolide, polyhydroxy-butyrate, polyvinyl alcohol, polyanhydride microspheres and liposomes, among others. One of ordinary skill will readily recognize how to complex or attach the present therapeutic polypeptides to carriers using techniques and methodologies which are well known in the art.

The term "short-chain polypeptide" refers to a polypeptide having a length of at least 6 amino acid units, preferably at least about 10 amino acid units that are useful in the present invention.

Two short-chain polypeptides are preferred for use in the present invention. Other short-chain polypeptides are also useful in the present invention. Their sequences are:

Ile Tyr Leu Gly Gly Pro Phe Ser Pro Asn Val Leu (IYLGGPFSPNVL) (SEQ ID No: 9) Corresponding to amino acid units 174-185 of CRP;

Leu Ser Pro Asp Glu Ile Asn Thr Ile Tyr Leu Gly Gly Pro Phe (LSPDEINTIYLGGPF) (SEQ ID No:10) Corresponding to amino acid units 166-180 of CRP;

Leu Ser Pro Asp Glu Ile Asn Thr Ile Tyr Leu Gly Gly Pro Phe Ser Pro Asn Val Leu (LSPDEINTIYLGGPFSPNVL) (SEQ ID NO:11) Corresponding to amino acid units 166-185 of CRP;

At least 10 to 19 (10, 11, 12, 13, 14, 15, 16, 17, 18 or 19) contiguous amino acids of the polypeptide sequence of SEQ D No. 11);

Lys Pro Gln Leu Trp Pro (KPQLWP) (Seq. ID. No: 12) Corresponding to amino acid units 201-206 of CRP.

The polypeptides of the present invention may be administered directly as a pharmaceutical composition when combined with a pharmaceutically acceptable additive, carrier or excipient or alternatively, may be used in combination with a carrier (adsorbed or covalently bound to the carrier as otherwise described herein) or to form multimers comprising the polypeptides.

The term "multimer" is used to describe peptide compounds according to the present invention which are used as multiples of the individual polypeptide units found in the simplest peptide compounds according to the present invention (which range from 6 amino acid units to 20 amino acid units or more). For example, a dimer may be a multiple of a 6 amino acid unit polypeptide (i.e., 12 amino acid units), a multiple of a 10 amino acid unit polypeptide (i.e., 20 amino acid units), an 11 amino acid unit polypeptide (i.e., 22 amino acid units), etc., whereas a trimer is a peptide of a triple multiple of a basic polypeptide. Thus, the term multimer refers to a polypeptide that is incorporated in a molecule in repeating units or chains. Multimers include dimers, trimers, tetramers, pentamers, hexamers, heptamers, octamers, etc. up to as many as 50 or 100 repeat units or more. Preferably, a multimer contains between 2 and 6 repeat units (dimers, trimers, tetramers, pentamers and hexamers).

The individual units of multimers according to the present invention may be linked in a variety of ways including the use of disulfide bonds between cystinyl residues at the amino or carboxyl end of the polypeptide unit, or alternatively, through peptide bonds (amide linkages) or other chemical linkers at the amino or carboxy terminus of the individual polypeptide units. Multimers according to the present invention are usually no more than dodecamers (12 individual polypeptide units), and are more preferably dimers, trimers or tetramers, even more preferably dimers.

The term "coadministration" or "combination therapy" is used to describe a therapy in which at least two active compounds in effective amounts are used to treat systemic lupus erythematosus a related disease state, condition or symptom at the same time. Although the term coadministration preferably includes the administration of two active compounds to the patient at the same time, it is not necessary that the compounds be administered to the patient at the same time, although effective amounts of the individual compounds will be present in the patient at the same time.

"Naturally occurring" refers to an endogenous chemical moiety, such as a polypeptide or polynucleotide sequence or a carbohydrate, i.e., one found in nature. Processing of naturally occurring moieties can occur in one or more steps, and these terms encompass all stages of processing. Conversely, a "non-naturally occurring" moiety refers to all other moieties, i.e., ones which do not occur in nature, such as recombinant polynucleotide sequences and non-naturally occurring carbohydrates.

According to various embodiments, the compounds according to the present invention may be used for treatment or prevention purposes in the form of a pharmaceutical composition. This pharmaceutical composition may comprise one or more of CRP (preferably pure or recombinant CRP), a mutant polypeptide thereof, an active polypeptide fraction of CRP, a multimer thereof or a polypeptide which is combined with a polypeptide carrier as otherwise described herein. Active metabolites of CRP may also be used. For example, the pharmaceutical composition may comprise a mixture of CRP and a metabolite of CRP. The oral dosage form may be in a form chosen from a solid, semi-solid, and liquid.

The pharmaceutical composition may also comprise a pharmaceutically acceptable excipient, additive or inert carrier (distinguishable from carriers which are complexed with an active polypeptide herein). The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrrolidone, polyvinylpolypyrrolidone, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive. If a polypeptide carrier is used, it is preferred to combine the polypeptide with the polypeptide carrier before combining with other components in preparing a pharmaceutical dosage form.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, pulmonary (especially for treatment of lung conditions), buccal, nasal, intramuscular, transcutaneous, transdermal, intranasal, intraperitoneal, and topical (especially for certain skin rashes and skin conditions).

The subject or patient may be chosen from, for example, a human, a mammal such as domesticated animal, or other animal. The subject may have one or more of the disease states, conditions or symptoms associated with SLE.

The compounds according to the present invention may be administered in an effective amount to treat or reduce the likelihood of SLE, any one or more of the disease states conditions or conditions associated with SLE including, for example serositis, malar rash (rash over the cheeks and bridge of the nose), discoid rash (scaly, disk-shaped sores on the face, neck and chest), sores or ulcers (on the tongue, in the mouth or nose), arthritis, hemolytic anemia, low lymphocytic count, low platelet count, the presence of antinuclear bodies in the blood, skin lesions, CNS effects (including loss of memory, seizures, strokes and psychosis), lung symptoms/effects including inflammation (pleuritis), chronic pneumonitis, chronic diffuse interstitial lung disease and scarring of the lungs, hair loss, Raynaud's syndrome, lupus nephritis and sensitivity to light, fatigue, fever, nausea, vomiting, diarrhea, swollen glands, lack of appetite, sensitivity to cold (Raynaud's phenomenon) and weight loss. One of ordinary skill in the art would be readily able to determine this amount by taking into consideration several variables including, but not limited to, the animal subject, age, sex, weight, site of the disease state or condition in the patient, previous medical history, other medications, etc.

For example, the dose of a compound for a human patient is that which is an effective amount and may range from as little as 100 µg to at least about 500 mg or more, which may be administered in a manner consistent with the delivery of the drug and the disease state or condition to be treated. In the case of oral administration, active is generally administered from one to four times or more daily. Transdermal patches or other topical administration my administer drugs continuously, one or more times a day or less frequently than daily, depending upon the absorptivity of the active and delivery to the patient's skin Of course, in certain instances where parenteral administration represents a favorable treatment option, intramuscular administration or slow IV drip may be used to administer active. The amount of CRP which is administered to a human patient preferably ranges from about 0.05 mg/kg to about 10 mg/kg, about 0.1 mg/kg to about 7.5 mg/kg, about 0.25 mg/kg to about 6 mg/kg., about 1.25 to about 5.7 mg/kg.

The dose of a compound according to the present invention may be administered prior to the onset of SLE, during SLE flares or during remission prior to an expected flare. For example, the dose may be administered for the purpose of treating and/or reducing the likelihood of any one or more of these disease states or conditions occurs or manifests, including serositis, malar rash (rash over the cheeks and bridge of the nose), discoid rash (scaly, disk-shaped sores on the face, neck and chest), sores or ulcers (on the tongue, in the mouth or nose), arthritis, hemolytic anemia, low lymphocytic count, low platelet count, the presence of antinuclear bodies in the blood, skin lesions, CNS effects (including loss of memory, seizures, strokes and psychosis), lung effects including chronic pneumonitis and scarring of the lung, hair loss, Raynaud's syndrome, lupus nephritis, sensitivity to light, fatigue, fever, nausea, vomiting, diarrhea, swollen glands, lack of appetite, sensitivity to cold (Raynaud's phenomenon), weight loss, and hair loss. The dose may be administered prior to diagnosis, but in anticipation of SLE or anticipation of flares. The dose also is preferably administered during flares to reduce the severity of same.

To determine whether CRP and its derivatives could induce suppression of disease in autoimmune mice with more severe nephritis and to determine its effects on other disease manifestations, we tested the effect of CRP on the MRL/lpr model of SLE. The MRL/lpr mouse is characterized by a more rapid and aggressive onset of lupus nephritis than the NZB/W mouse (16). MRL/lpr mice develop high levels of autoantibodies to DNA and hypergammaglobulinemia. In addition, these mice develop vasculitis, arthritis, splenomegaly and massive lymphadenopathy. The disease is dependent on the unrestricted proliferation of T cells due to a defect in the Fas gene, which is required for apoptosis of effete T cells.

In this work, we examined the effect of CRP in the MRL/lpr model of human SLE. Mice were treated with CRP either just before the onset of proteinuria or during the active phase of disease, and followed for clinical and laboratory parameters of disease. The data indicate that CRP suppresses renal disease, lymphadenopathy and autoantibody production in the MRL/lpr mouse. Depletion experiments indicate that suppression of disease appears to be maintained by an active process involving CD25-bearing T cells.

EXAMPLES

Materials And Methods

Animals. MRL/lpr female mice were obtained from Jackson Laboratories (Bar Harbor, Me.) and maintained at the Albuquerque Va. Animal Facility. All procedures involving animals were approved by the Institutional Review Board of the VA Medical Center.

Reagents. Human CRP was purified from pleural fluid as described (17). Preparations were examined on overloaded SDS-PAGE gels to ensure that no contaminating protein bands were seen. In addition, preparations were examined for endotoxin by a quantitative chromogenic LAL assay (Cambrex, Waldersville, Md.). If needed, endotoxin was removed on an Etox Acticlean column (Sterogene, Carlsbad, Calif.). All preparations contained less than 0.3 ng of endotoxin/mg of protein. Anti-CD25 mAb PC61 was purified from hybridoma supernatants of the cell line (American Type Culture Collection, Rockville, Md.), using a HiTrap protein G affinity column (Amersham Biosciences, Piscataway N.J.).

Figure 6:
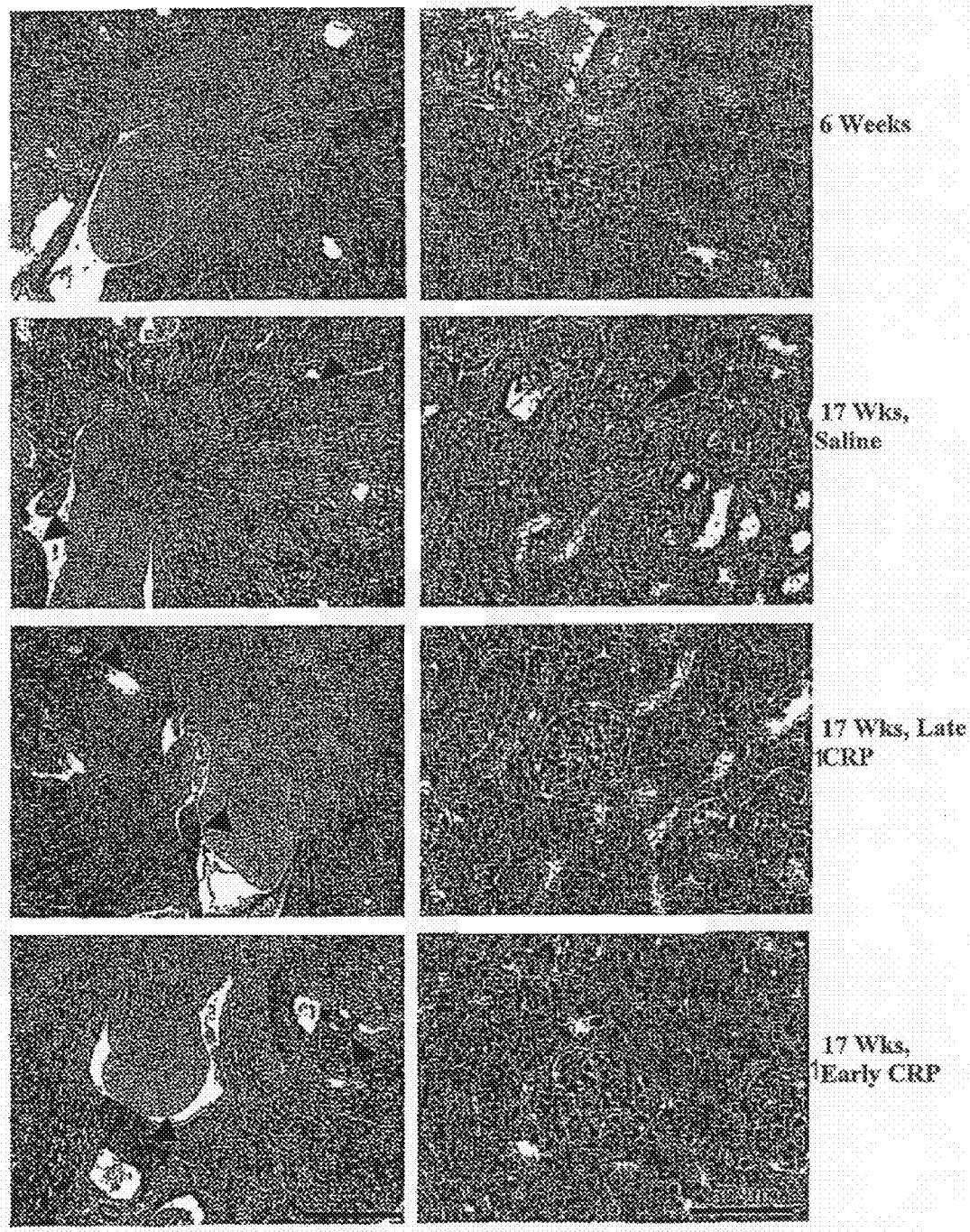
FIG. 6 shows that Early and late CRP treatment reduces glomerular and tubular lesions and interstitial inflammation in MRL11pr mice. A) and B) 6 week old mice, prior to the onset of renal disease; C) and D) 17 week old mice treated with saline; E) and F) 17 week old mice treated with CRP after the onset of proteinuria (at 15 weeks); G) and H) 17 week old mice treated with CRP at 6 weeks. Arrowheads denote perivascular lymphocytic, histiocytic and plasmacytic infiltrates which were similar in occurrence in all mice at 17 weeks. The large arrow in D indicates a severely affected glomerulus, typical of those observed in the saline-treated control mice, characterized by increased glomerular cellularity with hypertrophy of glomeruli, periglomerular and intraglomerular mononuclear cell infiltrates, and crescent formation. The small arrow in D indicates a tubule containing protein rich fluid. The left panels (C, E and G) with arrowheads indicate perivascular infiltrates, which were not affected by CRP treatment.

CRP treatment of MRL/lpr mice. Six week old MRL/lpr mice were given a single s.c. injection of saline or 200 μg of CRP (early CRP treatment). Urinary protein levels were measured weekly either using Chemstrips (Roche, Nutley, N.J.) (FIGS. 1-2) or Albustix (Bayer) (FIG. 6). Proteinuria is expressed as 0 (none); 1+, (trace); 2+, (30 mg/dl); 3+(100 mg/dl); 4+, (300 mg/dl); 5+, (>2000 mg/dl) for Chemstrips. Proteinuria is expressed as 0 (none), 1+, (trace); 2+, (30 mg/dl); 3+, (100 mg/dl); or 4+, (500 or more mg/dl) for Albustix. Serum was collected monthly to measure autoantibody levels. When the saline-treated MRL/lpr mice had developed significant proteinuria (13-15 weeks), mice from this group with 4+ proteinuria were injected s.c. with 200 μg CRP (late CRP treatment). Proteinuria was followed daily for one week and then weekly for the remaining course of the disease. Mice were euthanized for humanitarian reasons if they developed 4+ proteinuria accompanied by weight loss of greater than 20%. Euthanized mice are included as deaths in the survival curves. Blood urea nitrogen (BUN) was measured in whole blood using Azostix (Bayer).

Depletion studies. Liposomes containing dichloromethylene bisphosphonate (Clodronate) were prepared exactly as described (18). Phosphatidylcholine and cholesterol were purchased from Sigma (St, Louis, Mo.). Mice were injected with 0.2 ml of Clodronate liposomes i.v. We previously documented this treatment to deplete >99% of Kupffer cells and >95% of splenic macrophages (19). Control liposomes were prepared with PBS in place of Clodronate.

Mice were given a single i.p. injection of 1 mg of the purified rat anti-mouse CD25 mAb, PC61. This protocol depletes CD4+CD25+ cells from peripheral blood, lymph nodes and spleens of normal mice for at least 15 days (20). PC61 treatment of MRL/lpr mice reduced the number of CD25 bright, CD4+ cells in the blood from 7.4±1.1% in control mice to 2.6±0.5% in the anti-CD25-treated mice (p<0.02) 4 days after treatment.

ELISA for anti-double-stranded DNA (anti dsDNA). IgG anti-dsDNA antibodies were measured as described (21) using serum diluted 1:400 or 1:4,000. Autoantibodies to dsDNA were also determined using the Farr Assay (Diagnostic Products, Los Angeles, Calif.), according to the manufacturer's instructions, except that the mouse sera were diluted 1:5. Lymphadenopathy and splenomegaly. Lymph nodes of mice treated with CRP at 6 weeks and followed for survival were palpated weekly and scored for the development of lymphadenopathy on a 3 point scale as described (22). Spleens and axillary and inguinal lymph nodes were removed from mice killed at 15 and 17 weeks following early CRP treatment at 6 weeks or late CRP treatment at 15 weeks and wet weights determined.

Histopathological studies. Groups of 7 mice were killed at 15 and 17 weeks following early CRP treatment at 6 weeks or late CRP treatment at 15 weeks. Kidneys were perfused with PBS prior to collection for histopathology. Tissues were fixed for 2 h in Bouin's solution and then transferred to 70% ethanol. Tissues were processed, embedded in paraffin, sectioned at 2 microns and stained with hematoxylin and eosin (H & E).

The sections were examined and scored by a veterinary pathologist in a blinded manner. Glomerular lesion scores were assigned on a 4-point scale based on the number of glomeruli involved and the severity of the lesions (1, <10%, minimal; 2, 10-25%, mild; 3, 50%, moderate; 4, >50%, marked). Scores for non-glomerular lesions (proteinuria, tubular degeneration, interstitial inflammation, and perivascular inflammation), were also assigned on a 4 point scale. Fifty glomeruli from one kidney of each mouse were examined.

Immunofluorescent staining of Kidney sections. Sections of kidneys were embedded in OCT (Sakura, Torrence Calif.) and stored at −70° C., until they were processed for fluorescence microscopy. Serial 4 μm sections were cut on a cryostat microtome, mounted on glass slides, air-dried, acetone-fixed, and stained for mouse immunoglobulins and C3. Sections were blocked with 10% normal goat serum and 0.5% BSA and stained with Alexa Fluor 488-conjugated goat anti-muse IgG (Molecular Probes, Eugene Oreg.) or fluorescein isothiocyanate (FITC)-conjugated goat F(ab')z anti-mouse C3 (ICN, Costa Mesa, Calif.). Sections were viewed with a Zeiss Axioscop 2 plans fluorescent microscope and the digital images analyzed using Axiovision 4.2 software. The mean intensity of the green fluorescence per glomerulus was calculated for 17-33 glomeruli/mouse and the groups compared.

Statistical Analysis. Survival curves were plotted by the method of Kaplan and Meier and compared by the log-rank test. Proteinuria scores are expressed as the mean±SEM. Histopathology scores are expressed as the mean±SD and compared by the two-tailed Mann-Whitney U test. Mean antibody levels and spleen and lymph nodes weights were compared using unpaired T tests. Graphical and statistical analyses were performed using GraphPad Prism v4.0 (GraphPad Software, San Diego, Calif.).

Results

CRP treatment prolongs survival of MRL/lpr mice. MRL/lpr mice were treated with 200 μg of CRP s.c., at 6 weeks. At this point, mice are without overt disease as demonstrated by low levels of autoantibodies (FIG. 3) and the absence of measurable proteinuria or azotemia (FIG. 2). Another group of mice was injected with 200 μg of human CRP at 13 weeks. Survival was measured in both groups of CRP-treated mice and compared to saline-treated mice (FIG. 2A). The saline-treated mice had a median survival of 18.5 weeks whereas mice treated early with CRP had a median survival of 23 weeks (p<0.05 vs. saline). Unexpectedly, mice treated with CRP at 13 weeks had the most prolonged survival with a median survival of 29 weeks (p<0.05 vs. saline). Thus, treatment with CRP at a very active stage of disease is at least as effective as early treatment, suggesting that CRP treatment reverses ongoing inflammation. These results show a prolonged effect of CRP with survival extended for several months after a single injection.

CRP protects MRL/lpr mice from the development of proteinuria and azotemia. We further analyzed the mice described in FIG. 2A for the onset of proteinuria and azotemia. Control mice developed significant proteinuria (>3+) at a mean age of 11 weeks, whereas early CRP treatment delayed the age of onset of proteinuria until 22.5 weeks (p<0.0001) (FIG. 2B). The decreased level of proteinuria was associated with a similarly decreased level of azotemia (BUN) (FIG. 2D) suggesting a role in protecting overall renal function in addition to glomerular permeability.

In mice treated with CRP at 13 weeks, a rapid decrease in proteinuria was observed (FIG. 2C). Similarly, the increase in BUN values seen in control mice at week 18 was delayed until week 22 in CRP-treated mice (FIG. 2D). A significant discrepancy between levels of BUN and survival was seen in treated mice. Despite the continued low levels of BUN in the mice treated with CRP early, these mice had a shorter survival than mice treated with CRP later.

CRP decreases anti-dsDNA antibodies in MRL/lpr mice. We also examined the levels of anti-dsDNA in the MRL/lpr mice (FIG. 3). IgG anti-dsDNA in control mice increased markedly at 13-14 weeks. This increase was not seen in mice treated with CRP at 6 weeks (FIG. 3C). In two separate experiments, mice treated with CRP prior to disease onset had decreased levels of IgG anti-dsDNA antibodies at week 13 or 14 (FIGS. 3A and 3C). IgM anti-dsDNA levels were lower and were not affected by CRP treatment (FIG. 3B). Anti-dsDNA antibodies were also measured by the Farr assay at week 13 (FIG. 3D). Antibodies detected by this assay are of high avidity for DNA and have been associated with renal disease in SLE (23). As shown in FIG. 4), 8 out of 9 control mice had elevated levels of anti-dsDNA by this assay, compared to 1 out of 5 CRP-treated mice ($p<0.05$, Fisher's test). Late CRP treatment did not change autoantibody levels at 18 weeks (FIG. 3C). Later effects of CRP on autoantibody levels could not be determined, because of deaths in the untreated mice. CRP treatment did not affect hypergammaglobulinemia, as no difference in total serum IgG concentration was seen between early CRP-treated and saline-treated mice (data not shown).

CRP treatment delays the onset of lymphadenopathy in MRL/lpr mice. One of the most prominent clinical features of disease in the MRL1 1pr mouse is the development of massive lymphadenopathy. Lymphadenopathy is due to the infiltration of double negative T cells that proliferate extensively in the absence of Fas-mediated apoptosis. Lymphadenopathy of mice described in FIG. 2 was scored weekly on a 3 point scale as described (22). Early CRP treatment prevented the development of lymphadenopathy. All untreated mice had extensive (3+) lymphadenopathy by week 14, whereas in the CRP-treated mice ⅛ had developed none, ⅝ had developed mild, and ⅖ had developed moderate lymphadenopathy by 28 weeks (data not shown).

The ability of CRP treatment to prevent lymphadenopathy was confirmed quantitatively in a second experiment in which mice were killed at week 15 and 17. At this time one of the saline treated mice had died and the remaining all developed 5+ proteinuria Mice treated with CRP at 6 weeks had a marked decrease in lymph node weight compared to the saline-treated controls at both 15 and 17 weeks ($p<0.01$) (FIG. 4A). Mice that were treated at 15 weeks with CRP also showed a significantly decreased lymph node weight at 17 weeks compared to the saline group ($p<0.05$). Spleen weights were not affected by CRP treatment (FIG. 4B).

Renal Pathology. Renal histopathology was determined on kidneys from the same groups of mice. Glomerular lesions consisted of neutrophilic inflammation with or without glomerular capillary thrombosis; necrosis and leakage of protein rich fluid into the glomerulus; increased glomerular cellularity; glomerular hypertrophy; mononuclear cell infiltration; and periglomerular fibrosis and/or crescent formation (FIGS. 5A and 5B). Other renal lesions consisted of tubular proteinuria with or without tubular degeneration and necrosis; interstitial and periglomerular histiocytic and lymphoplasmacytic inflammation (FIG. 5C); and perivascular histiocytic and lymphoplasmacytic inflammation (FIG. 5)). The combined and individual glomerular lesion scores as well as the tubular/interstitial and perivascular scores are summarized in FIG. 5. At 15 weeks, the glomerular lesions and tubular and interstitial renal lesions were more severe for the controls than for the early CRP-treated mice. Likewise, at 17 weeks, the glomerular and tubular and interstitial renal lesions were greater for the controls than for both the early and late CRP-treated animals. With the exception of one early CRP-treated mouse that did not respond to treatment and was excluded from the analysis, the lesions in the early and late CRP-treated mice were similar in severity. While early and late CRP treatment clearly ameliorated the interstitial inflammation and the glomerular and tubular lesions in these mice, it had no effect on the perivascular inflammation (FIGS. 5D and 6). The histologic appearance of kidneys from representative mice from each group at 17 weeks is shown in FIG. 6. It can be seen from FIG. 6, panel D that saline-treated mice showed severe glomerular infiltration and hypercellularity whereas mice treated with CRP, whether early or late, had decreased severity glomerular lesions and much less cellular infiltration (FIG. 6, panels F&H). Examination of lesions at low power showed that the effect of CRP on glomerular lesions did not apply to perivascular lesions (FIG. 6, panels E&G).

Immunofluorescence of renal lesions. To determine whether CRP might affect renal disease by decreasing IC deposition in the kidneys, tissue sections from mice with active disease were stained for the presence of C3 and IgG. Immunofluorescence was quantitated by digital imaging microscopy. No significant differences in IgG or C3 deposition were observed between any of the treatment groups at 15 or 17 weeks (data not shown).

Lymph node/salivary gland pathology. Mandibular lymph nodes and sublingual, submandibular, and parotid salivary glands were also examined histologically. The lymph nodes from the saline-treated mice were larger than those of the early and late CRP-treated mice, primarily due to reduction in the degree of paracortical lymphoid hyperplasia in the CRP-treated mice. The lesions in the salivary glands consisted of mild to moderate, perivascular histiocytic and lymphoplasmacytic inflammation, and in about half the mice, minimal to mild, interstitial histiocytic and lymphoplasmacytic inflammation with insignificant loss of glandular parenchyma. There were no apparent differences in the lesion distribution or severity between the saline and CRP-treated mice (data not shown).

Figure 7:
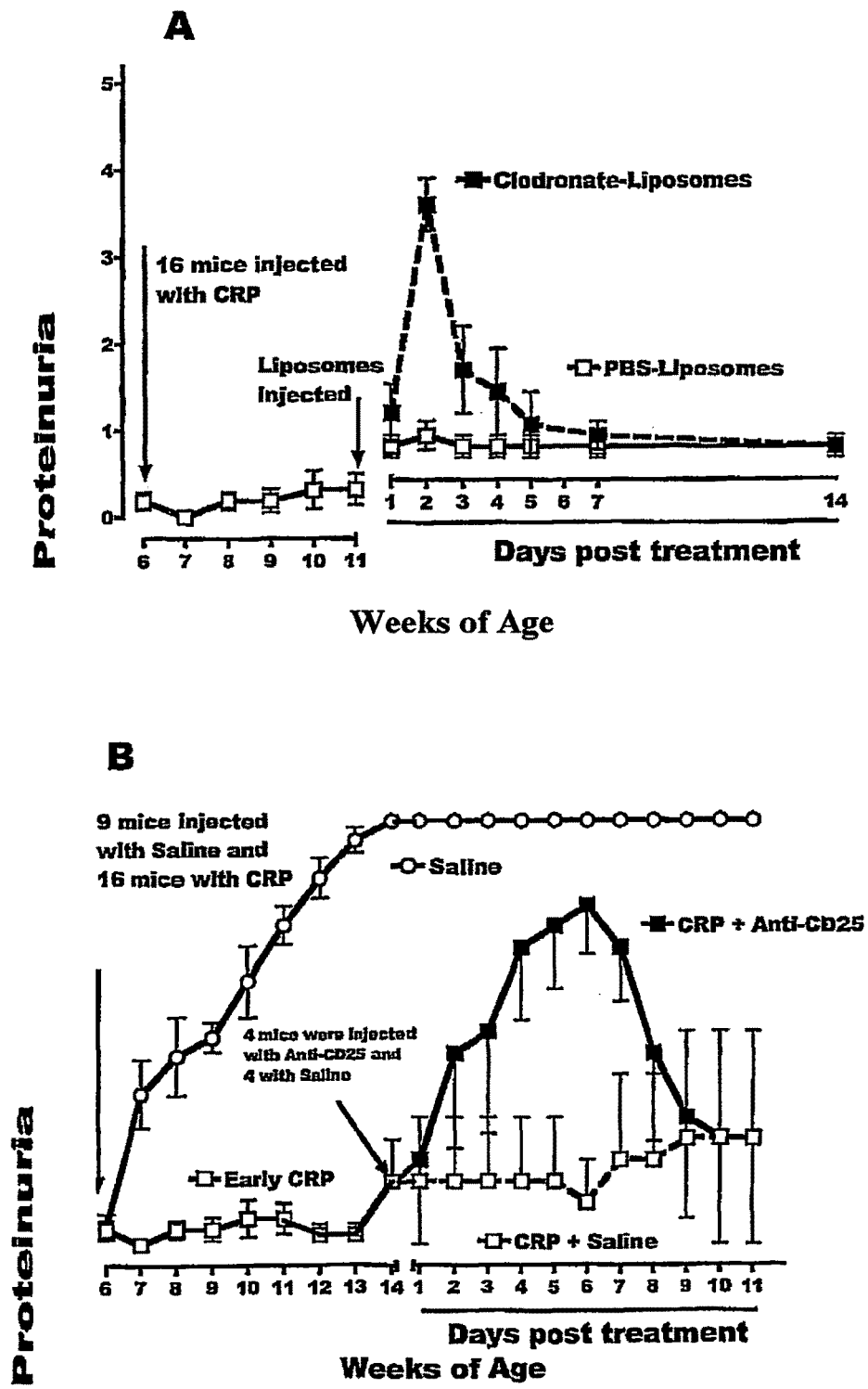
FIG. 7 shows that protection by CRP is not affected by macrophage depletion, but is aborted by anti-CD25 treatment MRL/lpr mice were treated with 200 μg of CRP or saline at 6 weeks. A. At 11 weeks, mice in the CRP group were injected with either Clodronate liposomes or PBS liposomes (n=8). B. At 14 weeks, mice that were previously treated with PBS liposomes we treated with 1 mg of PC61 (n–4). Proteinuria was monitored daily for 7 days after injection PC61 and liposomes. Proteinuria was monitored using Albustix. Mean scores±SEM are shown.

Treatment of mice with ongoing suppression of disease with anti-CD25 reverses protection. The sustained protection of mice by a single treatment with CRP suggested that suppression of disease involved the generation of a long-lasting suppressive factor or cell. We first tested whether macrophages could be the source of suppression. A group of early CRP-treated mice was injected with Clodronate liposomes or PBS liposomes at 11 weeks to eliminate macrophages from the liver and spleen (18, 19). This treatment produced only a small, transient rise in proteinuria and no reversal of ongoing suppression of disease in CRP-treated mice (FIG. 7A). Untreated NM/1pr mice had significant proteinuria at this time (FIG. 7B).

Another mechanism of suppression that has been recently re-described is the induction of regulatory T cells (Treg). These cells are long lasting and could provide ongoing suppression of disease activity. The mAb to CD25, PC61 has been shown to deplete Treg in several models (20, 24). We decided to test whether PC61 would affect ongoing suppression of disease by CRP. Mice treated with CRP at 6 weeks were treated with a single injection of 1 mg of PC61 at 14 weeks. FIG. 7B shows weekly proteinuria values with the week following PC61 injection expanded to show daily readings. PC61-treated mice showed a rapid increase in proteinuria that lasted for 7 days and then decreased without additional CRP treatment. These results suggest that Treg may be responsible for the long term suppression of disease in CRP-treated mice.

Discussion

Previous studies demonstrated that CRP can delay the onset of proteinuria and prolong survival of NZB/W mice (13-15). We initially demonstrated that CRP would protect mice from the accelerated autoimmunity induced by injection of chromatin, a major autoantigen in SLE (13). Protection was associated with a transient decrease in autoantibodies but no long-lasting effects on autoantibodies were seen. Szalai et al showed that NZB/W mice made transgenic for human CRP also had prolonged-survival and decreased renal pathology, yet these mice did not have decreased autoantibody levels (14). More recently, we reexamined the effect of CRP on NZB/W mice by injecting young mice with CRP before disease onset or older mice during the active phase of disease (15). CRP treatment was found to have a marked effect on both proteinuria and survival, and it was shown that CRP could actually reverse disease in mice with established nephritis. Again, no appreciable effect of CRP on autoantibody levels was seen. These findings suggested that the activity of CRP on SLE in the NZB/W-model may be distal to autoantibody generation In fact, the rapid reversal of disease activity in mice with established disease was strongly indicative of this possibility (25).

The major new finding presented here is that human CRP protects mice from a rapidly progressive form of nephritis in the MRL/lpr model. The protection was induced by a single injection of human CRP and this effect was long lasting. The result of CRP treatment was most profound for the course of nephritis but autoantibody formation and lymphadenopathy were also markedly inhibited, indicating a systemic effect. Considering our previous data with the NZB/W model, the effect of CRP on autoantibody levels in MRL/lpr mice was surprising. The MRL/lpr mice treated early with CRP had a markedly delayed onset of anti-dsDNA antibodies by ELISA. The MRLIlpr mouse differs in several respects from the NZB/W model (16). First, the disease onset in MRL/lpr is more rapid and the mice suffer 50% mortality by 20 weeks. Second, the MRL/lpr mice develop massive lymphadenopathy due to a defect in the Fas gene and consequent failure of T cells to undergo apoptosis. Third, MRL/lpr mice have more extensive disease involvement of other organs including the lungs, skin and heart.

It appears that the protection of mice from autoimmune nephritis by CRP is primarily not due to a decrease in autoantibody production but rather to a decreased response to IC deposited in the organs. Quantitation of IC or complement deposition in the kidneys by immunofluorescence of mice treated with CRP or controls of the same age showed no significant differences. Moreover, late CRP treatment was effective despite the absence of a decrease in autoantibody. These findings suggest that CRP may not affect the deposition of IC or complement in the lesion. This is perhaps not surprising as recent studies have shown that eliminating the anti-DNA antibody response in TLR9 deficient, MRL/lpr mice did not change levels of IC in glomeruli (26).

The other unique finding presented here is that CRP markedly suppressed the lymph node proliferation that is so prominent in these animals. It is generally thought that lymph node enlargement is due to the proliferation of T cells outside the lymph nodes, which are then recruited (27). Although the mechanism for this effect on T cell recruitment to the lymph node remains unknown, it implies that the effects of CRP are not restricted to antigen sequestration or enhanced clearance of nuclear antigens as these processes are thought to be distinct from T cell recruitment.

CRP had no measurable effect on renal vasculitis. Different mechanisms and cytokines are responsible for glomerular disease as opposed to renal perivascular inflammation. Selective suppression of CSF-1 was shown to decrease renal disease without affecting renal vasculitis (28). Similar findings were seen in mice deficient in IL-12, which showed a marked decrease in glomerular inflammation but no decrease in perivascular infiltration (22).

One possible mechanism for the protection against autoimmune disease mediated by CRP is enhanced clearance of nuclear antigens expressed on apoptotic cells (29). This mechanism has been dubbed the waste disposal hypothesis. Deficiencies in proteins involved in apoptotic cell clearance including serum amyloid P component (SAP), mer, C1q, DNase 1 and secreted IgM, have been associated with the development of autoantibodies (30). In most cases overt autoimmune disease in these mice has required additional lupus-associated background genes, such as lpr (31-33). Although this mechanism may contribute to the delayed development of anti-dsDNA antibodies in CRP-treated mice, our findings do not support autoantigen clearance as the primary mechanism by which CRP protects against lupus nephritis. In the current study, although autoantibody levels were decreased by early CRP treatment, late CRP treatment was at least as effective in controlling nephritis and prolonging survival without affecting anti-dsDNA. In addition, CRP treatment decreased inflammatory changes in the kidney rapidly and without affecting IC deposits in glomeruli. A dissociation between IC deposition and glomerular inflammation has previously been described in FcγR deficient NZB/W mice (34) and heterozygous IFNγ deficient MRL/lpr mice (35).

We hypothesize that the main mechanism by which CRP protects mice from disease is through modulating the inflammatory response to IC. CRP protects mice from a variety of inflammatory challenges (8, 36). We have shown that the effect of CRP on LPS-induced death has an absolute requirement for FcγR. Protection from LPS is associated with the ability of CRP to induce synthesis of IL-10 by macrophages and with FcγRIIb-dependent regulation of inflammatory cytokine production (9). Similarly we have shown that in the NTN model, CRP requires not only the presence of FcγRI (unpublished data) but also the expression of IL-10 (15). Thus CRP has regulatory activity in several inflammatory conditions that do not involve autoantibodies.

The mechanism by which early CRP treatment provides long term protection from renal disease, lymphadenopathy and autoantibody formation remains uncertain. The effects of a single injection of CRP on renal disease were apparent for at least 4 months in MRL/lpr mice. It is very unlikely that CRP is sequestered in a compartment where it could continue to contribute to immune modulation as the half-life of CRP in the mouse is very short (on the order of 4 hours) (37) and the vast majority of CRP is cleared by hepatocytes (38). Taken together, the data suggest active suppression by a CD25 bearing T cell. The lack of an effect of Clodronate liposomes on ongoing suppression of CRP-treated mice argues against the presence of a suppressive macrophage at least during the later period of protection. The results from the NTN and lupus models presented here and previously (39) are consistent with the induction by CRP of a rapid anti-inflammatory response that includes IL-10 release and the reversal of renal inflammation. Others have shown that Treg may be generated when antigen is presented in the presence of IL-10 or TGF-β (40). Thus, the initial response to CRP may provide an environment for the generation of Treg cells capable of maintaining control of the developing autoimmune disease in these mice for a prolonged period. In this context the ability of CRP to bind to apoptotic cells may provide an appropriate stimulus for the induction of Treg. Gershov et al. (11) found that human macrophages ingesting apoptotic cells opsonized with CRP and complement produced increased amounts of TGF-β.

In summary, CRP treatment of mice resulted in a high degree of protection from clinical and laboratory parameters of SLE. Although the effect of CRP on renal function was most notable, a profound effect on lymphadenopathy was also seen and anti-dsDNA antibodies were decreased. The prolonged suppression of disease following a single injection of CRP suggested that ongoing regulation of the inflammatory response did not depend on the continued presence of CRP. The reversal of disease suppression by anti-CD25 treatment suggested a possible role for Treg.

Whether treatment of autoimmune mice with CRP are transportable to human autoimmune disease is uncertain. However, these findings suggest the possibility that SLE can be regulated in a very substantial way without systemic immunosuppression. If the induction of a long-lasting immunoregulation can be induced by CRP treatment, it could have a significant impact on therapy of lupus nephritis. In a practical sense for humans CRP treatment would have to be given after the onset of disease. Mice treated early with CRP had a more pronounced decrease in anti-dsDNA antibody levels and levels of BUN. However, late CRP treatment of mice was equally effective in decreasing proteinuria, renal pathology and lymphadenopathy. Thus treatment of humans with CRP may prove to be effective despite the differences in effects on various disease aspects in mouse models.

Further Examples

The above results extend the observations of a protective effect of CRP in NZB/W mice to more rapidly developing disease in the MRL/lpr model. CRP decreased renal disease in three separate cohorts of MRL/lpr mice including a total of 29 control mice, 38 mice treated early with CRP and 13 mice treated late with CRP. For mice in which renal pathology and immunohistochemistry was completed only one of 14 mice given early CRP treatment failed to respond. In MRL/lpr mice we observed a suppressive effect of early CRP treatment on the development of autoantibodies and lymphadenopathy as well as on nephritis and renal pathology. This indicates a systemic effect on autoimmunity in addition to a local anti-inflammatory action on IC-mediated renal disease. Interestingly, CRP treatment did not decrease perivascular inflammation in the kidneys or splenomegaly. This same pattern of protection was seen by other investigators in MRL/lpr mice genetically deficient in the chemokine, MCP-1 (CCL2) (17). This suggests that CRP treatment may either decrease renal production of MCP-1 or block the response to it. MCP-1 is synthesized by tubular epithelial cells and other cells in the kidney of MRL/lpr mice and plays an important role in renal inflammation by attracting circulating CCR2+ monocytes and T cells into the kidney (17a).

There are at least two, non-mutually exclusive possible mechanisms for the effectiveness of CRP in treating SLE (18a, 19a). Each mechanism will be examined further in the proposed work.

The First Mechanism is that CRP Acts as a Scavenger for Apoptotic Cells, Nuclear Debris and Other Autoantigens that are Immunogens in SLE.

According to this "waste disposal hypothesis", CRP and other innate opsonins including serum amyloid P component (SAP), natural IgM antibody and complement act to clear these autoantigens in a noninflammatory and nonimmunogenic form (reviewed in (20a)). An increasing body of evidence suggests that the autoantibody response in SLE is driven by endogenous nuclear antigens released from dead and dying cells or exposed in blebs on the surface of apoptotic cells. The characteristics of the antibody response to chromatin in autoimmune mice and humans suggest that this is an antigen-driven response (21a, 22a). The idea that the source of this endogenous antigen is apoptotic cells is based on the identification of autoantigens exposed on apoptotic cells (23a) and the association of deficiencies in components of clearance pathways with the development of autoimmunity (20a, 24a). Studies in mice have found that CRP and SAP produce major changes in the rate and path of chromatin clearance (25a, 26a). In addition to the effects of CRP and SAP on clearance of chromatin, both pentraxins also bind to apoptotic cells (27a, 28a), probably through interactions with membrane phospholipids. CRP increases the uptake of apoptotic cells by macrophages through complement-dependent opsonization (28a) and both CRP and SAP enhance FcgR-dependent phagocytosis of apoptotic cells (29a). Gershov et al. (28a) reported that opsonization of apoptotic cells by CRP and complement has anti-inflammatory effects in human macrophages.

CRP binds to determinants exposed during apoptosis and increases the uptake of apoptotic cells by mouse and human macrophages in vitro (FIG. 8A) (28a, 29a). We have extended these studies to a commonly used in vivo assay for apoptotic cell uptake (FIG. 8B) (30a). Mouse thymocytes treated for 18 h with dexamethasone were opsonized with CRP and injected into mice that had been treated 4 days before with thioglycollate. Peritoneal cells were collected after 30 min and uptake of thymocytes by macrophages determined on stained slides. CRP opsonization increased the uptake of the apoptotic thymocytes by peritoneal macrophages in normal mice. CRP-dependent uptake of apoptotic thymocytes was decreased in $C3^{-/-}$-mice and $FcgRI^{-/-}$ ($CD64^{-/-}$) mice. These results suggest that under inflammatory conditions where cells are being injured, CRP binding increases the ability of macrophages to remove these dead and dying cells using complement and FcgR. The uptake of apoptotic cells opsonized with CRP and complement increased production of TGF-b in human macrophage cultures (28a). Since CRP binds to antigenic determinants that are important in the induction of lupus autoantibodies, it also has the potential to suppress autoantibody responses by preventing or altering antigen presentation.

When pathways for the clearance of apoptotic material fail and autoantibodies are produced, one of the results is the activation of innate immune responses. It has recently been determined that both human and mouse SLE are characterized by the activation of interferon (IFN)-α dependent genes. This cytokine profile has been dubbed the interferon signature (31a, 32a). The most potent producer of IFN-α is the plasmacytoid dendritic cell (PDC) (33a). A positive feedback mechanism has been described whereby PDC react with nuclear antigen-antibody complexes through intracellular toll-like receptors (TLR) following FcγR-mediated internalization to stimulate the production of IFN-α (34a). Interferogenic nuclear antigens include apoptotic and necrotic cells, small nuclear ribonucleoproteins (snRNPs) and chromatin. The TLR utilized is related to its ability to interact with RNA (TLR7 and 8) or DNA (TLR9) that are present in these antigens. The continual stimulation of cells by IC containing TLR ligands is thought to contribute to the perpetuation of autoimmune disease in SLE (reviewed in (33a, 35a). Although PDC are the source of IFN-α, a similar FcγR-TLR dependent pathway induces maturation and cytokine secretion by myeloid DC (36a). The generation of IFN-α further activates DC to continue the cycle of presentation of autoantigens. Whereas complexes between autoantibodies and autoantigens stimulate FcγR and TLR to produce IFN-α, complexes between CRP and autoantigens are in general non-stimulatory and non-inflammatory ((28a) and our preliminary results). Thus, CRP may break the inflammatory cycle induced by lupus IC. In preliminary experiments using human PBMC, anti-RNP antibodies, when combined with apoptotic U937 cells (not shown), or purified snRNPs (FIG. 9A) induced IFN-α. Although CRP binds to both apoptotic cells and to purified snRNPs, the addition of CRP to these autoantigens failed to induce IFN-α and suppressed the IFN-α response to IC. The addition of CRP or CRP-snRNP also increased production of IL-10, an anti-inflammatory cytokine (FIG. 9B). The experiments in Objective 2 will test the effectiveness of CRP in removing apoptotic cells, blocking immunization with nuclear autoantigens, and regulating the DC response to IC containing nuclear autoantigens.

The Second Mechanism by which CRP Protects from Lupus Nephritis is Through the Generation of Anti-Inflammatory Cytokines and/or Suppressor Cells, which Decrease the Inflammatory Response to IC and Other Stimuli.

CRP is an acute phase protein synthesized by hepatocytes in response to the inflammatory cytokines, IL-6 and IL-1. The peak level of CRP in the circulation is 24-48 h after an acute stimulus, a time when CRP could contribute to the resolution of inflammation and to the clearance of damaged tissue. Protective, anti-inflammatory effects of CRP have been shown by several investigators. Increasing CRP levels by injection or in CRP transgenic mice protects mice against endotoxin and platelet activating factor induced shock (37a, 38a) and chemoattractant-induced alveolitis (39a). We have shown that the protective effect of CRP in endotoxin shock is associated with a regulation of cytokines that occurs through FcgR (38a). CRP binds to human and murine FcgRI and FcgRII (40a, 41a). CRP increases the synthesis of the anti-inflammatory cytokine IL-10 and decreases the synthesis of pro-inflammatory cytokines tumor necrosis factor (TNF)-a and IL-12 after LPS challenge. The enhanced IL-10 synthesis as well as the protective effect in endotoxin shock requires FcR g-chain consistent with an FcgRI-dependent effect. CRP interaction with FcgRIIb is also important, since CRP-treated FcgRIIb$^{-/-}$ mice were more susceptible to endotoxin shock and produced higher levels of TNF-a and IL-12 (38a). Several investigators have described alternative activation pathways for macrophages depending on the stimulus. We hypothesize that CRP induces macrophages to become "type II" macrophages, a phenotype described by Mosser et al. for macrophages responding to LPS in the presence of IC (42a, 43a). These macrophages regulate inflammatory responses by increased synthesis of IL-10 and decreased synthesis of IL-12.

Figure 10:
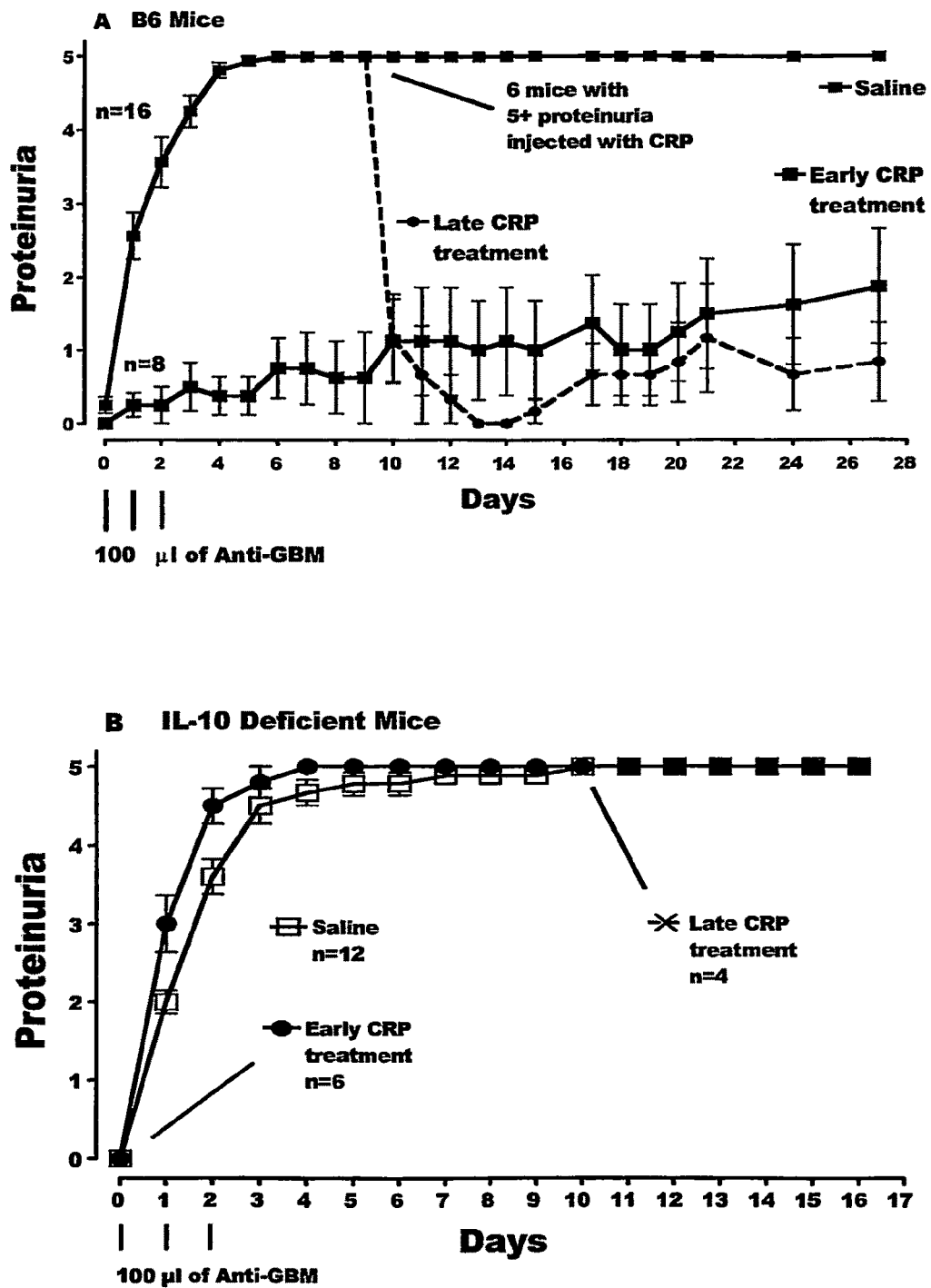
FIG. 10 shows that CRP treatment suppresses NTN in B6 but not IL-10$^{-/-}$ mice. NTN was induced in B6 or IL-10$^{-/-}$ mice by immunization with rabbit IgG on day −5 and injection of 100 μl anti-GBM on days 0, 1 and 2. Early and late s.c. injections of 200 μg CRP treatment were given on day 0 or 9. Proteinuria values are means±SEM using Albustix. Grades of proteinuria are expressed as 0, none; 1+, trace; 2+, 30 mg/dl; 3+, 100 mg/dl; 4+, 300 mg/dl; 5+, >2000 mg/dl. A. In B6 mice early CRP treatment prevented development of proteinuria following anti-GBM injection and late CRP treatment rapidly decreased proteinuria to undetectable levels. B. In IL-10$^{-/-}$ mice proteinuria developed following anti-GBM treatment, but CRP treatment had no effect.

The anti-inflammatory activity of CRP contributes to the rapid reversal of nephritis in MRL/lpr mice. We established the NTN model to study the effects of CRP on IC-induced glomerulonephritis (11a). NTN is induced by immunization of mice with rabbit IgG 5-7 days before injection of rabbit anti-GBM. The importance of macrophages and FcgR in generating pathology has been well-documented (44a-46a). In addition, the NTN model is rapid, does not require autoantibodies and allows manipulation of receptors and cytokines through the use of genetically-deficient mouse strains. Briefly, we found that C57BL/6 (B6) mice were completely protected from proteinuria when injected on day 0 with 200 μg of CRP and showed rapid reversal of proteinuria when injected on day 9 during ongoing active nephritis (FIG. 10A). Both groups of CRP-treated mice also had significantly decreased glomerular lesions compared to saline-treated NTN mice on day 11. Periodic acid-Schiff (PAS) staining showed a prominent disruption of basement membrane organization in the saline-treated NTN mice. Glomeruli from both groups of CRP-treated mice appeared nearly normal on H & E and PAS staining.

Figure 11:
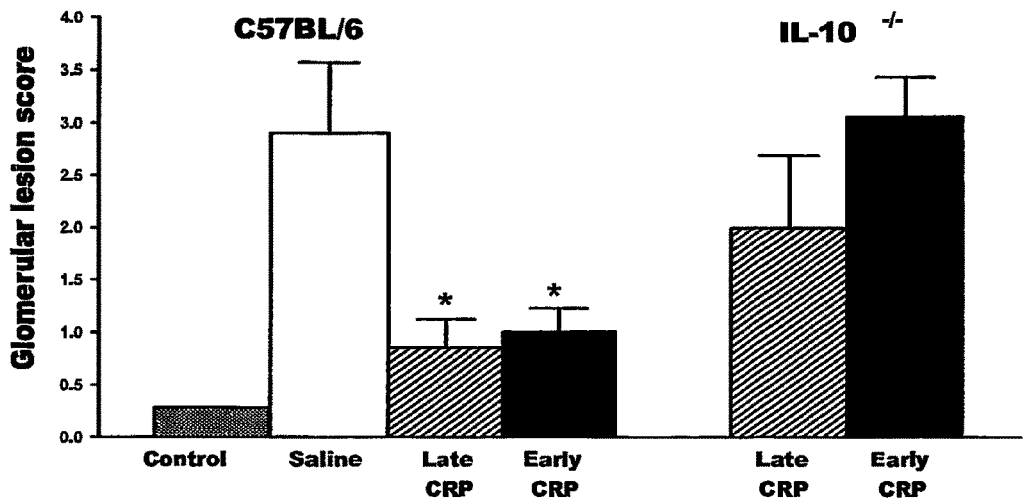
FIG. 11 shows that CRP treatment decreases glomerular lesions in NTN. Mice with NTN were killed on day 11 after CRP treatment on day 0 (early) or 10 (late). Slides were read by a veterinary pathologist who was blinded to the treatment groups. A 4 point scale was used based on the number of glomeruli involved and the severity of the lesions (1, <10%, minimal; 2, 10-25%, mild; 3, 50%, moderate; 4, >50%, marked). At least 30 glomeruli were scored for each mouse. Mean±SD. *, p<0.05
Figure 12:
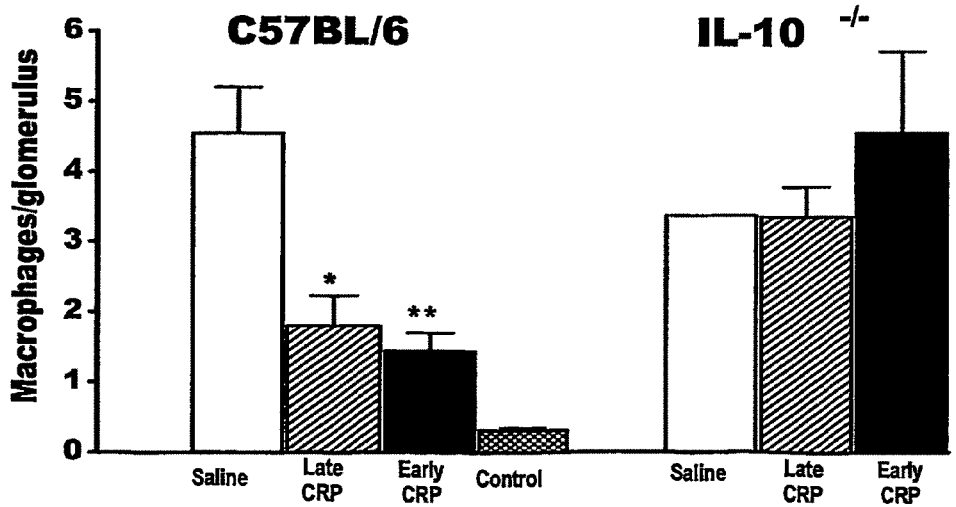
FIG. 12 shows that CRP treatment decreases macrophage infiltration in NTN. Mice with NTN were killed on day 11 after CRP treatment on day 0 (early) or 10 Gate) and kidney sections stained for CD68+ macrophages using immunoperoxidase. Mean±SEM CD68+ cells per glomerulus are shown. * p<0.05, ** p<0.01 vs. saline.
Figure 13:
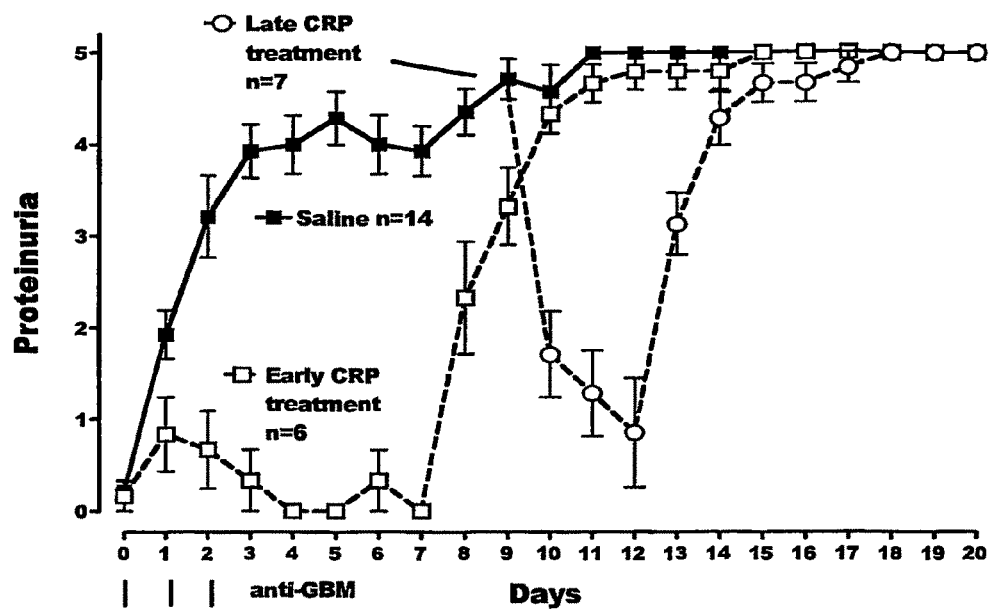
FIG. 13 shows that CRP treatment of FcgRI deficient mice provides early protection from NTN, but protection is not sustained. NTN was induced in FC☐RI$^{-/-}$ mice with three injections of anti-GBM as described and proteinuria was measured daily. CRP-treated mice received 200 μg of CRP at day 0 (Early CRP treatment) or at day 9 (late CRP treatment).

The most significant findings from the NTN model were that protection by CRP was associated with decreased glomerular lesions and infiltration of glomeruli by macrophages (FIGS. 11, 12) and that CRP treatment was ineffective in IL-10$^{-/-}$ mice (FIGS. 10B, 11 and 12). When NTN was induced in IL-10$^{-/-}$ mice, a similar pattern of proteinuria to WT mice developed. However, injection of CRP provided no protection to IL-10$^{-/-}$-mice at either day 0 or 10, indicating that both prevention and treatment of NTN by CRP requires IL-10 (FIG. 10B). IL-10$^{-/-}$ mice had more severe glomerular pathology that was unaffected by CRP treatment, and macrophages infiltrating glomeruli were also not affected by CRP treatment of these mice (FIGS. 11 and 12). Since we had previously found that the synthesis of IL-10 in response to CRP and LPS was dependent on FcγR (38a), we tested the requirement for FcγRI in protection against NTN. CRP produced only transient protection from NTN when given to FcγR$^{-/-}$ mice on day 0 or day 9. After 3-6 days, the CRP-treated mice all developed 5+ proteinuria that continued for the duration of the experiment (FIG. 13). These results showed that FcγR was required for protection. The early transient protection afforded by CRP in the FcγR$^{-/-}$ mice was complement-dependent, as it was eliminated in mice treated with cobra venom factor (CVF). CVF treatment did not interfere with the protective effect of CRP in B6 mice suggesting an overriding effect of the FcγRI-dependent mechanism.

Figure 14:
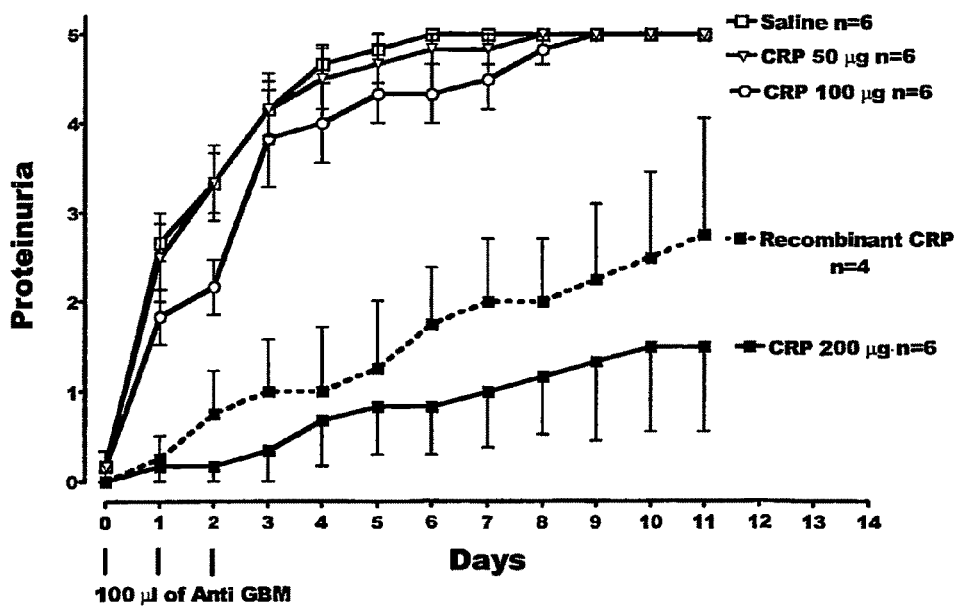
FIG. 14 shows that recombinant CRP is effective in treating NTN. NTN was induced as described in FIG. 9. Mice were treated on day 0 with different concentrations of purified human CRP (CRP) or with 200 μg of recombinant CRP. Proteinuria values are means±SEM using Albustix.

Additional experiments showed that CRP protection of mice from proteinuria after induction of NTN was dose dependent (FIG. 14). One injection of 200 μg of CRP was effective with some delay in proteinuria after injection of 100 μg of CRP and no effect of lower doses. Importantly, commercial recombinant CRP produced in E. coli was also effective at a dose of 200 μg in this model. The availability of commercial recombinant material is an advantage for the clinical use of CRP.

Figure 15:
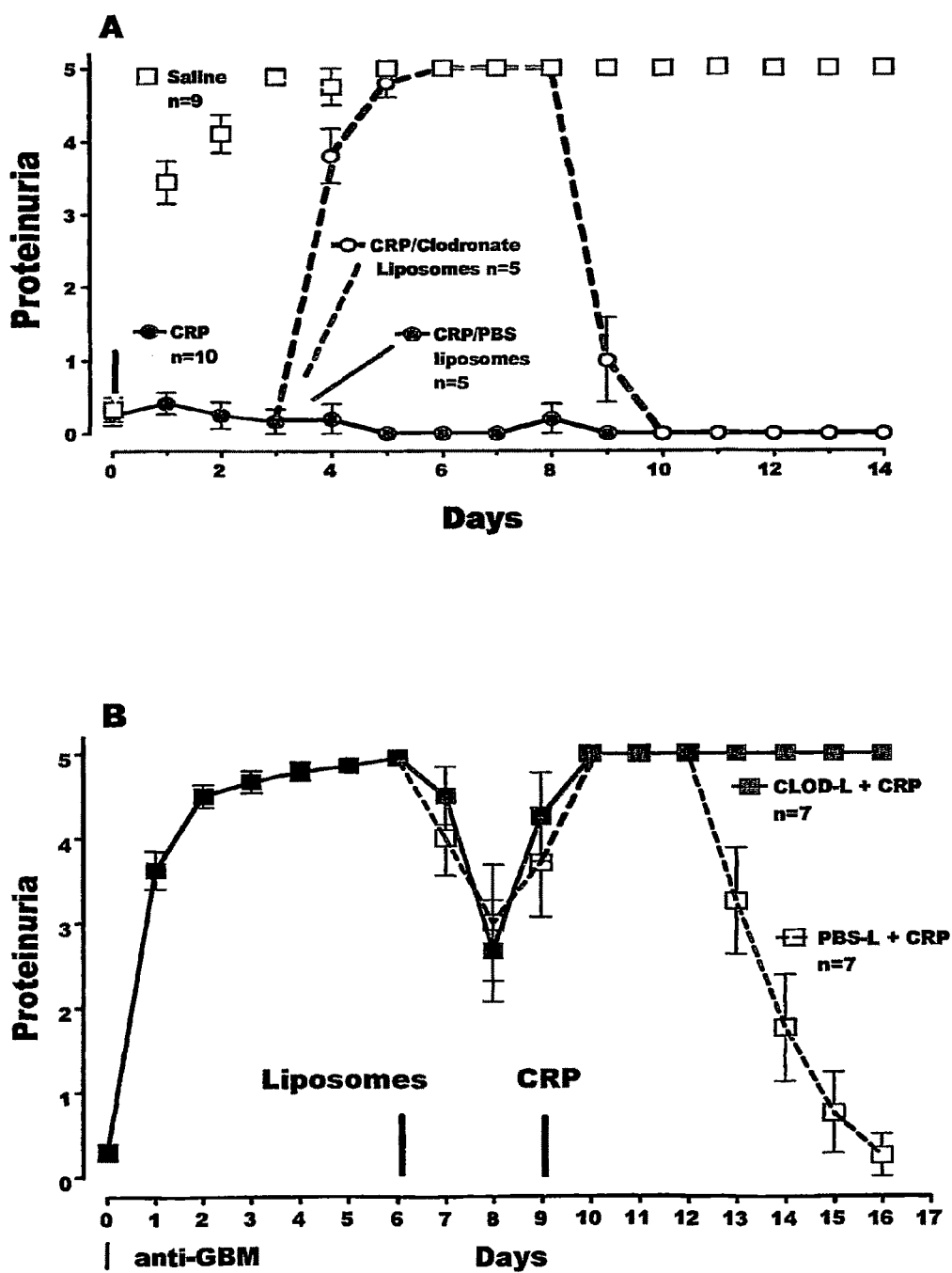
FIG. 15 shows that Macrophage depletion blocks the ability of CRP to treat NTN. A. NTN was induced in B6 mice by a single injection of anti-GBM on day 0. Mice were treated with CRP or saline on day 0. CRP-treated mice were injected i.v. with Clodronate or control liposomes on day 3. The decreased proteinuria seen with CRP injection was temporarily reversed by Clodronate injection. B. NTN was induced in B6 mice by a single injection of anti-GBM on day 0. Mice were treated with Clodronate or control liposomes on day 6 and with 200 μg CRP on day 9. Prior treatment with Clodronate liposomes blocked the ability of CRP to decrease proteinuria. In both panels, proteinuria values are means±SEM using Albustix. The scale is 0, none; 1+, trace; 2+, 30 mg/dl; 3+, 100 mg/dl; 4+, 300 mg/dl; 5+, >2000 mg/dl).

We also demonstrated a role for macrophages in the protection from NTN mediated by CRP. We injected mice i.v. with liposomes containing Clodronate to selectively deplete macrophages from the liver and spleen for a period of 5-7 days (47a). We have confirmed that our protocol eliminates virtually all of the macrophages in the liver and >95% of the macrophages in the spleen (48a). Mice injected with CRP on day 0 of NTN initially had low proteinuria. Injection of these mice with Clodronate liposomes reversed protection for 5 days corresponding to the approximate period of macrophage depletion (FIG. 15A). We also treated NTN mice with Clodronate liposomes or control liposomes on day 6 after they had developed proteinuria (FIG. 15B). CRP was injected 3 days after the liposomes. In mice injected with control liposomes, there was a delayed response but CRP suppressed disease with proteinuria becoming undetectable 7 days after CRP injection. In contrast, mice treated with Clodronate liposomes were not protected by CRP, indicating a requirement for macrophages in the reversal of proteinuria.

These results indicate that the cell depleted by i.v. Clodronate treatment is required to initiate and maintain CRP-dependent disease suppression in this short term model. Based on our studies of NTN we believe that injection of CRP stimulates macrophages through FcγRI to produce IL-10 and become anti-inflammatory type II macrophages that suppress renal disease.

Once IC are deposited in the kidneys of mice with SLE, an inflammatory cascade is initiated by infiltrating macrophages and T cells that results in nephritis and renal failure. Many of the inciting factors and cytokine pathways apply to other manifestations of disease as well. An overview of the pathological cascade in MRL/lpr (based on published studies) is provided here (15a, 17a, 49a, 50a). Nephritis in the MRL/lpr mouse is highly dependent on MCP-1 (CCL2) production by intrinsic renal cells stimulated by circulating leukocytes secreting IL-1β. In this model circulating leukocytes are stimulate by IC locally in the kidney as they traverse the renal microvasculature leading to IL-1β secretion (51). The responding cells are primarily tubular epithelial cells (EC), which respond with the production of MCP-1. MCP-1 in turn induces inflammatory and renal toxic cytokines including TNFα, IFN-γ and colony stimulating factor (CSF)-1. More importantly, MCP-1 recruits circulating monocytes and T cells which are responsible for much of the renal pathology. The T cells in turn are stimulated to produce IL-2 perpetuating T cell proliferation and cytokine production. The recruited macrophages are responsible for producing inflammatory cytokines and mediating renal damage. In addition to these factors, TEC undergo apoptosis, which can further increase the immunological response to autoantigens on the cell surface. The central role of MCP-1 has been shown by several investigators and therapeutic intervention proposed (17a, 52a, 53a). Furthermore, increased levels of MCP-1 and mRNA for MCP-1, in the urine of patients with SLE have been reported and these levels correlate with lupus nephritis activity (54a, 55a).

The goal is to dissect this complex cascade to identify the level at which CRP intercedes and to determine the target cell of CRP. To help determine at which point in this pathway CRP treatment was having an effect, we analyzed mRNA for IL-2, IFN-γ, MCP-1 (CCL2) and MIP-1α (CCL3) in the kidneys of CRP-treated and control MRL/lpr mice at 17 weeks of age. We found no change in expression of IFN-γ and a small decrease in expression of IL-2 in CRP-treated mice that was not significant, suggesting no direct effect on T cell infiltration or stimulation Renal cells are responsible for much of the chemokine synthesis in these mice, and MCP-1 and MIP-1α mRNA levels were both decreased in the kidneys of early CRP-treated compared to control mice (FIG. 16, $p<0.05$ for MCP-1, n.s. for MIP-1α). There was a string difference in the correlation between glomerular lesion scores (GLS) and cytokine/chemokine expression in CRP-treated mice compared to saline-treated mice. In control MRL/lpr mice there was a close correlation between levels of MCP-1 and GLS ($p<0.05$) consistent with the well-described role of MCP-1 in attracting macrophages into the kidney. However, in the CRP-treated mice there was no correlation between MCP-1 levels and GLS suggesting that MCP-1 was not capable of attracting macrophages and inducing disease (FIG. 16B). A similar dissociation between cytokine/chemokine expression and renal pathology in CRP-treated mice is apparent for MIP-1α (FIG. 16A) and IFN-γ (FIG. 16C). These findings suggest an effect of CRP on the circulating monocytes/macrophages that are recruited to the glomeruli and perhaps on the receptor for MCP-1, CCR2. This hypothesis will be further tested wherein chemokines and chemokine receptor changes will be measured in kidney, spleen and PBMC. In addition we will directly examine the effect of CRP on monocyte infiltration into inflammatory sites.

The suppression of nephritis in MRL/lpr mice by CRP extended several months beyond the time of treatment. While a single injection of CRP might transiently result in apoptotic cell clearance and generation of anti-inflammatory cytokines, there must be another mechanism to convert this into a long-term regulation of inflammatory disease. We have evidence, reported in (12a), that in MRL/lpr mice, regulatory T cells (Trig) rather than macrophages are necessary to maintain suppression of nephritis following early CRP treatment MRL/lpr mice given early CRP treatment to suppress renal disease were injected with 1 mg of anti-CD25 mAb (PC61) at 14 weeks of age. This mAb has been shown to effectively deplete CD25+ T cells including natural Treg and PC61 treatment of MRL/lpr mice significantly reduced the number of CD25 bright, CD4+ cells in the blood 4 days after treatment. Mice with low proteinuria following early CRP treatment that received a single injection of PC61 developed significant (3 to 4+) proteinuria over the following week. This result suggests that depletion of CD25 bright, CD4+ T cells, characteristic of natural Treg, interrupts the CRP-induced suppression of disease in these mice. In contrast to other biological therapeutics, such as treatment with antibodies or receptor antagonists for individual cytokines, CRP treatment is likely to induce a natural suppressive pathway, initiated by macrophages (or DC) and maintained by Treg. The induction of Treg may be key to the long-term effectiveness of CRP treatment in murine lupus. Both naturally occurring and antigen-induced Treg are capable of controlling autoimmunity and autoimmune disease. An established mechanism for the generation of antigen-induced Treg (specifically, IL-10 producing Tr1) is to stimulate naïve Th cells with antigen in the presence of IL-10. Thus, CRP binding to lupus autoantigens and induction of IL-10 may provide an appropriate environment for the generation of Treg in SLE. Experiments also test the role of Treg in the long term suppression of nephritis in CRP-treated MRL/lpr mice.

Development of CRP as a Therapeutic Agent for Lupus Nephritis.

These experiments use the MRL/lpr model to develop CRP for the treatment of lupus nephritis. We found previously that a single CRP injection, either before or after disease onset, suppressed nephritis and extended survival of MRL/lpr mice. These experiments further the findings to clinical use. The first experiment relates to the repeated treatment of mice showing proteinuria to provide additional benefit. The second determines the spectrum of disease manifestations that are controlled by CRP treatment. The third is directed to the side effects associated with treatment. In addition, CRP mutants with changes in ligand binding, complement activation and interaction with FcγR are evaluated in the MRL/lpr model. These experiments provide insight into the mechanism of CRP action and assist in developing alternative forms of treatment with greater benefit or fewer side effects.

Determining the Effectiveness of Repeated CRP Treatment on Autoimmune Disease in MRL/lpr mice.

For repeated treatment to be effective in mice, it is necessary to prevent the antibody response to human CRP that develops in these mice 4-8 weeks after injection. This should not be a problem in humans, because CRP is a normal serum protein with no polymorphisms in the coding region. We have achieved tolerance to human CRP by injecting ultracentrifuged CRP into neonatal B6 mice. The majority (9/15) of these mice failed to produce anti-CRP antibodies when treated as adults with our standard s.c. injection of 200 µg CRP.

A similar approach is used in MRL/lpr mice. These mice are injected with CRP within 24 h of birth to induce tolerance and given CRP treatment at 6 weeks of age and followed weekly by weight, azotemia, and proteinura. Azotemia (BUN) is determined as urea nitrogen in serum samples. Twenty-four hour urine samples are collected in metabolic cages and assayed for protein by Bradford assay and creatinine by a colorimetric assay. Proteinuria is expressed as mg urine protein/urine creatinine. Additional CRP injections are given to mice when elevated proteinuria develops and the response is monitored. Serum is tested for anti-dsDNA and anti-CRP antibodies over the course of the experiment.

A second approach to avoiding immunogenicity of CRP is to use recombinant mouse CRP. Mice are expected to be tolerant to the mouse protein. We clone the mouse CRP gene (61), which we have obtained from Dr. Richard Mortensen (Ohio State University), into a baculovirus vector. Mouse CRP is produced in *Trichoplusia ni* larvae and purified by affinity chromatography on PC-Sepharose as we have described for human CRP (62a). Additional purification is by ion exchange FPLC on Mono-Q. Endotoxin is removed if necessary. We inject 200 µg of mouse CRP to achieve the levels of human CRP that are effective. Mice do not normally produce more than 5 µg/ml of CRP even during the acute phase response (63a). Repeated injections of mouse CRP are given when elevated proteinuria develops.

Figure 17:
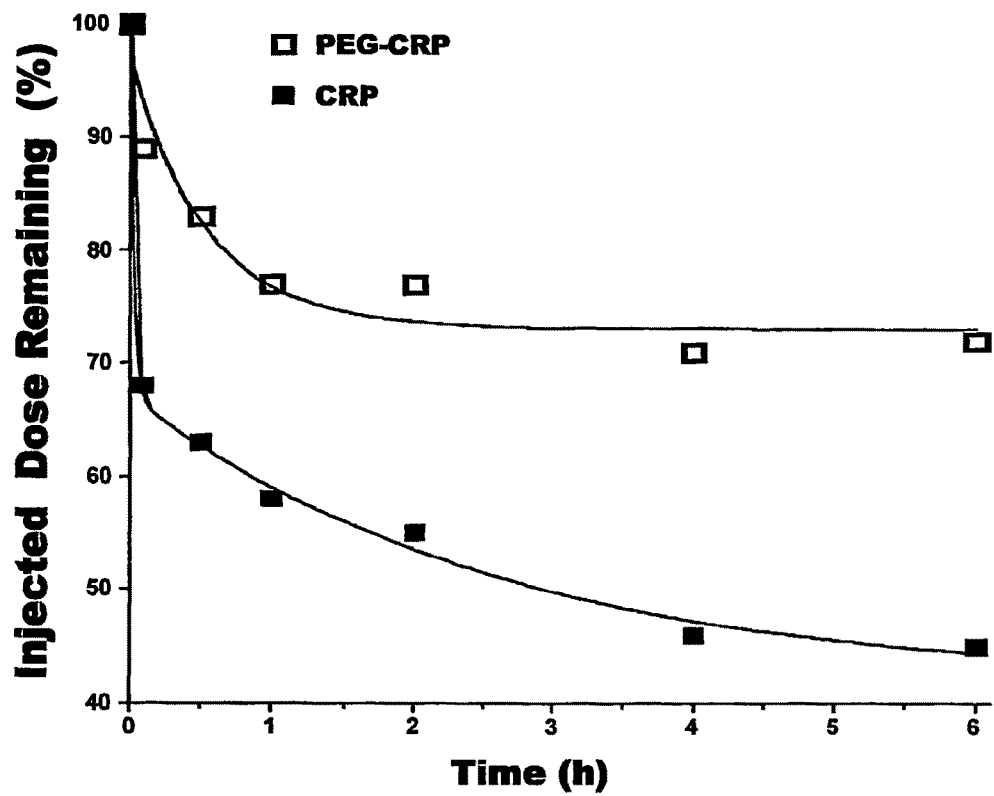
FIG. 17 shows that PEGylation slows the clearance of CRP. CRP was modified with PEG, isolated on PC-Sepharose, radioiodinated and injected i.v. into mice. The % injected cpm recovered in TCA precipitates of the plasma is shown.
Figure 18:
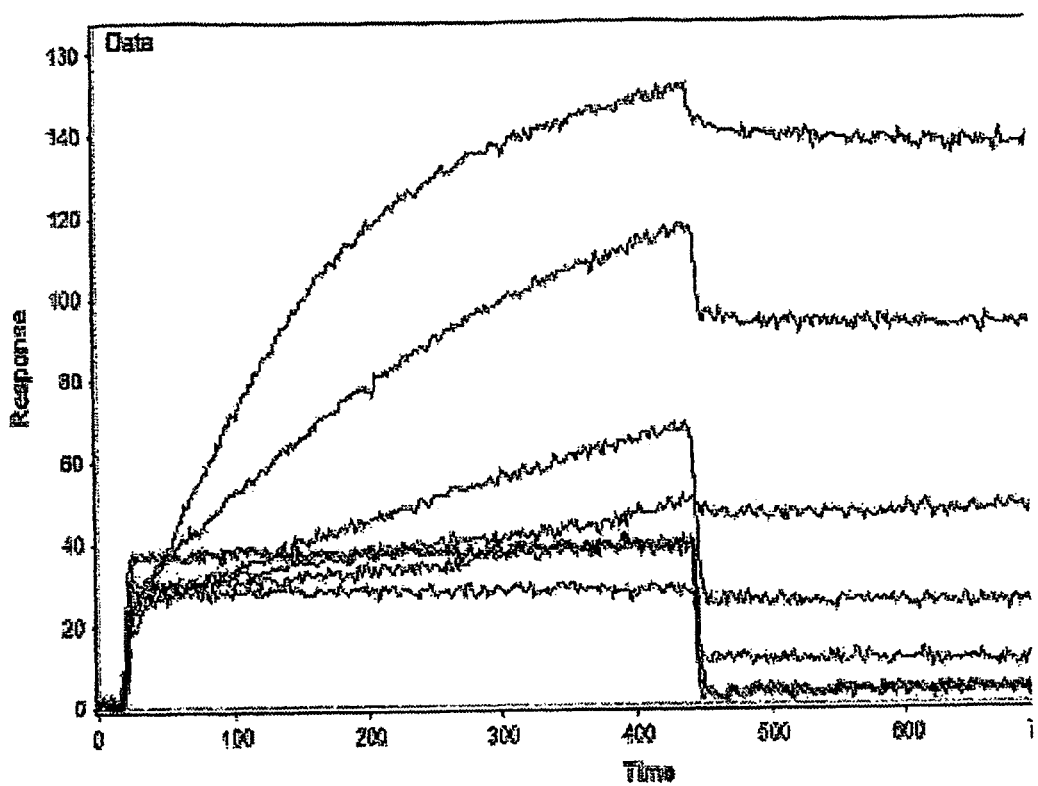
FIG. 18 shows that CRP binding to FcγRI as measured by surface plasmon resonance. FcγRI (1000 μRIU) were immobilized CRP was injected @ 42 nM, 84 nM, 169 nM and 338 nM. Data are recorded as resonance units over time after injection. The $K_D$ was determined to be $1.83 \times 10^{-7}$ M.

One of the limiting factors of using CRP therapeutically is its rapid clearance rate, especially in mice where it has a half life of 2.5 h (64a). In man the half-life of CRP is 19 h (65a) suggesting that treatment of human patients with SLE could be more effective. The use of polyethylene glycol modification (PEGylation) extends the half life and decreases immunogenicity of proteins (66a), and has allowed decreased dosing schedules with prolonged efficacy of biological agents such as IL-2, IFN-α, and GM-CSF. Thus PEGylation is a promising approach to the issues of rapid clearance and immunogenicity of human CRP in mouse models. To test this approach, we modified CRP with 20 kDa succinimidylpropionic acid PEG as described (67a), isolated it on PC-Sepharose (indicating retention of biological activity), radioiodinated it and compared its clearance to that of unmodified human CRP in mice (67a) (See attached FIG. 17). PEGylation decreased the initial rapid clearance and the later slow clearance phase so that a stable plateau level of 72% of the injected PEG-CRP remained in the blood at 6 h compared to 45% of unmodified CRP. The effectiveness of a single injection of different doses of PEG-CRP is compared to unmodified CRP using the NTN model where we have dose response data. Antibody responses to human CRP are also tested in these mice 4 weeks after injection. If PEG-CRP is less immunogenic and/or more effective than unmodified CRP, it is to be tested in the MRL/lpr model.

Data Analysis and Predicted Outcomes. The effectiveness of these approaches in treating lupus nephritis is determined by comparing the time of development of proteinuria and azotemia, and by renal pathology scores at time of death. The effectiveness of each of these approaches is assessed by comparing the survival of mice given repeated CRP injections to mice given a single injection of CRP. Survival and onset of proteinuria is plotted using the Kaplan Meier method and compared by the log rank test using GraphPad Prism 4.0 (Graph Pad Software, San Diego, Calif.). Mean azotemia and autoantibody levels are compared using unpaired T tests. Pathology scores are compared using Mann-Whitney U tests for nonparametric data.

We predict that repeated injection of CRP exhibits additional benefit over a single injection. These results would support the use of repeated injections of CRP in patients to treat recurrence of lupus nephritis or prophylactically on a repeated schedule to prevent lupus flares.

Alternative approaches. If the above approaches to reducing immunogenicity of CRP are unsuccessful in MRL/lpr mice, an alternative is to use an immunosuppressive drug along with CRP to block the development of immunity to human CRP. A similar approach with methotrexate in combination with mouse/human mAb to TNF-α is routinely used in rheumatoid arthritis patients to prevent the development of human anti-chimeric antibodies. The addition of cyclophosphamide to the immuno-suppressive agent, CTLA4Ig has proven to be much more effective than CTLA4Ig alone in suppression of lupus nephritis (14a, 68a). Combined treatment of mice with cyclophosphamide and CRP are tested for effective suppression of disease and prevention of an anti-CRP response as described above.

Determine the Spectrum of Disease Manifestations that is Controlled by CRP Treatment and the Potential Side Effects of Treatment.

Some CRP-treated MRL/lpr mice, especially in the early treatment group, died without developing elevated proteinuria or BUN. This indicates that some manifestations of the disease were not effectively treated by CRP. Of the parameters measured, splenomegaly and perivascular infiltrates in the kidneys were not affected by CRP treatment (12a). Moderate inflammatory infiltrates were also observed in salivary glands of about 50% of the mice at 17 weeks of age with no apparent effect of CRP treatment. Additional aspects of disease that are seen in some of these mice are skin lesions, pulmonary and salivary gland infiltrates, arthritis, vasculitis, thrombosis and myocardial infarction (1). Unlike previous studies, complete tissue analysis of multiple organs from sacrificed animals are done. For example, lung and salivary gland sections are examined for degree of macrophage and lymphocytic infiltration and pathology. Kidney and lung sections are stained using immunoperoxidase for macrophages (CD68+), CD4+ T cells, DN T cells (CD3+, B220+) and proliferating cells (PCNA+) (17). We hypothesize, based on results thus far, that CRP has its primary effect on inflammatory macrophages and T cells responding to MCP-1, and less effect on T cell proliferation. The results of these studies together with further analysis of chemokine and cytokine expression elucidate the pathways being blocked by CRP and shed light on the mechanisms involved.

Data Analysis and Predicted Outcomes. Data collected are expressed as numbers of cell subsets per field determined by counting and pathology scores as described above. Results for CRP-treated and control mice are compared using Mann-Whitney U tests for nonparametric data. Based on our preliminary findings we predict that CRP will prevent the infiltration of inflammatory macrophages into tissues, including the lung, but will have less effect on perivascular T cell proliferation and vasculitis.

Effect of CRP on cardiovascular disease. One of the major advantages of the MRL/lpr mouse over the NZB/W mouse is the presence of cardiac involvement. Myocardial infarction was reported in 14% of MRL/lpr mice at 24 weeks of age (69a). Diet manipulation increased the incidence of myocardial infarction in MRL/lpr mice to 53% (69a). Although it is very unlikely that short term CRP treatment exacerbates atherosclerosis, it has been reported that elevated baseline CRP levels correlate with atherosclerosis in humans (70a, 71a). Indeed several investigators have suggested a cause and effect relationship between CRP and vascular injury. However, it should be noted that studies of mice expressing CRP as a transgene have shown no consistent effect on atherogenesis despite long term CRP expression and accelerated atherosclerosis due to apolipoprotein E-deficiency (72a-74a). Cardiac muscle are examined for evidence of previous infarction and aortic sections are examined for atherosclerotic lesions in control and CRP-treated MRL/lpr mice at 24 weeks of age. If there is any indication of an increase in cardiac involvement in CRP-treated mice, a more complete study are conducted in which an atherogenic diet is used to increase the extent of coronary artery disease.

Effect of CRP on resistance to infection Short term experiments with CRP injection into mice have shown a protective effect on bacterial infection and on exposure to LPS. However, it is unknown whether long term resistance to infection is affected by the immunomodulatory activity of CRP. Therefore, we determine whether CRP-treated MRL/lpr mice have increased susceptibility to infection during suppression of disease activity. MRL/lpr mice are treated with CRP or saline at 6 weeks of age and tested for susceptibility to infection at 10 weeks of age before their autoimmune disease is severe. Mice are challenged with *S. pneumoniae* intravenously and intranasally as previously described (75a). We have established these infection models in our laboratory. Resistance to endotoxin exposure are tested as previously described by us and others (38a, 40a, 76a).

Data Analysis and Predicted Outcomes.

The effects on cardiovascular disease are analyzed by comparing the frequency of disease in CRP-treated and control mice using Fisher's exact test. The effects on susceptibility to infection and shock are determined by comparison of survival curves from CRP-treated and control mice challenged with bacteria or endotoxin. It is unlikely that CRP treatment increases cardiac involvement or leads to enhanced susceptibility to infection. However, these are important questions considering the large body of clinical data showing an association between elevated CRP levels and atherosclerosis and outcomes of acute coronary events.

To Screen CRP Mutants for Testing as Therapeutic Agents in MRL/lpr Mice.

These experiments will determine which activities of CRP are important for immunomodulation in vivo. Breeding of genetic deficiencies onto the MRL/lpr model has made some analysis of disease mechanisms possible. However, the same pathways that are most likely to be important for CRP suppression of disease, FcγR and complement, contribute to IC-mediated autoimmune diseases. Using modified CRP has the advantage of allowing studies in mice with intact innate and adaptive immune systems. We have developed a panel of CRP molecules with single amino acid changes that affect binding to human FcγR and/or C1q (77). Additional mutants in the ligand (PC)-binding site and C1q binding site have been described by Agrawal et al. (78a-80a). Candidate CRP mutants are screened for binding to autoantigens, mouse FcγR and mouse C1q to develop reagents for in vivo testing in the MRL/lpr model.

A double mutant of CRP (F66A/E81A) has been described that lacks binding to PC-conjugated proteins and to pneumococcal C polysaccharide (78a). We use an ELISA format to test the binding of this mutant to ligands important in SLE, snRNPs and chromatin (81). Binding to specific Sm/RNP proteins is also assessed by blotting on purified snRNPs. Purified snRNPs, and Sm/RNP-coated ELISA plates are obtained from Inova (San Diego, Calif.). The ability of mutant CRP to bind to intact nuclear antigens is tested by immunofluorescence on fixed Hep-2 cells. Binding to apoptotic cells are tested by flow cytometry using mouse thymocytes treated overnight with 1 µM dexamethasone. It is expected, based on cross-inhibition experiments that the F66A/E81A mutant will lack binding to these antigens (82a, 83a). If the F66A/E81A mutant retains binding to autoantigens, additional ligand-binding mutants are made and tested.

We have identified a region of homology between CRP and the FcγR binding sequences of IgG. We have identified single amino acid mutations within this region that affect CRP binding to human FcγRI, FcγRIIa or both (77a). These mutants were identified using a flow cytometry binding assay to FcγR-transfected COS-7 cells. We have found CRP binding to recombinant human FcγRI from R&D Systems (Minneapolis, Minn., Cat#1257-FC-050) using an ELISA format Binding of CRP to FcγRIIa by ELISA is a quality control assay done by R&D Systems (Cat#1330-CD-050), and they have also found mouse and human CRP binding to mouse FcγRIV (personal communication, Sara Brokaw, R&D Systems). Recombinant human and mouse FcγR are available from R&D Systems for the extracellular domains of each of the receptors. We screen previously described CRP mutants for binding to wells coated with 5 µg/ml recombinant mouse FcγRI (CD64), FcγRIIb (CD32), FcγRIII (CD16-1) and FcγRIV (CD16-2), using HRP-goat-anti-human CRP (Bethyl, Montgomery, Tex.) as a detection reagent We use flow cytometry of leukocytes from FcγR-deficient mice to confirm the binding specificities of selected mutants as previously described for wild type CRP (42a).

Activation of mouse complement by mutant CRP molecules is measured initially using a mouse C1q ELISA, similar to the assay we used for human C1q (77a). CRP is bound to PC-BSA-coated microtiter wells and binding of purified mouse C1q tested Mouse C1q is purified from mouse serum by IgG affinity chromatography. CRP mutants with decreased C1q binding are tested for complement activating ability by preincubating complexes of CRP and pneumococcal C-polysaccharide in fresh mouse serum and testing for C4 consumption using a C4 hemolytic assay that we have adapted to mouse serum (62a).

We have expressed mutant CRP molecules in baculovirus vectors and can produce mg quantities by injection of *T. ni* larvae (62a). CRP is purified by affinity chromatography on PC-Sepharose, followed by FPLC on Mono Q. Mutants lacking PC binding are purified by anti-CRP affinity chromatography and Mono Q. Preparations are tested for purity on SDS-PAGE and endotoxin by quantitative chromogenic *Limulus amebocyte* lysis (LAL) assay (Biowhittaker). If needed, endotoxin are removed by passage over Acticlean Etox (Sterogene) to reach a level of less than 3 EU endotoxin/mg CRP.

Mutant CRP molecules are used to answer several important questions about the mechanism of CRP action in suppressing autoimmune disease. If the ability of CRP to bind to apoptotic cells and/or nuclear antigens are required for its activity, a ligand-binding site mutant are less effective than wild type CRP. We use complement and FcγR-deficient mice to determine whether CRP-dependent clearance of apoptotic cells requires complement activation and/or binding to FcγR. The mutant CRP molecules are used to confirm these findings in wild type mice and to test the importance of this pathway in decreasing autoantibodies and nephritis in MRL/lpr mice.

Data Analysis and Predicted Outcomes. Appropriate mutant CRP molecules are characterized in vitro and then tested in the MRL/lpr model using the methods described above. We use CRP mutants lacking individual activities in the MRL/lpr model to help dissect the roles of these pathways in suppression of nephritis and delay of autoantibody synthesis. Based on studies of NTN, we predict that CRP binding to FcγRI are required for suppression of active nephritis. Our preliminary experiments indicate that FcγRIIb may not be required for CRP suppression of NTN. We will treat MRL/lpr mice with 200 µg of wild type or mutant CRP at 6 weeks of age and compare autoantibody levels and renal disease to MRL/lpr mice treated with 200 μg of a control protein (pharmaceutical grade human serum albumin). Comparison of CRP mutants lacking individual functions will allow us to directly determine the requirements for ligand binding, and binding to FcγRI, and FcγRIIb in this model.

Finally, some data suggest that CRP activation of complement may exacerbate myocardial injury following infarction (85a, 86a). If there is evidence that CRP increases cardiovascular disease in MRL/lpr mice, we will test a mutant CRP lacking C1q-binding to see if this side effect is decreased.

REFERENCES

First Set

1. Du Clos T W. Function of C-reactive protein. *Ann Med* 2000; 32:274-8.
2. Du Clos T W. The interaction of C-reactive protein and serum amyloid P component with nuclear antigens. *Mol Biol Rep* 1996; 23:253-60.
3. Volanakis J E. Human C-reactive protein: expression, structure, and function. Mol *Immunol* 2001; 38:189-197.
4. Gabay C, Roux-Lombard P, de Moerloose P, Dayer J-M, Vischer T, Gueme P-A. Absence of correlation between interleukin 6 and C-reactive protein blood levels in Systemic Lupus Erythematosus compared with Rheumatoid Arthritis. J Rheumatol 1993; 20:815-821.
5. Du Clos T W, Mold C. C-reactive protein: an activator of innate immunity and a modulator of adaptive immunity. *Immunol Res* 2004; 30:261-78.
6. Heuertz R M, Dongyuan X, Samols D, Webster R O. Inhibition of C5a des Arg-induced neutrophil alveolitis in transgenic mice expressing C-reactive protein. *Am J Physiol;* 1994; 266:L649-L654.
7. Heuertz R M, Piquette C A, Webster R O. Rabbits with elevated serum C-reactive protein exhibit diminished neutrophil infiltration and vascular permeability in C5a-induced alveolitis. *Am J Pathol* 1993; 142:319-328.
8. Xia D, Samols D. Transgenic mice expressing rabbit C-reactive protein are resistant to endotoxemia. *Proc Natl Acad Sci USA* 1997; 94:2575-80.
9. Mold C, Rodriguez W, Rodic-Polic B, Du Clos T W. C-reactive protein mediates protection from lipopolysaccharide through interactions with Fc gamma R. *J Immunol* 2002; 169:7019-25.
10. Szalai A J, Nataf S, Hu X-Z, Barnum S R. Experimental allergic encephalomyelitis is inhibited in transgenic mice expressing human C-reactive protein *J Immunol* 2002; 168:5792-5797.
11. Gershov D, Kim S, Brot N, Elkon K B. C-reactive protein binds to apoptotic cells, protects the cells from assembly of the terminal complement components, and sustains an antiinflammatory innate immune response: implications for systemic autoimmunity. *J Exp Med* 2000; 192:1353-1363.
12. Mold C, Baca R, Du Clos T W. Serum amyloid P component and C-reactive protein opsonize apoptotic cells for phagocytosis through Fcγ receptors. *J Autoimmun* 2002; 19:147-54.
13. Du Clos T W, Zlock L T, Hicks P S, Mold C. Decreased autoantibody levels and enhanced survival of (NZB×NZW) F1 mice treated with C-reactive protein. *Clin Immunol Immunopathol* 1994; 70:22-7.
14. Szalai A J, Weaver C T, McCrory M A, van Ginkel F W, Reiman R M, Kearney J F, Marion T N, Volanakis J E. Delayed lupus onset in (NZB×NZW)FI mice expressing a human C-reactive protein transgene. *Arthritis Rheum* 2003; 48: 1602-11.
15. Rodriguez W, Mold C, Kataranovski M, Hutt J, Marnell L L, Du Clos T V Reversal of ongoing proteinuria in autoimmune mice by treatment with C-reactive protein. Arthritis *Rheum* 2005; 52:642650.
16. Theofilopoulos A N, Dixon F J. Murine models of systemic lupus erythematosus. *Adv Immunol* 1985; 37:269-391.
17. Du Clos T W. C-reactive protein reacts with the U1 small nuclear ribonucleoprotein. *J Immunol* 1989; 143:2553-9.
18. van Rooijen N, Sanders A. Liposome mediated depletion of macrophages: mechanism of action, preparation of liposomes and application *J Immunol Methods* 1994; 174:83-93
19. Du Clos T W, Volzer M A, Hahn F F, Mao R, Mold C, Searles R P. Chromatin clearance in C57BU10 mice: interaction with heparan sulphate proteoglycans and receptors on Kupffer cells. *Clin Exp Immunol* 1999; 117:403-11.
20. Oldenhove G, de Heusch M, Urbain-Vansanten G, Urbain J, Maliszewski C, Leo 0, Moser M. CD4+ CD25+ regulatory T cells control T helper cell type 1 responses to foreign antigens induced by mature dendritic cells in vivo. *J Exp Med* 2003; 199:259-66.
21. Rubin R L. Enzyme-linked immunosorbent assay for anti-DNA and antihistone antibodies. In: Rose N R, Friedman H, Fahey J L, editors. Manual of Clinical Laboratory Immunology. Washington: ASM; 1986. p. 744-749.
22. Kikawada E, Lenda D M, Kelley V R. IL-12 deficiency in MRL-Faslpr) mice delays nephritis and intrarenal IFN-gamma expression, and diminishes systemic pathology. *J Immunol* 2003; 170:3915-25.
23. Smeenk R J, Brinkman K, van den Brink H G, Westgeest A A. Reaction patterns of monoclonal antibodies to DNA. *J Immunol* 1988; 140:3786 92.
24. McHugh R S, Shevach E M. Cutting edge: depletion of CD4+CD25+ regulatory T cells is necessary, but not sufficient, for induction of organ-specific autoimmune disease. *J Immunol* 2002; 168:597983.
25. Du Clos T V C-reactive protein as a regulator of autoimmunity and inflammation. *Arthritis Rheum* 2003; 48:1475-7.
26. Christensen S R, Kashgarian M, Alexopoulou L, Flavell R A, Akira S, Shlomchik M J. Toll-like receptor 9 controls anti-DNA autoantibody production in murine lupus. *J Exp Med* 2005; 202:321-331.
27. Zhou T, Bluethmann H, Eldridge J, Berry K, Mountz J D. Origin of CD4-CD8-B220+ T cells in MRL-lpr/lpr mice. Clues from a T cell receptor beta transgenic mouse. *J Immunol* 1993; 150:3651-67.
28. Tesch G H, Maifert S, Schwarting A, Rollins B J, Kelley V R. Monocyte chemoattractant protein 1-dependent leukocytic infiltrates are responsible for autoimmune disease in MRL-Faslpr) mice. *J Exp Med* 1999; 190:1813-24.
29. Walport M J. Lupus, DNase and defective disposal of cellular debris. *Nat Genet.* 2000; 25:1356.
30. Kim S J, Gershov D, Ma X, Brot N, Elkon K B. Opsonization of apoptotic cells and its effect on macrophage and T cell immune responses. *Ann NY Acad Sci* 2003; 987:68-78.
31. Ehrenstein M R, Cook H T, Neuberger M S. Deficiency in serum immunoglobulin IgM predisposes to development of IgG autoantibodies. *J Exp Med* 2000; 191:1253-8.
32. Boes M, Schmidt T, Linkemann K, Beaudette B C, Marshak-Rothstein A, Chen J. Accelerated development of IgG autoantibodies and autoimmune disease in the absence of secreted IgM. *Proc Natl Acad Sci USA* 2000; 97: 1184-9.

34. Botto M, Walport W. C1q, autoimmunity and apoptosis. *Immunobiology* 2002; 205:395-406.

35. Clynes R, Dumitru C, Ravetch J V. Uncoupling of immune complex formation and kidney damage in autoimmune glomerulonephritis. *Science* 1998; 279:1052-1054.

36. Balomenos D, Rumold R, Theofilopoulos A N. Interferon-gamma is required for lupus-like disease and lymphoaccumulation in MRL-lpr mice. *J Clin Invest* 1998; 101:364-71.

37. Heuertz R M, Xia D, Samols D, Webster R D. Inhibition of C5a des Arg-induced neutrophil alveolitis in transgenic mice expressing C-reactive protein. *Am J Physiol* 1994; 266:L649-L654.

38. Baltz M L, Rowe I F, Pepys M B. In vivo turnover studies of C-reactive protein. *Clin Exp Immunol* 1985; 59:243-50.

39. Hutchinson W L, Noble G E, Hawkins P N, Pepys M B. The pentraxins, C-reactive protein and serum amyloid P component, are cleared and catabolized by hepatocytes in vivo. *J Clin Invest* 1994; 94:1390-1396.

40. Carvalho-Pinto C E, Garcia M I, Mellado M, Rodriguez-Frade J M, Martin-Caballero J, Flores J, Martinez A C, Balomenos D. Autocrine production of IFN-gamma by macrophages controls their recruitment to kidney and the development of glomerulonephritis in MRL11pr mice. *J Immunol* 2002; 169:1058-67.

41. Groux H, O'Garra A, Bigler M, Rouleau M, Antonenko S, de Vries J E, Roncarolo M G. A CD4+ T-cell subset inhibits antigen-specific T-cell responses and prevents colitis. *Nature*. 1997; 389:737-42.

REFERENCES A

Second Set of References

1a. Hahn, B. H. 2002. An overview of the pathogenesis of systemic lupus erythematosus. In *Dubois' Lupus Erythematosus*. D. J. Wallace, and B. H. Hahn, eds. Lippincott Williams and Wilkins, Philadelphia, Pa. 87-96.

2a. Gescuk, B. D., and J. C. Davis, Jr. 2002. Novel therapeutic agents for systemic lupus erythematosus. *Current Opinion in Rheumatology* 14:515-521.

3a. Karpouzas, G. A., and B. H. Hahn. 2003. Systemic lupus erythematosus. In *Targeted Therapies in Rheumatology*. J. S. Smolen, and P. E. Lipsky, eds. Martin Dunitz, London. 563-581.

4a. Bisoendial, R. J., J. J. Kastelein, J. H. Levels, J. J. Zwaginga, B. van den Bogaard, P. H. Reitsma, J. C. Meijers, D. Hartman, M. Levi, and E. S. Stroes. 2005. Activation of Inflammation and Coagulation After Infusion of C-Reactive Protein in Humans. *Circ Res* 96:714-716.

5a. Du Clos, T. W. 2000. Function of C-reactive protein. *Annals of Medicine* 32:274-278.

6a. Volanakis, J. E. 2001. Human C-reactive protein: expression, structure, and function. *Molecular Immunology* 38:189-197.

7a. Du Clos, T. W., and C. Mold. 2004. C-reactive protein: an activator of innate immunity and a modulator of adaptive immunity. *Immunol Res* 30:261-278.

8a. Du Clos, T. W. 1996. The interaction of C-reactive protein and serum amyloid P component with nuclear antigens. *Molecular Biology Reports* 23:253-260.

9a. Du Clos, T. W., L. T. Zlock, P. S. Hicks, and C. Mold. 1994. Decreased autoantibody levels and enhanced survival of (NZBxNZW) F1 mice treated with C-reactive protein. *Clinical Immunology and Immunopathology* 70:22-27.

10a. Szalai, A. J., C. T. Weaver, M. A. McCrory, F. W. van Ginkel, R. M. Reiman, J. F. Kearney, T. N. Marion, and J. E. Volanakis. 2003. Delayed lupus onset in (NZBxNZW) F1 mice expressing a human C-reactive protein transgene. *Arthritis & Rheumatism* 48:1602-1611.

11a. Rodriguez, W., C. Mold, M. Kataranovski, J. Hutt, L. L. Marnell, and T. W. Du Clos. 2005. Reversal of ongoing proteinuria in autoimmune mice by treatment with C-reactive protein. *Arthritis & Rheumatism* 52:642-650.

12a. Rodriguez, W., C. Mold, L. L. Marnell, J. Hutt, G. J. Silverman, D. Tran, and T. W. Du Clos. 2006. Prevention and reversal of nephritis in MRL/lpr mice with a single injection of C-reactive protein. *Arthritis Rheum* 54:325-335.

13a. Kono, D. H., and A. N. Theofilopoulos. 2000. Genetics of systemic autoimmunity in mouse models of lupus. *International Reviews of Immunology*. 19:367-387.

14a. Daikh, D. I., and D. Wofsy. 2001. Cutting edge: reversal of murine lupus nephritis with CTLA4Ig and cyclophosphamide. *Journal of Immunology*. 166:2913-2916.

15a. Lawson, B. R., G. J. Prud'homme, Y. Chang, H. A. Gardner, J. Kuan, D. H. Kono, and A. N. Theofilopoulos. 2000. Treatment of murine lupus with cDNA encoding IFN-gammaR/Fc. *Journal of Clinical Investigation* 106: 207-215.

16a. Foell, J., S. Strahotin, S. P. O'Neil, M. M. McCausland, C. Suwyn, M. Haber, P. N. Chander, A. S. Bapat, X. J. Yan, N. Chiorazzi, M. K Hoffmann, and R. S. Mittler. 2003. CD137 costimulatory T cell receptor engagement reverses acute disease in lupus-prone NZBxNZW F1 mice. *J Clin Invest* 111:1505-1518.

17a. Tesch, G. H., S. Maifert, A. Schwarting, B. J. Rollins, and V. R. Kelley. 1999. Monocyte chemoattractant protein 1-dependent leukocytic infiltrates are responsible for autoimmune disease in MRL-Fas(lpr) mice. *Journal of Experimental Medicine* 190:1813-1824.

18a. Du Clos, T. W. 2003. C-reactive protein as a regulator of autoimmunity and inflammation. *Arthritis Rheum* 48:1475-1477.

19a. Ogden, C. A., and K. B. Elkon. 2005. Single-dose therapy for lupus nephritis: C-reactive protein, nature's own dual scavenger and immunosuppressant. *Arthritis Rheum* 52:378-381.

20a. Walport, M. J. 2000. Lupus, DNase and defective disposal of cellular debris. *Nature Genetics* 25:135-136.

21a. Burlingame, R. W., IL L. Rubin, R. S. Balderas, and A. N. Theofilopoulos. 1993. Genesis and evolution of antichromatin autoantibodies in murine-lupus implicates T-dependent immunization with self antigen. *Journal of Clinical Investigation* 91:1687-1696.

22a. Burlingame, R. W., M. L. Boey, G. Starkebaum, and R. L. Rubin. 1994. The central role of chromatin in autoimmune responses to histones and DNA in systemic lupus erythematosus. *Journal of Clinical Investigation* 94:184-192.

23a. Casciola-Rosen, L. A., G. Anhalt, and A. Rosen. 1994. Autoantigens targeted in systemic lupus erythematosus are clustered in two populations of surface structures on apoptotic keratinocytes. *Journal of Experimental Medicine* 179:1317-1330.

24a. Carroll, M. C. 2000. A protective role for innate immunity in autoimmune disease. *Clinical Immunology* 95:S30-38.

25a. Burlingame, R. W., M. A. Volzer, J. Harris, and T. W. Du Clos. 1996. The effect of acute phase proteins on clearance of chromatin from the circulation of normal mice. *Journal of Immunology* 156:4783-4788.

26a. Bickerstaff, M. C., M. Botto, W. L. Hutchinson, J. Herbert, G. A. Tennent, A. Bybee, D. A. Mitchell, H. T. Cook, P. J. Butler, M. J. Walport, and M. B. Pepys. 1999. Serum amyloid P component controls chromatin degradation and prevents antinuclear autoimmunity. *Nat Med* 5:694-697.

27a. Familian, A., B. Zwart, H. G. Huisman, I. Rensink, D. Roem, P. L. Hordijk, L. A. Aarden, and C. E. Hack. 2001. Chromatin-independent binding of serum amyloid P component to apoptotic cells. *Journal of Immunology* 167:647-654.

28a. Gershov, D., S. Kim, N. Brot, and K. B. Elkon. 2000. C-reactive protein binds to apoptotic cells, protects the cells from assembly of the terminal complement components, and sustains an antiinflammatory innate immune response: implications for systemic autoimmunity. *Journal of Experimental Medicine* 192:1353-1363.

29a Mold, C., R. Baca, and T. W. Du Clos. 2002. Serum amyloid P component and C-reactive protein opsonize apoptotic cells for phagocytosis through Fcg receptors. *Journal of Autoimmunity* 19:147-154.

30a. Taylor, P. R., A. Carugati V. A. Fadok, H. T. Cook, M. Andrews, M. C. Carroll, J. S. Savill, P. M. Henson, M. Botto, and M J. Walport 2000. A hierarchical role for classical pathway complement proteins in the clearance of apoptotic cells in vivo. *J Exp Med* 192:359-366.

31a. Crow, M. K., K A. Kirou, and J. Wohlgemuth 2003. Microarray analysis of interferon-regulated genes in SLE. *Autoimmunity* 36:481-490.

32a. Baechler, E. C., P. K. Gregersen, and T. W. Behrens. 2004. The emerging role of interferon in human systemic lupus erythematosus. *Curr. Opin. Immunol.* 16:801-807.

33a Ronnblom, L., M. L. Eloranta, and G. V. Aim. 2006. The type I interferon system in systemic lupus erythematosus. *Arthritis Rheum* 54:408-420.

34a. Bave, U., M. Magnusson, M. L. Eloranta, A. Perers, G. V. Alm, and L. Ronnblom. 2003. Fc gamma RIIa is expressed on natural IFN-alpha-producing cells (plasmacytoid dendritic cells) and is required for the IFN-alpha production induced by apoptotic cells combined with lupus IgG. *J Immunol* 171:3296-3302.

35a. Martin, D. A., and K B. Elkon. 2005. Autoantibodies make a U-turn: the toll hypothesis for autoantibody specificity. *J. Exp. Med.* 202:1465-1469.

36a. Boule, M. W., C. Broughton, F. Mackay, S. Akira, A. Marshak-Rothstein, and I. R. Rifkin. 2004. Toll-like receptor 9-dependent and -independent dendritic cell activation by chromatin-immunoglobulin G complexes. *J. Exp. Med.* 199:1631-1640.

37a. Xia, D., and D. Samols. 1997. Transgenic mice expressing rabbit C-reactive protein are resistant to endotoxemia. *Proc Natl Acad Sci USA* 94:2575-2580.

38a. Mold, C., W. Rodriguez, B. Rodic-Polic, and T. W. Du Clos. 2002. C-reactive protein mediates protection from lipopolysaccharide through interactions with Fc gamma R. *J. Immunol.* 169:7019-7025.

39a Ahmed, N., R. Thorley, D. Xia, D. Samols, and R. O. Webster. 1996. Transgenic mice expressing rabbit C-reactive protein exhibit diminished chemotactic factor-induced alveolitis. *American Journal of Respiratory and Critical Care Medicine* 153:1141-1147.

40a Stein, M. P., C. Mold, and T. W. Du Clos. 2000. C-reactive protein binding to murine leukocytes requires Fc gamma receptors. *J Immunol* 164:1514-1520.

41a Bharadwaj, D., M. P. Stein, M. Volzer, C. Mold, and T. W. Du Clos. 1999. The major receptor for C-reactive protein on leukocytes is Fcg receptor II. *Journal of Experimental Medicine* 190:585-590.

42a. Sutterwala F. S., G. J. Noel, P. Salgame, and D. M. Mosser. 1998. Reversal of proinflammatory responses by ligating the macrophage Fcg receptor type I. *Journal of Experimental Medicine* 188:217-222.

43a. Anderson, C. F., and D. M. Mosser. 2002. Biasing immune responses by directing antigen to macrophage Fcg receptors. *J. Immunol.* 168:3697-3701.

44a. Park, S. Y., S. Ueda, H. Ohno, Y. Hamanao, M. Tanaka, T. Shiratori, T. Yamazaki, H. Arase, N. Arase, A. Karasawa, S. Sato, B. Ledernann, Y. Kondo, K. Okumura, C. Ra, and T. Saito. 1998. Resistance of Fc receptor-deficient mice to fatal glomerulonephritis. *J. Clin. Invest.* 102:1229-1238.

45a. Tarzi, R. M., K. A. Davies, M. G. Robson, L. Fossati-Jimack, T. Saito, M. J. Walport, and H. T. Cook. 2002. Nephrotoxic nephritis is mediated by Fcg receptors on circulating leukocytes and not intrinsic renal cells. *Kidney International* 62:2087-2096.

46a. Kaneko, Y., F. Nimmerjahn, M. P. Madaio, and J. V. Ravetch 2006. Pathology and protection in nephrotoxic nephritis is determined by selective engagement of specific Fc receptors. *J Exp Med.*

47a. van Rooijen, N., and A. Sanders. 1994. Liposome mediated depletion of macrophages: mechanism of action, preparation of liposomes and applications. *J. Immunol. Meth.* 174:83-93.

48a. Du Clos, T. W., M. A. Volzer, F. F. Hahn, R. Xiao, C. Mold, and R. P. Searles. 1999. Chromatin clearance in C57B1/10 mice: interaction with heparan sulphate proteoglycans and receptors on Kupffer cells. *Clin Exp Immunol* 117:403-411.

49a. Kikawada, E., D. M. Lenda, and V. R. Kelley. 2003. IL-12 deficiency in MRL-Fas(lpr) mice delays nephritis and intrarenal IFN-gamma expression, and diminishes systemic pathology. *J Immunol* 170:3915-3925.

50a. Lenda, D. M., E. Kikawada, E. IL Stanley, and V. R. Kelley. 2003. Reduced macrophage recruitment, proliferation, and activation in colony-stimulating factor-1-deficient mice results in decreased tubular apoptosis during renal inflammation. *J Immunol* 170:3254-3262.

51a. Timoshanko, J. R., A. R. Kitching, Y. Iwakura, S. R. Holdsworth, and P. G. Tipping. 2004. Leukocyte-derived interleukin-1 beta interacts with renal interleukin-1 receptor I to promote renal tumor necrosis factor and glomerular injury in murine crescentic glomerulonephritis. *Am J Pathol* 164:1967-1977.

52a. Hasegawa, H., M. Kohno, M. Sasaki, A. Inoue, M. R. Ito, M. Terada, K. Hieshima, H. Maruyama, J. Miyazaki, O. Yoshie, M. Nose, and S. Fujita 2003. Antagonist of monocyte chemoattractant protein 1 ameliorates the initiation and progression of lupus nephritis and renal vasculitis in MRL/lpr mice. *Arthritis Rheum.* 48:2555-2566.

53a. Shimizu, S., H. Nakashima, K. Masutani, Y. Inoue, K Miyake, M. Akahoshi, Y. Tanaka, K. Egashira, H. Hirakata, T. Otsuka, and M. Hamda. 2004. Anti-monocyte chemoattractant protein-i gene therapy attenuates nephritis in MRL/lpr mice. *Rheumatology (Oxford)* 43:1121-1128.

54a. Noris, M., S. Bernasconi, F. Casiraghi, S. Soani, E. Gotti, G. Remuzzi, and A. Mantovani. 1995. Monocyte chemoattractant protein-1 is excreted in excessive amounts in the urine of patients with lupus nephritis. *Lab. Invest.* 73:804-809.

55a. Chan, R. W., F. M. Lai, E. K. Li, L. S. Tam, T. Y. Wong, C. Y. Szeto, P. K. Li and C. C. Szeto. 2004. Expression of chemokine and fibrosing factor messenger RNA in the urinary sediment of patients with lupus nephritis. *Arthritis Rheum* 50:2882-2890.

56a. Du Clos, T. W. 1989. C-reactive protein reacts with the U1 small nuclear ribonucleoprotein. *Journal of Immunology* 143:2553-2559.

57a. Kilpatrick, J. M., and J. E. Volanakis. 1991. Molecular genetics, structure, and function of C-reactive protein. *Immunol Res* 10:43-53.

58a. Russell, A. I., D. S. Cunninghame Graham, C. Shepherd, C. A. Roberton, J. Whittaker, J. Meeks, R. J. Powell, D. A. Isenberg, M. J. Walport, and T. J. Vyse. 2004. Polymorphism at the C-reactive protein locus influences gene expression and predisposes to systemic lupus erythematosus. *Human Molecular Genetics* 13:137-147.

59a. Ku, N. O., and R. F. Mortensen. 1993. Cloning and tissue-specific expression of the gene for mouse C-reactive protein. *Biochem. J.* 295 (Pt 2):379-386.

60a. Marnell, L., C. Mold, M. A. Volzer, R. W. Burlingame, and T. W. Du Clos. 1995. Expression and radiolabeling of human C-reactive protein in baculovirus-infected cell lines and *Trichoplusia ni* larvae. *Protein Expr Purif* 6:439-446.

61a. Siboo, R., and E. Kulisek. 1978. A fluorescent immunoassay for quantification of C-reactive protein. *J. Immunol. Meth.* 23:59-67.

62a Hutchinson, W. L., G. E. Noble, P. N. Hawkins, and M. B. Pepys. 1994. The pentraxins, C-reactive protein and serum amyloid P component, are cleared and catabolized by hepatocytes in vivo. *J. Clin. Invest.* 94:1390-1396.

63a. Vigushin, D. M., M. B. Pepys, and P. N. Hawkins. 1993. Metabolic and scintigraphic studies of radioiodinated human C-reactive protein in health and disease. *J. Clin. Invest.* 91:1351-1357.

64a. Katre, N. V. 1990. Immunogenicity of recombinant IL-2 modified by covalent attachment of polyethylene glycol. *J. Immunol.* 144:209-213.

65a. Daro, E., B. Pulendin, K. Brasel, M. Teepe, D. Pettit, D. H. Lynch, D. Vremec, L. Robb, K. Shortman, H. J. McKenna, C. R. Maliszewski, and E. Maraskovsky. 2000. Polyethylene glycol-modified GM-CSF expands CD11b(high)CD11c(high) but notCD11b(low)CD11c(high) murine dendritic cells in vivo: a comparative analysis with Flt3 ligand. *J. Immunol.* 165:49-58.

66a. Cunnane, G., O. T. Chan, G. Cassafer, S. Brindis, E. Kaufman T. S. Yen, and D. I. Daikh. 2004. Prevention of renal damage in murine lupus nephritis by CTLA-4Ig and cyclophosphamide. *Arthritis Rheum* 50:1539-1548.

67a. Qiao, J. H., L. W. Castellani, M. C. Fishbein, and A. J. Lusis. 1993. Immune-complex-mediated vasculitis increases coronary artery lipid accumulation in autoimmune-prone MRL mice. *Arterioscler. Thromb.* 13:932-943.

68a. Ridker, P. M. 2003. Clinical application of C-reactive protein for cardiovascular disease detection and prevention. *Circulation* 107:363-369.

69a. Albert, M. A., R. J. Glynn, and P. M. Ridker. 2003. Plasma concentration of C-reactive protein and the calculated Framingham Coronary heart disease risk score. *Circulation* 108:161-165.

70a. Hirschfield, G. M., J. R. Gallimore, M. C. Kahan, W. L. Hutchinson, C. A. Sabin, G.

M. Benson, A. P. Dhillon, G. A. Tennent, and M. B. Pepys. 2005. Transgenic human C-reactive protein is not proatherogenic in apolipoprotein E-deficient mice. *Proc. Natl. Acad. Sci. U.S.A.* 102:8309-8314.

71a. Paul, A., K. W. Ko, L. Li, V. Yechoor, M. A. McCrory, A. J. Szalai, and L. Chan. 2004. C-reactive protein accelerates the progression of atherosclerosis in apolipoprotein E-deficient mice. *Circulation* 109:647-655.

72a. Reifenberg, K., H. A. Lehr, D. Baskal, E. Wlese, S. C. Schaefer, S. Black, D. Samols, M. Torzewski, K. J. Lackner, M. Husmann, M. Blettner, and S. Bhakdi. 2005. Role of C-reactive protein in atherogenesis: can the apolipoprotein E knockout mouse provide the answer? *Arterioscler. Thromb. Vasc. Biol.* 25:1641-1646.

73a. Pepys, M. B., P. N. Hawkins, M. C. Kahan, G. A Tennent, J. R. Gallimore, D. Graham, C. A Sabin, A. Zychlinsky, and J. de Diego. 2005. Proinflammatory effects of bacterial recombinant human C-reactive protein are caused by contamination with bacterial products, not by C-reactive protein itself. *Circ Res* 97:e97-103.

74a. Taylor, K. E., J. C. Giddings, and C. W. van den Berg. 2005. C-Reactive Protein-Induced In Vitro Endothelial Cell Activation Is an Artifact Caused by Azide and Lipopolysaccharide. *Arterioscler Thromb Vasc Biol.*

75a. Pepys, M. B., G. M. Hirschfield, G. A. Tennent, J. R. Gallimore, M. C. Kahan, V. Bellotti, P. N. Hawkins, R. M. Myers, M. D. Smith, A. Polara, A. J. Cobb, S. V. Ley, J. A. Aquilina, C. V. Robinson, I. Sharif, G. A. Gray, C. A. Sabin, M. C. Jenvey, S. E. Kolstoe, D. Thompson, and S. P. Wood. 2006. Targeting C-reactive protein for the treatment of cardiovascular disease. *Nature* 440:1217-1221.

76a. Griselli, M., J. Herbert, W. L. Hutchinson, K. M. Taylor, M. Sahail, T. Drausz, and M. B. Pepys. 1999. C-reactive protein and complement are important mediators of tissue damage in acute myocardial infarction. *Journal of Experimental Medicine* 190:1733-1739.

77a. Mold, C., S, Nakayama, T. J. Holzer, H. Gewurz, and T. W. Du Clos. 1981. C-reactive protein is protective against *Streptococcus pneumoniae* infection in mice. *Journal of Experimental Medicine* 154:1703-1708.

78a. Mold, C., B. Rodic-Polic, and T. W. Du Clos. 2002. Protection from *Streptococcus pneumoniae* infection by C-reactive protein and natural antibody requires complement but not Fc gamma receptors. *J Immunol* 168:6375-6381.

79a. Bang, R., L. Marnell, C. Mold, M. P. Stein, K T. Du Clos, C. Chivington-Buck, and T. W. Du Clos. 2005. Analysis of binding sites in human C-reactive protein for Fcgamma RI, Fcgamma RIIa and C1q by site-directed mutagenesis. *J Biol Chem.*

80a. Agrawal, A., M. J. Simpson, S. Black, M. P. Carey, and D. Samols. 2002. A C-reactive protein mutant that does not bind to phosphocholine and pneumococcal C-polysaccharide. *J Immunol* 169:3217-3222.

81a. Agrawal, A., A. K Shrive, T. J. Greenhough, and J. E. Volanakis. 2001. Topology and structure of the C1q-binding site on C-reactive protein. *Journal of Immunology* 166:3998-4004.

82a. Agrawal, A., Y. Xu, D. Ansardi, K. J. Macon, and J. E. Volanakis. 1992. Probing the phosphocholine-binding site of human C-reactive protein by site-directed mutagenesis. *J. Biol. Chem.* 267:25352-25358.

83a. Du Clos, T. W., L. T. Zlock, and R. L. Rubin 1988. Analysis of the binding of C-reactive protein to histones and chromatic. *J Immunol* 141:4266-4270.

84a. Chang, M.-K., C. J. Binder, M. Torzewski, and J. L. Witztum. 2002. C-reactive aprotein binds to both oxidized LDL and apoptotic cells through recognition of a common ligand: Phosphorylcholine of oxidized phospholipids. *PNAS* 99:13043-13048.

85a. Du Clos, T. W., L. T. Zlock, and L. Marnell. 1991. Definition of a C-reactive protein binding determinant on histones. *J Biol Chem* 266:2167-2171.

86a. Bolland, S., and J. V. Ravetch 2000. Spontaneous autoimmune disease in Fc(gamma)RIIB-deficient mice results from strain-specific epistasis. *Immunity.* 13:277-285.

87a. Lagrand, W. K., H. W. M. Niessen, G.-J. Wolbink, L. H. Jaspars, C. A. Visser, F. W. A. Verheugt, C. J. L. M. Meijer, and C. E. Hack 1997. C-reactive protein colocalizes with complement in human hearts during acute myocardial infarction. *Circ.* 95:97-103.

88a. Ehrenstein, M. R., H. T. Cook, and M. S. Neuberger. 2000. Deficiency in serum immunoglobulin (Ig)M predisposes to development of IgG autoantibodies. *J Exp Med* 191:1253-1258.

89a. Peng, Y., R. Kowalewski, S. Kim, and K. B. Elkon. 2005. The role of IgM antibodies in the recognition and clearance of apoptotic cells. *Mol Immunol* 42:781-787.

90a. Nimmerjahn, F., and J. V. Ravetch 2006. Fcgamma receptors: old friends and new family members. *Immunity* 24:19-28.

91a. Nimmerjahn, F., P. Bruhns, K. Horiuchi, and J. V. Ravetch 2005. FcgammaRIV: a novel FcR with distinct IgG subclass specificity. *Immunity* 23:41-51.

92a. Ravetch. J. V., and Lanier. L. L. 2000. Immune inhibitory receptors. *Science* 290:84-89.

93a. Fadok, V. A., D. L. Bratton, and P. M. Henson. 2001. Phagocyte receptors for apoptotic cells: recognition, uptake, and consequences. *Journal of Clinical Investigation* 108:957-962.

94a. Mold, C., H. Gewurz, and T. W. Du Clos. 1999. Regulation of complement activation by C-reactive protein. *Immunopharmacology* 42:23-30.

95a. Jewell, W. S., L. L. Marnell, L. A. Rokeach, and T. W. Du Clos. 1993. C-reactive protein (CRP) binding to the Sm-D protein of snRNPS. Identification of a short polypeptide binding region. *Molecular Immunology* 30:701-708.

96a. Riemekasten, M., K Trebeljahr, H. Hausdorf, and H. Burmester. 1998. A novel epitope on the C-terminus of SmD1 is recognized by the majority of sera from patients with systemic lupus erythematosus. *Journal of Clinical Investigation* 102:754-763.

97a. Riemekasten, G., A. Kawald, C. Weiss, A. Meine, J. Marell, R Klein, B. Hocher, C. Meisel, G. Hausdorf, P, Manz, T. Kamradt, G.-R. Burmester, and F. Hiepe. 2001. Strong acceleration of murine lupus by injection of the SmD183-119 peptide. *Arthritis & Rheumatism* 44:2435-2445.

98a. Reuter, R, and IL Lührmann. 1986. Immunization of mice with purified U1 small nuclear ribonucleoprotein (RNP) induces a pattern of antibody specificities characteristic of the anti-Sm and anti-RNP autoimmune response of patients with lupus erythematosus, as measured by monoclonal antibodies. *Proc. Natl. Acad. Sci. USA* 83:8689-8693.

99a. Nakayama, S., T. W. Du Clos, H. Gewurz, and C. Mold. 1984. Inhibition of antibody responses to phosphocholine by C-reactive protein. *J Immunol* 132:1336-1340.

100a. Mevorach, D., J. L. Zhou, X Song, and K. B. Elkon. 1998. Systemic exposure to irradiated apoptotic cells induces autoantibody production. *J Exp Med* 188:387-392.

101a. Chang, M. K., C. J. Binder, Y. L Miller, G. Subbanagounder, G. J. Silverman, J. A. Berliner, and J. L. Witztum. 2004. Apoptotic cells with oxidation-specific epitopes are immunogenic and proinflammatory. *J Exp Med* 200:1359-1370.

102a. Fadok, V. A., D. L. Bratton, A. Konowal, P. W. Freed, J. Y. Westcott, and P. M. Henson. 1998. Macrophages that have ingested apoptotic cells in vitro inhibit proinflammatory cytokine production through autocrine/paracrine mechanisms involving TGFb, PGE2, and PAF. *Journal of Clinical Investigation* 101:890-898.

103a. Du Clos, T. W., R. L. Rubin, and E. M. Tan. 1986. Monoclonal antibody for DNA measurement in biological fluids. *J Immunol Methods* 88:185-192.

104a. Duramad, O., K. L. Fearon, J. H. Chan, H. Kanzler, J. D. Marshall, R. L. Coffman, and F. J. Barrat. 2003. IL-10 regulates plasmacytoid dendritic cell response to CpG-containing immunostimulatory sequences. *Blood* 102:4487-4492.

105a. Bave, U., H. Vailin, G. V. Alm, and L. Ronnblom. 2001. Activation of natural interferon-alpha producing cells by apoptotic U937 cells combined with lupus IgG and its regulation by cytokines. *J Autoimmun* 17:71-80.

106a. Means, T. K., E. Latz, F. Hayashi, M. R. Murali, D. T. Golenbock, and A. D. Luster. 2005. Human lupus autoantibody-DNA complexes activate DCs through cooperation of CD32 and TLR9. *J Clin Invest* 115:407-417.

107a. Szalai, A. J., S. Nataf, X.-Z. Hu, and S. R. Barnum. 2002. Experimental allergic encephalomyelitis is inhibited in transgenic mice expressing human C-reactive protein. *Journal of Immunology* 168:5792-5797.

108a. Hang, L., J. H. A. Slack, C., S. Izui, A. N. Theofilopoulos, and F. J. Dixon. 1978. Increased spontaneous polyclonal activation of B lymphocytes in mice with spontaneous autoimmune disease. *Journal of Immunology* 121:2213-2219.

109a. Du Clos, T. W., E. M. Tan, and F. J. Dixon. 1986. Ultraviolet light irradiation of NZB/W mice produces a dramatic fall in levels of autoantibodies. *Arthritis and Rheumatism* 29:S59.

110a. Lenda, D. M., E. R. Stanley, and V. R. Kelley. 2004. Negative role of colony-stimulating factor-1 in macrophage, T cell, and B cell mediated autoimmune disease in MRL-Fas(lpr) mice. *J Immunol* 173:4744-4754.

111a. Carvalho-Pinto, C. E., M. I. Garcia, M. Mellado, J. M. Rodriguez-Frade, J. Martin-Caballero, J. Flores, A. C. Martinez, and D. Balomenos. 2002. Autocrine production of IFN-gamma by macrophages controls their recruitment to kidney and the development of glomerulonephritis in MRL/lpr mice. *Journal of Immunology* 169:1058-1067.

112a. Geissmann, F., S. Jung, and D. R. Littman. 2003. Blood monocytes consist of two principal subsets with distinct migratory properties. *Immunity* 19:71-82.

113a. Serbina, N. V., and E. G. Pamer. 2006. Monocyte emigration from bone marrow during bacterial infection requires signals mediated by chemokine receptor CCR2. *Nat Immunol* 7:311-317.

114a. Goodyear, C. S., and G. J. Silverman. 2003. Death by a B cell superantigen: In vivo VH-targeted apoptotic supraclonal B cell deletion by a Staphylococcal Toxin. *J Exp Med* 197:1125-1139.

115a. Feral, C. C., D. M. Rose, J. Han, N. Fox, G. J. Silverman, K. Kaushansky, and M. H Ginsberg. 2006. Blocking the {alpha}4 integrin{alpha}paxillin interaction selectively impairs mononuclear leukocyte recruitment to an inflammatory site. *J. Clin. Invest.* 116:715-723.

116a. Foussat, A., F. Cottrez, V. Brun, N. Fournier, J. P. Breittmayer, and H. Groux. 2003. A comparative study between T regulatory Type 1 and CD4+CD25+T cells in the control of inflammation. The complex role of interleukin-10 in autoimmunity. *Journal of Immunology* 171:5018-5026.

117a. Ruprecht, C. R., M. Gattorno, F. Ferlito, A. Gregorio, A. Martini, A. Lanzavecchia, and F. Sallusto. 2005. Coexpression of CD25 and CD27 identifies FoxP3+ regulatory T cells in inflamed synovia. *J Exp Med* 201:1793-1803.

The invention claimed is:

1. A mutant polypeptide having an amino acid sequence according to SEQ ID No:2, SEQ ID No:3, SEQ ID No:4, SEQ ID No:5, SEQ ID No:6, SEQ ID No:7 or SEQ ID No:8.

2. The polypeptide according to claim 1 having an amino acid sequence according to SEQ ID No:6, SEQ ID No:7 or SEQ ID No:8.

3. The polypeptide according to claim 1 having an amino acid sequence according to SEQ ID No: 2, SEQ ID No:3, SEQ ID No:4; SEQ ID No:5 or SEQ ID No:6.

4. The polypeptide according to claim 1 having an amino acid sequence according to SEQ. ID No:5 or SEQ ID No:6.

5. The polypeptide according to claim 1 having an amino acid sequence according to SEQ ID No:6 or SEQ ID No:7.

6. The polypeptide according to claim 1 having an amino acid sequence according to SEQ ID No:3, SEQ ID No:4, SEQ ID No:5, SEQ ID No:6, SEQ ID No:7 or SEQ ID No:8.

7. A pharmaceutical composition comprising a mutant polypeptide of CRP in combination with a pharmaceutically acceptable additive, excipient, or mixtures thereof; wherein said mutant polypeptide has an amino: acid sequence according to SEQ ID No:2, SEQ ID No:3, SEQ ID No:4, SEQ ID No:5, SEQ ID No:6, SEQ ID No:7 or SEQ ID No:8.

8. The composition according to claim 7 wherein said compound is a mutant polypeptide having an amino acid sequence according to SEQ ID No:4, SEQ ID No:5, SEQ ID No:6, SEQ ID No:7 or SEQ ID No:8.

9. The composition according to claim 7 wherein said mutant polypeptide has an amino acid sequence according to SEQ ID No:6, SEQ ID No:7 or SEQ ID No:8.

10. The composition according to claim 7 wherein said mutant polypeptide has an amino acid sequence according to SEQ ID No: 2, SEQ ID No:3, SEQ ID No:4, SEQ ID No:5 or SEQ ID No:6.

11. The composition according to claim 7 wherein said mutant polypeptide has an amino acid sequence according to SEQ ID No:5 or SEQ ID No:6.

12. The composition according to claim 7 wherein said mutant polypeptide has an amino acid sequence according to SEQ ID No:6 or SEQ ID No :7.

13. The composition according to claim 7 wherein said mutant polypeptide has an amino acid sequence according to SEQ ID No:3, SEQ ID No:4, SEQ ID No:5, SEQ ID No:6, SEQ ID No:7 or SEQ ID No:8.

* * * * *

SEQUENCE LISTING

<160> NUMBER OF SEQ ID NOS: 12

<210> SEQ ID NO 1
<211> LENGTH: 206
<212> TYPE: PRT
<213> ORGANISM: Homo sapiens

<400> SEQUENCE: 1

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205
```

<210> SEQ ID NO 2
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 2

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asn
```

```
            100                 105                 110
Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
            130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
            195                 200                 205

<210> SEQ ID NO 3
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 3

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
        50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Ala
            100                 105                 110

Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
            130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
            195                 200                 205

<210> SEQ ID NO 4
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 4

Gln Thr Asp Met Ser Arg Lys Ala Phe Val Phe Pro Lys Glu Ser Asp
```

```
                1               5                  10                 15
Thr Ser Tyr Val Ser Leu Lys Ala Pro Leu Thr Lys Pro Leu Lys Ala
                20                 25                 30

Phe Thr Val Cys Leu Arg Phe Tyr Thr Glu Leu Ser Ser Thr Arg Gly
                35                 40                 45

Tyr Ser Ile Phe Ser Tyr Ala Thr Lys Arg Gln Asp Asn Glu Ile Leu
50                 55                 60

Ile Phe Trp Ser Lys Asp Ile Gly Tyr Ser Phe Thr Val Gly Gly Ser
65                 70                 75                 80

Glu Ile Leu Phe Glu Val Pro Glu Val Thr Val Ala Pro Val His Ile
                85                 90                 95

Cys Thr Ser Trp Glu Ser Ala Ser Gly Ile Val Glu Phe Trp Val Asp
                100                105                110

Gly Lys Pro Arg Val Arg Lys Ser Leu Lys Lys Gly Tyr Thr Val Gly
                115                120                125

Ala Glu Ala Ser Ile Ile Leu Gly Gln Glu Gln Asp Ser Phe Gly Gly
                130                135                140

Asn Phe Glu Gly Ser Gln Ser Leu Val Gly Asp Ile Gly Asn Val Asn
145                150                155                160

Met Trp Asp Phe Val Leu Ser Pro Asp Glu Ile Asn Thr Ile Tyr Leu
                165                170                175

Gly Gly Pro Phe Ser Pro Asn Val Leu Asn Trp Arg Ala Leu Lys Tyr
                180                185                190

Glu Val Gln Gly Glu Val Phe Thr Lys Pro Gln Leu Trp Pro
                195                200                205
```

<210> SEQ ID NO 5
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 5

```
Gln Thr Asp Met Ser Arg Lys Ala Phe Val Phe Pro Lys Glu Ser Asp
1               5                  10                 15

Thr Ser Tyr Val Ser Leu Lys Ala Pro Leu Thr Lys Pro Leu Lys Ala
                20                 25                 30

Phe Thr Val Cys Leu His Phe Tyr Thr Glu Leu Ser Ser Thr Arg Gly
                35                 40                 45

Tyr Ser Ile Phe Ser Tyr Ala Thr Lys Arg Gln Asp Asn Glu Ile Leu
50                 55                 60

Ile Phe Trp Ser Lys Asp Ile Gly Tyr Ser Phe Thr Val Gly Gly Ser
65                 70                 75                 80

Glu Ile Leu Phe Glu Val Pro Glu Val Thr Val Ala Pro Val His Ile
                85                 90                 95

Cys Thr Ser Trp Glu Ser Ala Ser Gly Ile Val Glu Phe Trp Val Asp
                100                105                110

Gly Lys Pro Arg Val Arg Lys Ser Leu Lys Lys Gly Tyr Thr Val Gly
                115                120                125

Ala Glu Ala Ser Ile Ile Leu Gly Gln Glu Gln Asp Ser Phe Gly Gly
                130                135                140

Asn Phe Glu Gly Ser Gln Ser Leu Val Gly Asp Ile Gly Asn Val Asn
145                150                155                160

Met Trp Asp Phe Val Leu Ser Pro Ala Glu Ile Asn Thr Ile Tyr Leu
                165                170                175
```

```
Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 6
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 6

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Leu Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 7
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 7

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80
```

```
Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Gln
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 8
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 8

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Ala Trp Ser Lys Asp Ile Gly Tyr Ser Phe Thr Val Gly Gly Ser
65                  70                  75                  80

Ala Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 9
<211> LENGTH: 12
<212> TYPE: PRT
<213> ORGANISM: Artificial Sequence
<220> FEATURE:
```

```
<223> OTHER INFORMATION: Synthetic polypeptide

<400> SEQUENCE: 9

Ile Tyr Leu Gly Gly Pro Phe Ser Pro Asn Val Leu
1               5                  10

<210> SEQ ID NO 10
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 10

Leu Ser Pro Asp Glu Ile Asn Thr Ile Tyr Leu Gly Gly Pro Phe
1               5                  10                  15

<210> SEQ ID NO 11
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 11

Leu Ser Pro Asp Glu Ile Asn Thr Ile Tyr Leu Gly Gly Pro Phe Ser
1               5                  10                  15

Pro Asn Val Leu
            20

<210> SEQ ID NO 12
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 12

Lys Pro Gln Leu Trp Pro
1               5
```